(12) United States Patent
Ferguson et al.

(10) Patent No.: US 7,458,954 B2
(45) Date of Patent: *Dec. 2, 2008

(54) SAFETY SHIELD FOR MEDICAL NEEDLES

(75) Inventors: F. Mark Ferguson, Salt Lake City, UT (US); David L. Thorne, Kaysville, UT (US); Donald D. Solomon, North Salt Lake, UT (US); Daniel K. Smith, Woods Cross, UT (US); Jeremy W. Snow, North Salt Lake, UT (US); B. Chance Bagley, American Fork, UT (US); Craig N. Thome, Syracuse, UT (US)

(73) Assignee: Specialized Health Products, Inc., Minneapolis, MN (US)

( * ) Notice: Subject to any disclaimer, the term of this patent is extended or adjusted under 35 U.S.C. 154(b) by 624 days.

This patent is subject to a terminal disclaimer.

(21) Appl. No.: 10/660,083

(22) Filed: Sep. 11, 2003

(65) Prior Publication Data
US 2004/0092889 A1 May 13, 2004

Related U.S. Application Data

(63) Continuation-in-part of application No. 10/409,819, filed on Apr. 8, 2003, now Pat. No. 6,796,962.

(60) Provisional application No. 60/424,655, filed on Nov. 7, 2002.

(51) Int. Cl.
*A61M 5/00* (2006.01)

(52) U.S. Cl. .................................... 604/110

(58) Field of Classification Search ............... 604/110, 604/263, 192, 198, 197, 162, 171, 164.08, 604/264, 167.06, 170.02; 128/919
See application file for complete search history.

(56) References Cited

U.S. PATENT DOCUMENTS

| 1,436,707 | A | 11/1922 | Gaschke |
| 4,332,323 | A | 6/1982 | Reenstierna ............... 206/365 |
| 4,373,526 | A | 2/1983 | Kling ....................... 128/215 |
| 4,762,516 | A | 8/1988 | Luther ...................... 605/164 |

(Continued)

FOREIGN PATENT DOCUMENTS

EP 0 702 972 B1 7/1995

(Continued)

OTHER PUBLICATIONS

Notice of Allowance and Fee(s) Due and Notice of Allowability dated Jun. 9, 2004 in U.S. Appl. No. 10/409,819.

(Continued)

*Primary Examiner*—Nicholas D Lucchesi
*Assistant Examiner*—Christopher D Koharski
(74) *Attorney, Agent, or Firm*—Steel Rives LLP

(57) ABSTRACT

In some arrangements, a medical needle shield apparatus can include a binding member disposed within a shield. The binding member can include a retainer that can engaged a medical needle to prevent inclination of the binding member, and can include one or more drag inducing members that can engage the needle. In some arrangements, the apparatus can include a hub retainer.

52 Claims, 55 Drawing Sheets

U.S. PATENT DOCUMENTS

| | | | | |
|---|---|---|---|---|
| 4,790,828 | A | 12/1988 | Dombrowski | 604/198 |
| 4,804,371 | A | 2/1989 | Vaillancourt | 604/198 |
| 4,826,490 | A | 5/1989 | Byrne | 604/198 |
| 4,832,696 | A | 5/1989 | Luther | 604/164 |
| 4,834,718 | A | 5/1989 | McDonald | 604/195 |
| 4,846,811 | A | 7/1989 | Vanderhoof | 604/263 |
| 4,917,669 | A | 4/1990 | Bonaldo | 604/164 |
| 4,929,241 | A | 5/1990 | Kulli | 604/263 |
| 4,931,048 | A | 6/1990 | Lopez | 604/110 |
| 4,944,725 | A | 7/1990 | McDonald | 604/164 |
| 4,950,252 | A | 8/1990 | Luther | 604/198 |
| 4,952,207 | A | 8/1990 | Lemieux | 604/164 |
| 4,964,854 | A | 10/1990 | Luther | 604/166 |
| 4,978,344 | A | 12/1990 | Dombrowski | 604/198 |
| 4,994,041 | A | 2/1991 | Dombrowski | 604/164 |
| 5,007,901 | A | 4/1991 | Shields | 604/110 |
| 5,049,136 | A | 9/1991 | Johnson | 604/198 |
| 5,051,109 | A | 9/1991 | Simon | 604/263 |
| 5,053,017 | A | 10/1991 | Chamuel | 604/192 |
| 5,059,180 | A | 10/1991 | McLees | 604/110 |
| 5,084,023 | A | 1/1992 | Lemieux | 604/167 |
| 5,084,030 | A | 1/1992 | Byrne | 604/198 |
| 5,085,648 | A | 2/1992 | Purdy | 604/198 |
| 5,127,905 | A | 7/1992 | Lemieux | 604/164 |
| 5,135,504 | A | 8/1992 | McLees | 604/164 |
| 5,147,327 | A | 9/1992 | Johnson | 604/198 |
| 5,171,229 | A | 12/1992 | McNeil | 604/192 |
| 5,183,468 | A | 2/1993 | McLees | 604/164 |
| 5,205,829 | A | 4/1993 | Lituchy | 604/164 |
| 5,215,528 | A | 6/1993 | Purdy | 604/164 |
| 5,300,045 | A | 4/1994 | Plassche | 604/263 |
| 5,312,371 | A | 5/1994 | Dombrowski | 604/198 |
| 5,322,517 | A | 6/1994 | Sircom | 604/198 |
| 5,328,482 | A * | 7/1994 | Sircom et al. | 604/164.08 |
| 5,334,158 | A | 8/1994 | McLees | 604/110 |
| 5,342,310 | A | 8/1994 | Ueyama | 604/110 |
| 5,344,408 | A | 9/1994 | Partika | 604/192 |
| 5,348,544 | A | 9/1994 | Sweeney | 604/192 |
| 5,411,486 | A | 5/1995 | Zadini | 604/198 |
| 5,417,659 | A | 5/1995 | Gaba | 604/110 |
| 5,419,766 | A | 5/1995 | Chang | 604/110 |
| 5,423,766 | A | 6/1995 | Di Cesare | 604/192 |
| 5,458,658 | A | 10/1995 | Sircom | 604/192 |
| 5,478,313 | A | 12/1995 | White | 604/110 |
| 5,487,733 | A | 1/1996 | Caizza et al. | 604/110 |
| 5,531,704 | A | 7/1996 | Knotek | 604/192 |
| 5,533,974 | A | 7/1996 | Gaba | 604/110 |
| 5,538,508 | A | 7/1996 | Steyn | 604/192 |
| 5,549,570 | A | 8/1996 | Rogalsky | 604/198 |
| 5,558,651 | A | 9/1996 | Crawford et al. | 604/263 |
| 5,562,624 | A | 10/1996 | Righi et al. | 604/110 |
| 5,562,633 | A | 10/1996 | Wozencroft | 604/171 |
| 5,582,597 | A | 12/1996 | Brimhall et al. | 604/192 |
| 5,584,809 | A | 12/1996 | Gaba | 604/110 |
| 5,584,810 | A | 12/1996 | Brimhall | 604/110 |
| 5,584,818 | A | 12/1996 | Morrison | 604/197 |
| 5,599,310 | A | 2/1997 | Bogert | 604/164 |
| 5,601,532 | A | 2/1997 | Gaba | 604/110 |
| 5,610,536 | A | 3/1997 | Diba | 604/263 |
| 5,611,781 | A | 3/1997 | Sircom | 604/164 |
| 5,662,610 | A | 9/1997 | Sircom | 604/110 |
| 5,683,365 | A | 11/1997 | Brown | 604/110 |
| 5,697,907 | A | 12/1997 | Gaba | 604/110 |
| 5,718,688 | A | 2/1998 | Wozencroft | 604/164 |
| 5,725,504 | A | 3/1998 | Collins | 604/165 |
| 5,749,856 | A | 5/1998 | Zadini | 604/162 |
| 5,853,393 | A | 12/1998 | Bogert | 604/165 |
| 5,879,337 | A | 3/1999 | Kuracina | 604/192 |
| 5,882,337 | A | 3/1999 | Bogert | 604/110 |
| 5,910,130 | A | 6/1999 | Caizza et al. | 604/110 |
| 5,911,705 | A | 6/1999 | Howell | 604/110 |
| 5,919,168 | A | 7/1999 | Wheeler | |
| 5,938,641 | A | 8/1999 | Villanueva | |
| 5,947,936 | A | 9/1999 | Bonds | |
| 5,951,515 | A | 9/1999 | Osterlind | 604/110 |
| 5,951,523 | A | 9/1999 | Osterlind et al. | |
| 5,964,731 | A | 10/1999 | Kovelman | |
| 5,980,488 | A | 11/1999 | Thorne | 604/110 |
| 6,001,080 | A | 12/1999 | Kuracina | 604/171 |
| 6,004,294 | A | 12/1999 | Brimhall | 604/164 |
| 6,010,487 | A | 1/2000 | DeMichele et al. | |
| 6,015,397 | A | 1/2000 | Elson et al. | |
| 6,022,366 | A | 2/2000 | Schraga | |
| 6,117,108 | A | 9/2000 | Woehr | 604/110 |
| 6,132,401 | A | 10/2000 | Van Der Meyden | 604/195 |
| 6,193,694 | B1 | 2/2001 | Bell | 604/192 |
| 6,203,527 | B1 | 3/2001 | Zadini | 604/110 |
| 6,210,373 | B1 | 4/2001 | Allmon | 604/192 |
| 6,221,047 | B1 | 4/2001 | Green et al. | 604/164 |
| 6,280,419 | B1 | 8/2001 | Vojtasek | 604/192 |
| 6,287,278 | B1 | 9/2001 | Woehr et al. | 604/110 |
| 6,406,459 | B1 | 6/2002 | Allmon | 604/192 |
| 6,443,927 | B1 | 9/2002 | Cook | 604/110 |
| 6,443,929 | B1 | 9/2002 | Kuracina et al. | 604/192 |
| 6,585,704 | B2 | 7/2003 | Luther et al. | 604/263 |
| 6,595,955 | B2 | 7/2003 | Ferguson et al. | |
| 6,616,630 | B1 | 9/2003 | Woehr et al. | 604/110 |
| 6,623,458 | B2 | 9/2003 | Woehr et al. | 604/192 |
| 6,629,959 | B2 | 10/2003 | Kuracina et al. | 604/192 |
| 6,652,486 | B2 | 11/2003 | Bialecki et al. | 604/110 |
| 6,682,510 | B2 | 1/2004 | Niermann | 604/263 |
| 6,689,102 | B2 | 2/2004 | Greene | 604/164.08 |
| 6,695,814 | B2 | 2/2004 | Greene et al. | 604/164.08 |
| 7,004,927 | B2 | 2/2006 | Ferguson et al. | |
| 7,179,244 | B2 | 2/2007 | Smith et al. | |
| 2002/0099339 | A1 | 7/2002 | Niermann | 604/263 |
| 2002/0107483 | A1 | 8/2002 | Cook | 604/164.01 |
| 2002/0177813 | A1 | 11/2002 | Adams et al. | 604/164.07 |
| 2002/0177818 | A1 | 11/2002 | Vaillancourt | 604/198 |
| 2002/0193745 | A1 | 12/2002 | Ferguson | 604/192 |
| 2003/0036731 | A1 | 2/2003 | Wilkinson et al. | 604/198 |
| 2003/0114797 | A1 | 6/2003 | Vaillancourt et al. | 604/171 |
| 2003/0135157 | A1 | 7/2003 | Saulenas et al. | 604/110 |
| 2003/0144627 | A1 | 7/2003 | Woehr et al. | 604/110 |
| 2003/0181875 | A1 | 9/2003 | Bressler et al. | 604/263 |
| 2003/0195471 | A1 | 10/2003 | Woehr et al. | 604/164.08 |
| 2003/0195479 | A1 | 10/2003 | Kuracina et al. | 604/263 |
| 2003/0216687 | A1 | 11/2003 | Hwang | 604/110 |
| 2004/0010227 | A1 | 1/2004 | Riesenberger et al. | 604/110 |
| 2004/0049155 | A1* | 3/2004 | Schramm | 604/110 |
| 2004/0049163 | A1 | 3/2004 | Murashita | 604/263 |
| 2004/0078003 | A1 | 4/2004 | Smith et al. | |
| 2004/0111057 | A1 | 6/2004 | Wilkinson | 604/110 |

FOREIGN PATENT DOCUMENTS

| | | |
|---|---|---|
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 | 1/2004 |
| WO | WO 97/42989 | 11/1997 |
| WO | WO 01/10488 A1 | 2/2001 |
| WO | WO 01/56642 | 8/2001 |
| WO | WO 02/45786 A2 | 6/2002 |
| WO | WO 03/103757 | 12/2003 |

OTHER PUBLICATIONS

Amendment and Response dated Mar. 18, 2004 in U.S. Appl. No. 10/409,819.

Office Action dated Mar. 5, 2004 in U.S. Appl. No. 10/409,819.

* cited by examiner

SAFETY SHIELD FOR MEDICAL NEEDLES

CROSS-REFERENCE TO RELATED APPLICATIONS

This patent application is a continuation-in-part of U.S. Utility patent application Ser. No. 10/409,819, filed in the U.S. Patent and Trademark Office on Apr. 8, 2003 now U.S. Pat. No. 6,796,962 by Ferguson et al., which claims priority to U.S. Utility patent application Ser. No. 10/322,288, filed in the U.S. Patent and Trademark Office on Dec. 17, 2002 by Ferguson et al., and U.S. Provisional Patent application Ser. No. 60/424,655, filed in the U.S. Patent and Trademark Office on Nov. 7, 2002 by Bagley et al., and U.S. Utility patent application Ser. No. 10/202,201, filed in the U.S. Patent and Trademark Office on Jul. 23, 2002 by Ferguson, which is a continuation-in-part of U.S. Utility patent application Ser. No. 09/809,357, filed in the U.S. Patent and Trademark Office on Mar. 15, 2001 by Ferguson et al., the entire contents of each of these disclosures being hereby incorporated by reference herein.

BACKGROUND

1. Technical Field

The present disclosure generally relates to safety shields for medical needles, and more particularly, to safety shields that protect a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus which employs a safety shield slidably movable along a medical needle to prevent hazardous exposure to a needle tip. Such a needle shield apparatus should be easily and reliably movable to shield a needle tip of a needle cannula.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a shield that is extensible from a retracted position to an extended position to enclose a distal end of a needle. A binding member is disposed within the shield and defines binding surfaces that form an aperture configured for slidable receipt of the needle between the retracted position and the extended position. The binding member includes one or more drag inducing members extending therefrom, such that the one or more drag inducing members engage the needle during slidable receipt of the needle to create a drag force with the needle. The drag force causes rotation of the binding member relative to a longitudinal axis of the needle such that the binding surfaces engage the needle to prevent slidable movement of the needle in the extended position of the shield. The binding member further includes a retainer extending therefrom such that the retainer is engageable with the needle to prevent rotation of the binding member. The shield further includes a hub retainer being configured to engage a catheter hub.

In another embodiment, the binding member includes separate frictional members that are disposed on a proximal side and a distal side of the binding member. The friction members allow sliding of the needle therewith and provide a frictional drag similar to the drag inducing members. The drag force causes rotation of the binding member relative to a longitudinal axis of the needle such that the binding surfaces engage the needle to prevent slidable movement of the needle in the extended position of the shield. Alternatively, the friction members may form a monolithic member that joins two members. The members engage the needle and binding member to prevent axial movement of the needle.

BRIEF DESCRIPTION OF THE DRAWINGS

The foregoing and other features and advantages of the present invention will be more fully understood from the following detailed description of the exemplary embodiments, taken in conjunction with the accompanying drawings in which.

DETAILED DESCRIPTION OF THE EXEMPLARY EMBODIMENTS

Figure 1:
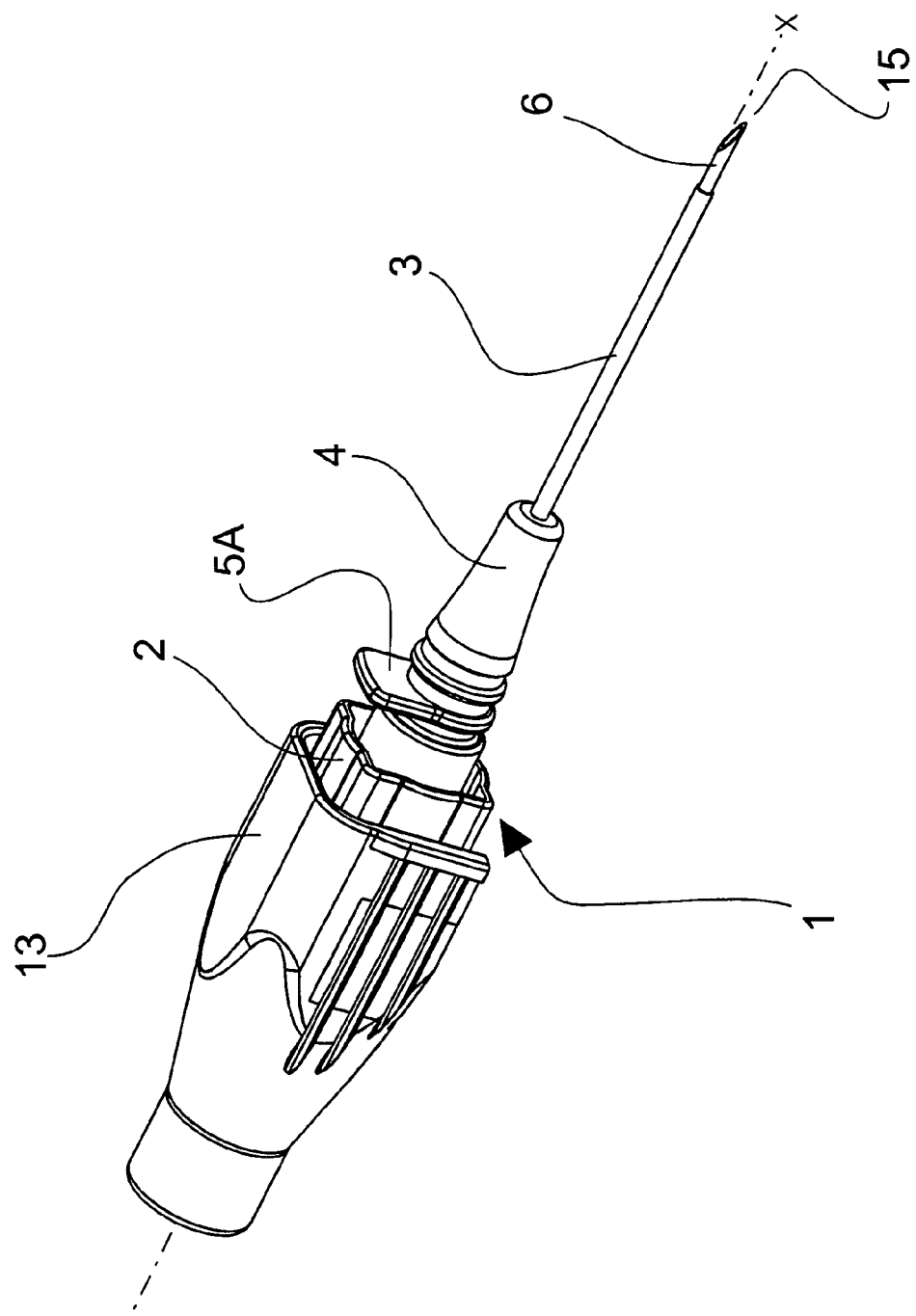
FIG. 1 is a perspective view of one particular embodiment of a medical needle shield apparatus in accordance with the principles of the present invention.

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to a needle tip, including, for example, inadvertent needle sticks. It is contemplated that the medical needle safety shield apparatus may be utilized for medical needle applications including, but not limited to, fluid infusion, fluid collection, catheters, catheter introducers, guidewire introducers, spinal and epidural, biopsy, aphaeresis, dialysis, blood donor, Veress needles, Huber needles, winged ("butterfly") needles, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, like components are designated by like reference numerals throughout the several views. Referring initially to FIGS. 1-10, there is illustrated a medical needle shield apparatus, constructed in accordance with the principals of the present disclosure. The medical needle shield apparatus includes a shield 1 being extensible from a retracted position (FIG. 1) to an extended position (FIG. 10) to enclose a distal end 15 of a needle 6. A binding member 5 is disposed within shield 1 and defines binding surfaces 22. Binding surfaces 22 form an aperture 21 that is configured for receipt of needle 6.

Binding member 5 includes one or more drag inducing members, such as, for example, friction members 26 that extend therefrom. Friction members 26 engage needle 6 to facilitate rotation, as will be discussed, of binding member 5 relative to a longitudinal axis x of needle 6. Binding member 5 also includes a retainer 14 extending therefrom. Retainer 14 has a first portion, such as, for example, a needle communicating surface 23 that engages needle 6 to prevent rotation of binding member 5 prior to the extended position.

Retainer 14 also has a second portion, such as, for example, a hub retainer 14A. A catheter hub 4 is disposed about needle 6. Catheter hub 4 is releasably mounted with shield 1 via releasable engagement with hub retainer 14A. The medical needle shield apparatus is advantageously configured to prevent hazardous exposure to distal end 15 of needle cannula 6, as will be discussed below.

The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

A catheter 3 includes catheter hub 4, which forms part of a catheter 3 and introducer assembly that may be employed with the medical needle shield apparatus. Shield 1 and catheter 3 slidably support needle 6 for use thereof. A handle 13 is mounted with needle 6 to facilitate manipulation thereof. The term catheter may also be used to describe the outer needle, sleeve, or tube of a medical needle assembly. The term needle may also be used to describe the inner needle, wire, or stylet, which is generally metallic, but may be made of any suitable material including polymers.

Catheter hub 4 has a hub slot 24 for receipt and engagement with hub retainer 14A. Catheter hub 4 has a finger tab 5A for urging catheter 3 toward distal end 15 of needle 6, facilitating removal of catheter 3 from shield 1, and use during a catheter application. It is contemplated that finger tab 5A may be alternatively configured and dimensioned according to the needle application or disposed on shield 1.

Figure 2:
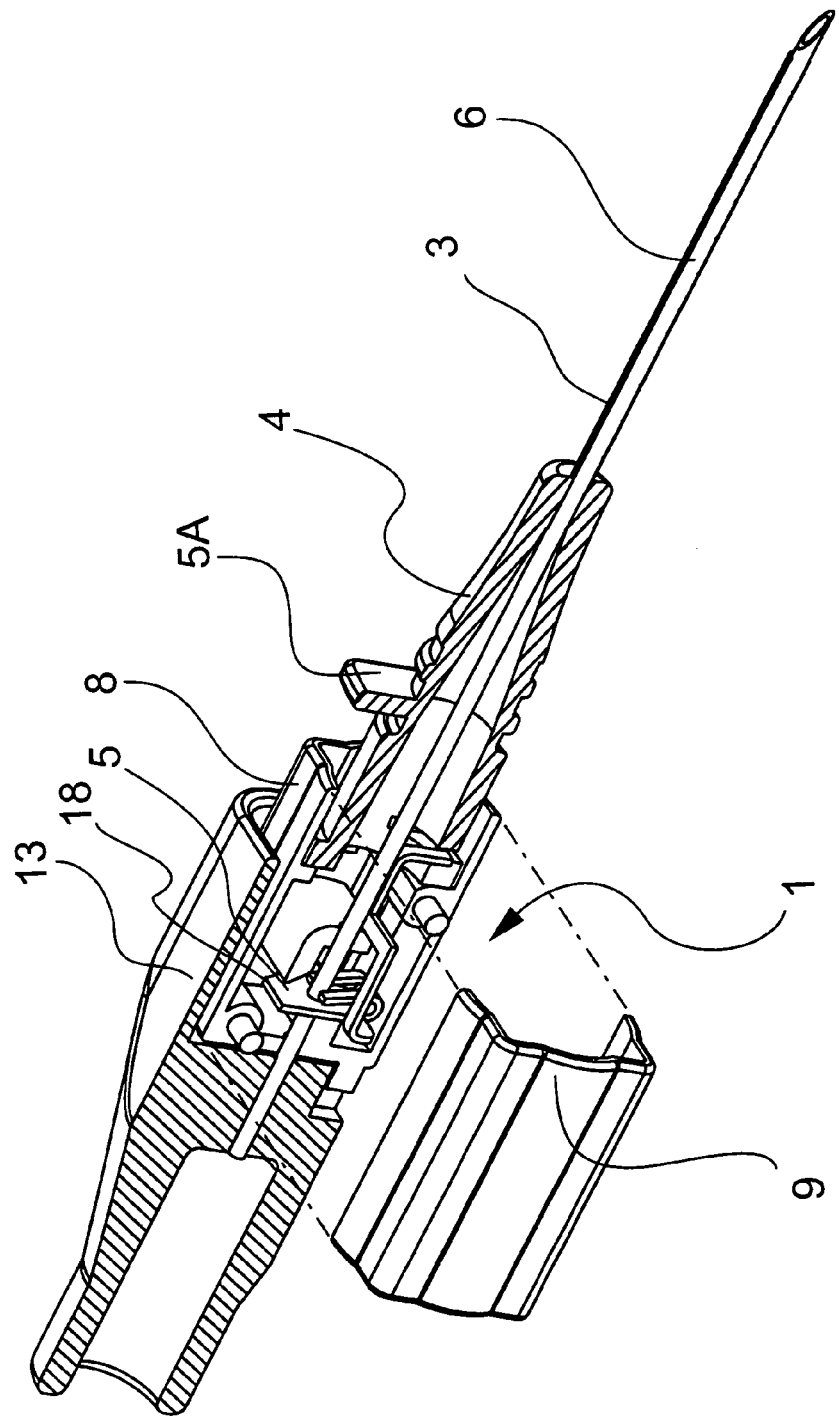
FIG. 2 is a cross-sectional perspective view of the medical needle shield apparatus shown in FIG. 1 with a housing section separated therefrom.

Shield 1 includes a housing 2 for disposition of binding member 5. Shield 1 includes housing first section 8 and housing second section 9, as shown in FIG. 2. It is envisioned that housing sections 8, 9 may be variously configured and dimensioned such as, for example, rectangular, spherical, etc. It is further envisioned that housing sections 8, 9 may be joined by any appropriate process such as, for example, snap fit, adhesive, solvent weld, thermal weld, ultrasonic weld, screw, rivet, etc. Alternatively, housing 2 may be monolithically formed or integrally assembled of multiple sections and may be substantially transparent, opaque, etc. Housing sections 8, 9 may include ribs, ridges, etc. to facilitate manipulation of the medical needle shield apparatus.

Figure 3:
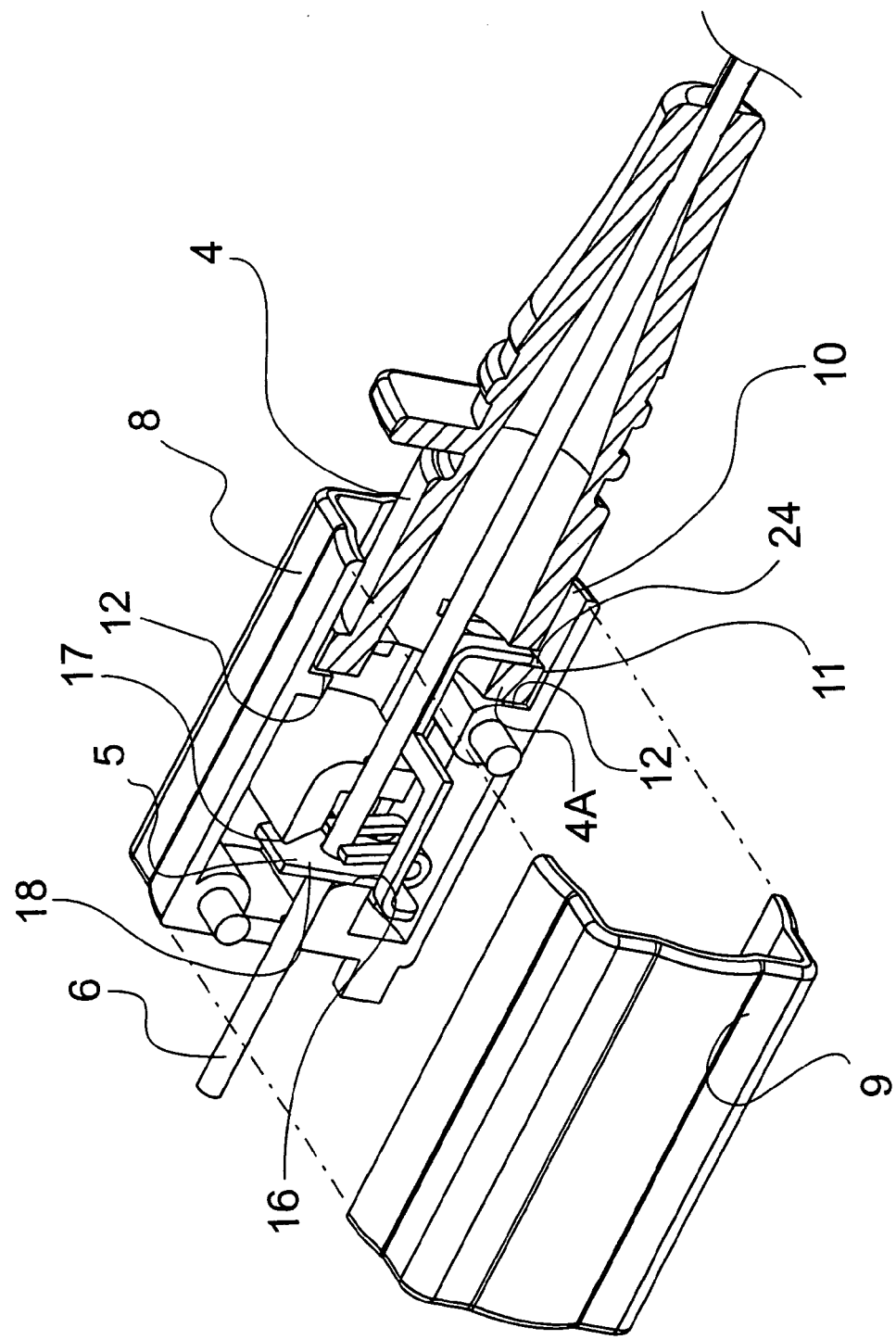
FIG. 3 is an enlarged perspective cutaway view of the medical needle shield apparatus shown in FIG. 2.

Referring to FIG. 3, a flange 4A of catheter hub 4 is concentrically supported by a control surface 10 disposed about an inner surface of housing 2. Control surface 10 engages an outer surface 11 of flange 4A for guiding and supporting the extension of catheter hub 4 therefrom. It is contemplated that control surface 10 may engage other portions of catheter hub 4.

Housing 2 may include hub stop surfaces 12 that facilitate positioning of catheter hub 4 with housing 2. Hub stop surfaces 12 prevent proximal movement of catheter hub 4 during mounting with and relative to housing 2. Hub stop surfaces 12 advantageously facilitates control of the degree of insertion with housing 2 according to the requirements of a particular catheter application. One or a plurality of hub stop surfaces 12 may be employed. It is contemplated that hub stop surfaces 12 may include springs, clips, etc. to facilitate attachment with catheter hub 4.

Referring to FIGS. 4-9, binding member 5 is monolithically formed and includes an aperture plate 18, frictional members 26, and retainer 14, which includes end sensing member 19, needle communicating surface 23 and hub retainer 14A. Aperture plate 18 has a rectangular, generally planar configuration with sufficient stiffness to produce forces for binding needle 6, as will be discussed. It is envisioned that aperture plate 18 may have an arcuate surface, undulating, etc. It is further envisioned that aperture plate 18 may have various degrees of stiffness according to the requirements of a particular application.

Frictional members 26 may be monolithically formed with binding member 5 and extend from aperture plate 18 in association therewith for alignment with aperture 21 and engagement with needle 6. Each frictional member 26 includes a flexible arm 26A, which are spaced apart to facilitate sliding engagement with needle 6. Such engagement creates a frictional drag force with needle 6. This frictional drag force causes binding member 5 to move with needle 6, which generates a canting force in retainer 14 and inclination of aperture plate 18, discussed below. The canting force and inclination urge rotation of binding member 5. It is contemplated that a single friction member may be employed.

As facilitated by movement of needle 6, the canting force causes a lever or moment of retainer 14, which is opposed to prevent rotation of binding member 5. The canting force is opposed by engagement of needle communicating surface 23 with needle 6 in a non-binding or sliding orientation of binding member 5. As can be readily appreciated by one skilled in the art from the disclosure herein, retainer 14 is an example of retainer means for preventing inclination of the binding member.

End sensing member 19 extends distally from aperture plate 18. End sensing member 19 may be perpendicularly oriented relative to a plane defined by aperture plate 18. This perpendicular orientation facilitates inclination of aperture plate 18 for disposal in a binding or non-binding orientation of binding member 5. It is envisioned that end sensing member 19 may be variously oriented with aperture plate 18 and may flexibly extend therefrom.

Figure 5:
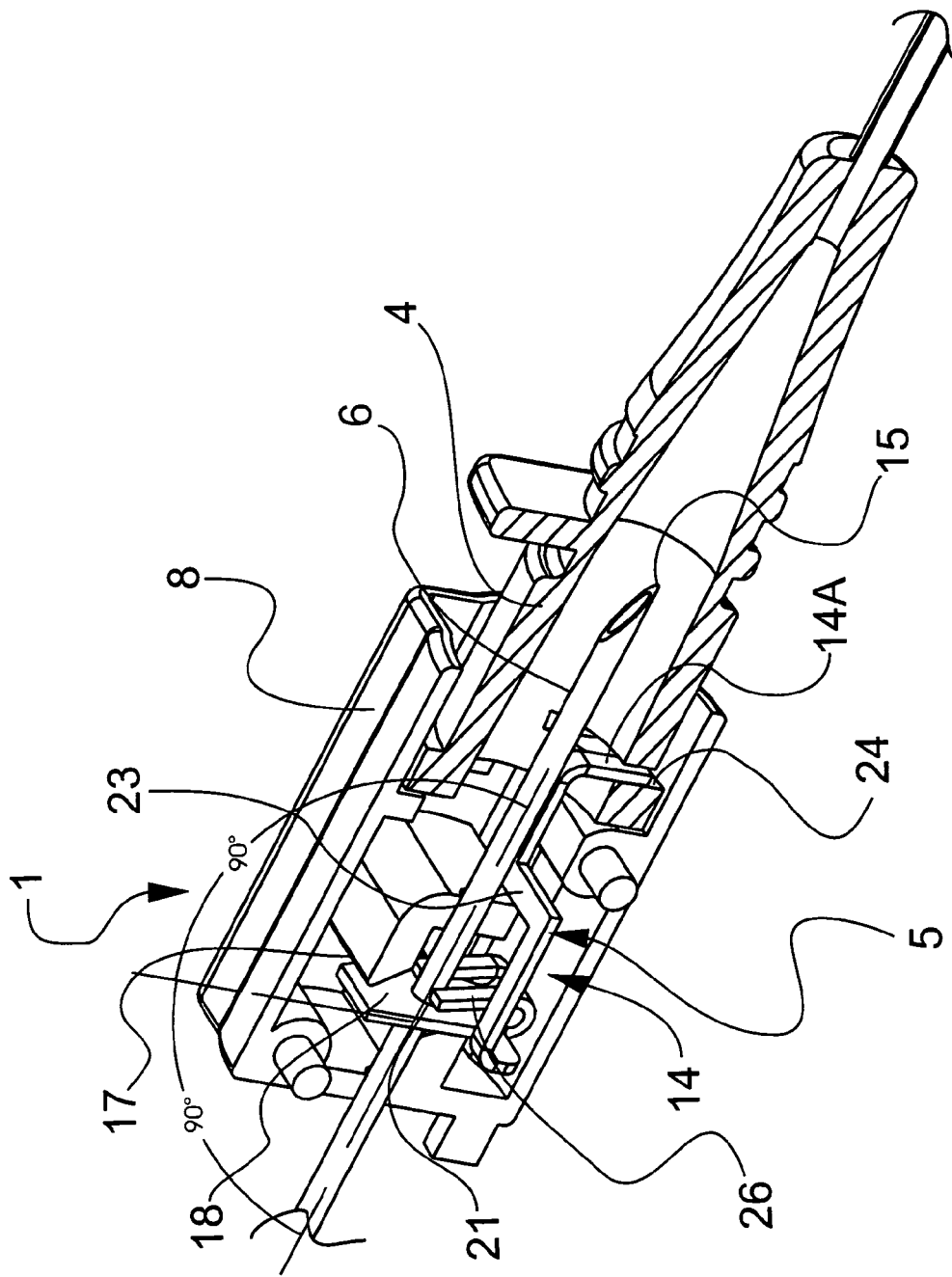
FIG. 5 is a cross-sectional perspective view of the medical needle shield apparatus shown in FIG. 2 having a shield thereof extended.

Needle communicating surface 23 extends from end sensing member 19 in a substantially perpendicular orientation to aperture plate 18 and in alignment with needle 6. In a non-binding or sliding orientation, needle communicating surface 23 extends in substantially parallel alignment with needle 6 for slidable engagement therewith, as shown in FIG. 5. Needle communicating surface 23 engages needle 6 and maintains the non-binding or sliding orientation of aperture plate 18 by opposing the canting force of end sensing member 19 directed to needle 6. The canting force, as created by the drag force described below, is generated by friction members 26 engaging aperture plate 18, and in cooperation with blocking member 16, causing aperture plate 18 to move to a binding position. Inclination, however, is prevented in the non-binding or sliding orientation because of the engagement of needle communicating surface 23 with needle 6, as shown in FIG. 5. As needle 6 is retracted proximally and shield is extended distally, needle 6 continues to slideably engage needle communicating surface 23, as shown in FIG. 5.

A drag force is created between friction members 26 and needle 6. The drag force in conjunction with blocking member 16, cause aperture plate 18 to move to the binding position. Note that the force created by blocking member 16 acts in a direction opposite of the drag force. This causes a force couple which moves the aperture plate 18 to the binding position. As needle 6 is released from engagement with needle communicating surface 23, aperture plate 18 and retainer 14 move to the binding position. Rotation is no longer opposed by engagement with needle 6 at needle communicating surface 23. Thus, aperture plate 18, attached to retainer 14, is subject to inclination into a binding orientation. Rotation of aperture plate 18 causes binding surfaces 22 to frictionally engage needle 6 to prevent movement thereof. Blocking members 16, 17 cause aperture plate 18 to move to the binding position as forces are imposed on shield 1 in either direction along longitudinal axis x. This maintains needle 6 within shield 1 to avoid hazardous exposure to distal end 15. It is envisioned that needle communicating surface 23 may include ribs, projections, cavities, etc. for engagement with needle 6 or that a portion of needle communicating surface 23 engages needle 6.

It is also envisioned that binding member 5 may be configured such that aperture 21 does not engage needle 6 until binding occurs. In this embodiment, blocking members 16 and 17 are configured to initiate rotation of binding member 5 upon which the rotation of aperture plate 18 causes binding surfaces 22 to frictionally engage needle 6 to prevent movement thereof.

Hub retainer 14A extends transversely from a distal end of needle communicating surface 23. Hub retainer 14A extends a sufficient length for corresponding receipt within a hub slot 24 of catheter hub 4, as shown in FIG. 5. In association with a non-binding or sliding orientation of binding member 5, hub retainer 14A engages catheter hub 4, in hub slot 24, for releasably mounting with housing 2 of shield 1. As can be readily appreciated by one skilled in the art from the disclosure herein, hub retainer 14A is an example of hub retainer means for releasably engaging a catheter hub.

Figure 7:
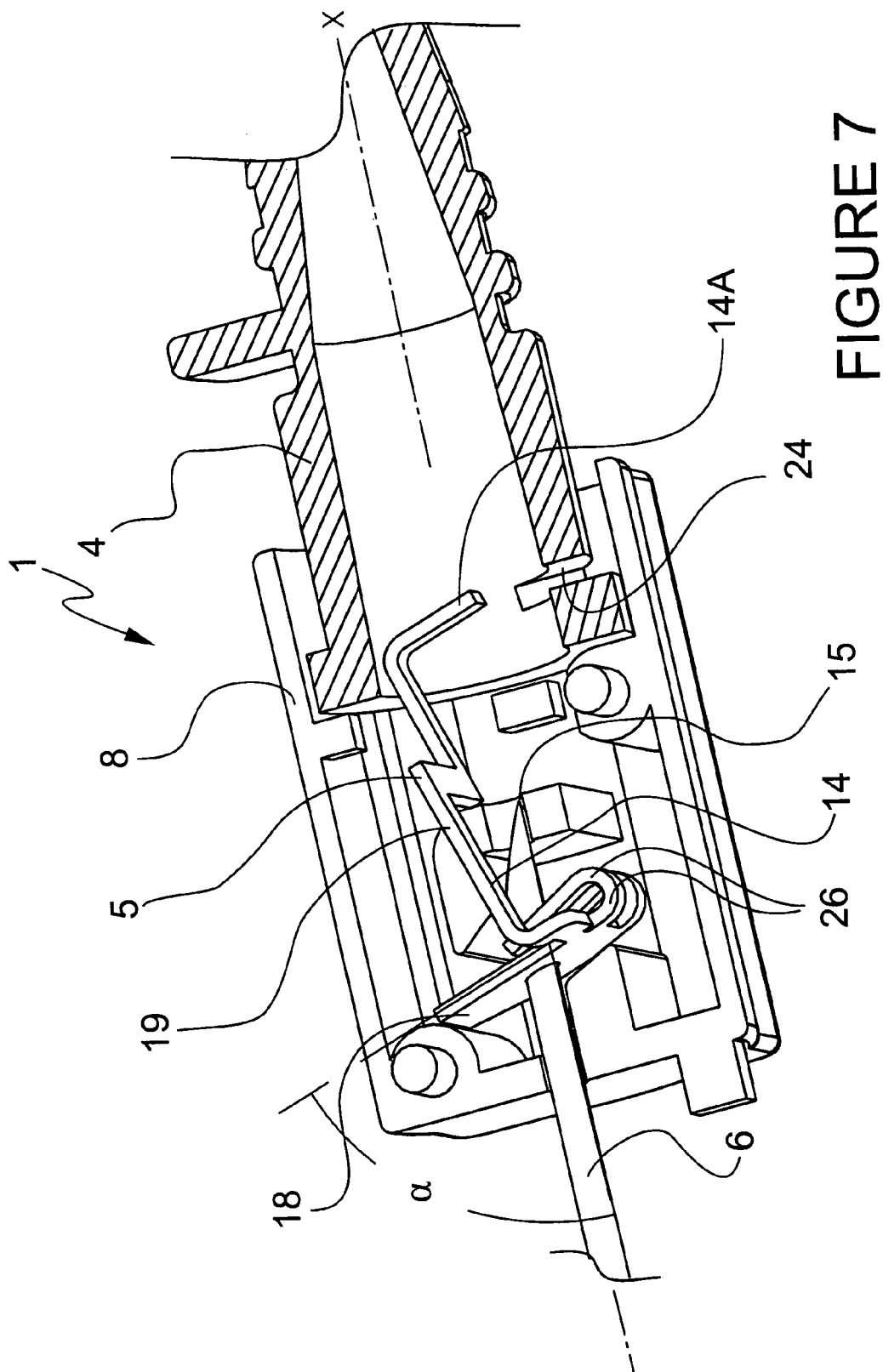
FIG. 7 is an alternative cross-sectional perspective cutaway view of the medical needle shield apparatus shown in FIG. 3.
Figure 8:
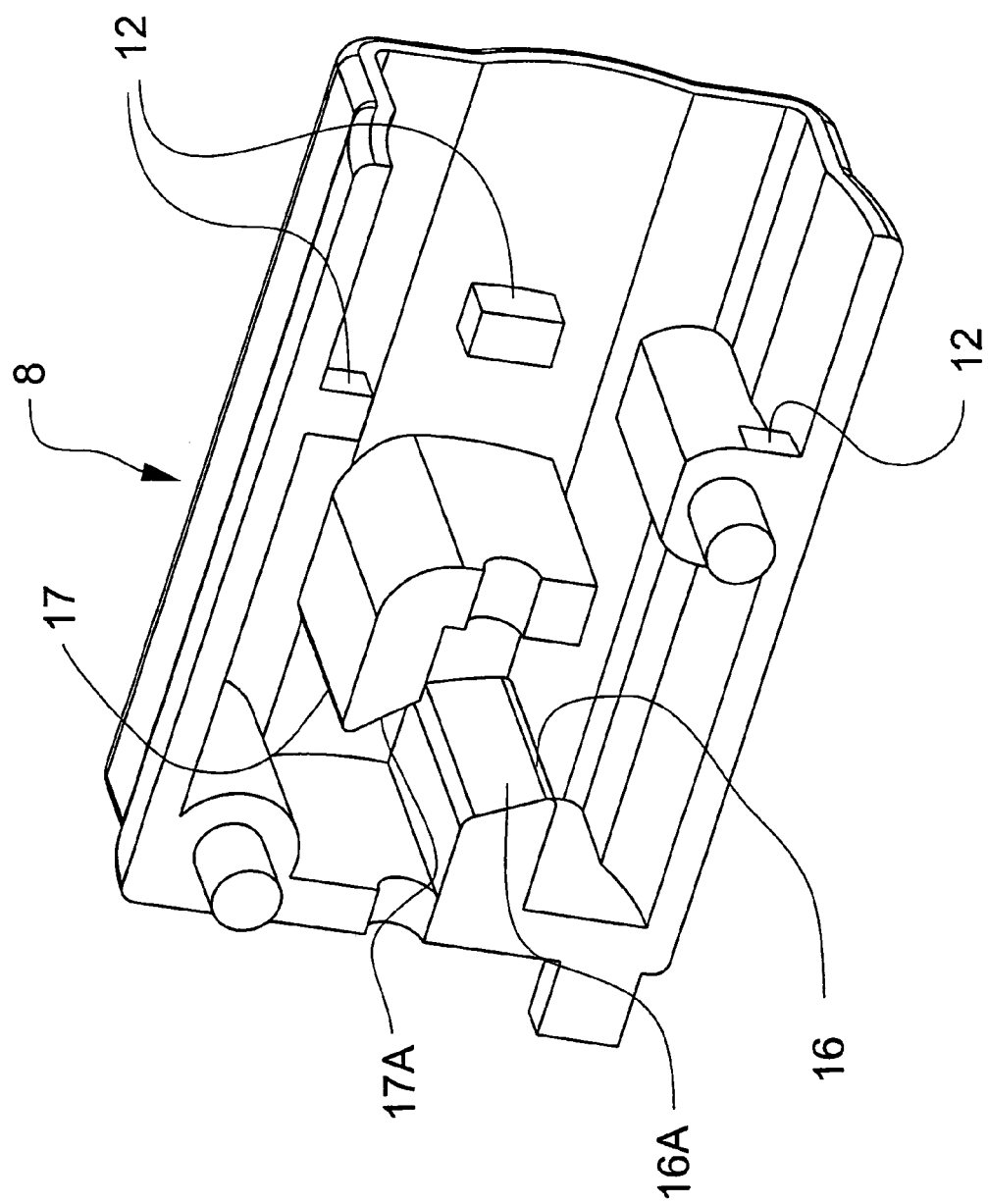
FIG. 8 is a perspective view of an inner surface of a housing section of the medical needle shield apparatus shown in FIG. 3.

As needle 6 is retracted in a proximal direction and shield 1 is extended in a distal direction, as shown in FIG. 7, retainer 14 rotates direction relative to longitudinal axis x due to the canting forces generated by friction members 26. Hub retainer 14A disengages from hub slot 24 to release catheter hub 4 from housing 2. A clinician may manipulate finger tab 5A to manipulate catheter 3 distally and apart from shield 1. It is contemplated that hub retainer 14A may be variously oriented from needle communicating surface 23. It is further contemplated that hub slot 24 may be variously dimensioned and disposed on the circumference of catheter hub 4. Hub slot 24 may include tabs, etc. for retention with hub retainer 14A.

Aperture 21 is formed within aperture plate 18 for slideable engagement with needle 6 during movement between the retracted position and the extended position of shield 1. Aperture 21 includes binding surfaces 22 formed on opposing sides of aperture 21 that engage needle 6 to prevent movement thereof in the extended position of shield 1. As can be readily appreciated by one skilled in the art from the disclosure herein, binding surfaces 22 are an example of binding surface means for engaging the needle 6 to prevent slidable movement of the needle in the extended position of the shield 1. It is contemplated that engagement to prevent movement of needle 6 may include penetrating, frictional, interference, etc. It is envisioned that aperture 21 may have various geometric configurations, such as radial, polygonal, etc. It is further envisioned that aperture 21 may define an open cavity within aperture plate 18, such as, for example, "U" shaped and open to one or a plurality of edges of aperture plate 18.

Figure 4:
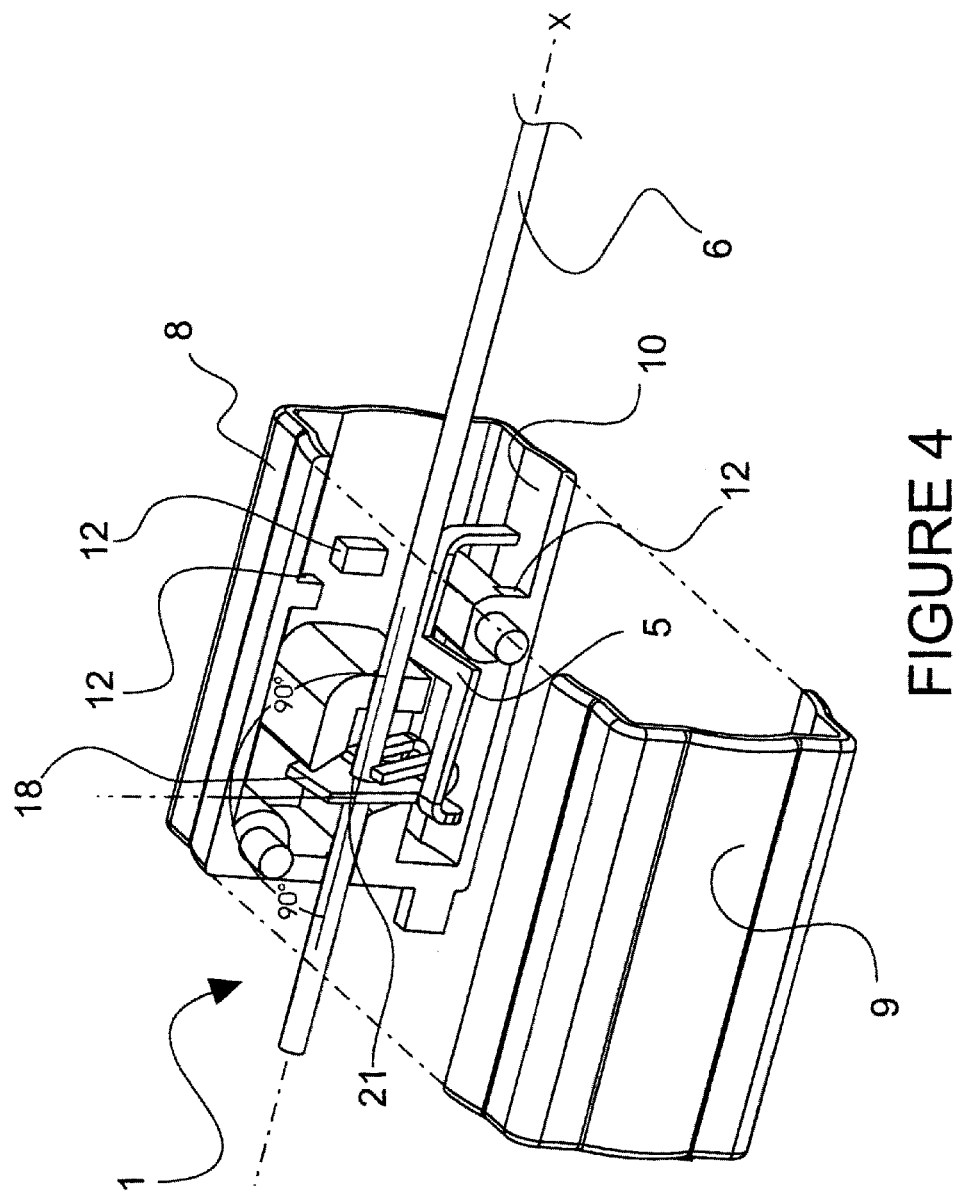
FIG. 4 is a perspective cutaway view of the medical needle shield apparatus shown in FIG. 3.

The inclination of aperture plate 18 relative to longitudinal axis x facilitates sliding and binding, via binding surfaces 22 of aperture 21, of needle 6 within shield 1 to prevent hazardous exposure to distal end 15. For example, as shown in FIG. 4, aperture plate 18 is oriented at an angle of approximately 90° relative to longitudinal axis x such that aperture plate 18 is disposed substantially perpendicular to needle 6. In this non-binding or sliding orientation, needle 6 is free to slide within aperture 21. Referring to FIG. 5, as needle 6 is retracted and shield 1 is extended, needle 6 continues to engage needle communicating surface 23 and aperture plate 18 maintains its perpendicular orientation relative to longitudinal axis x.

Figure 9:
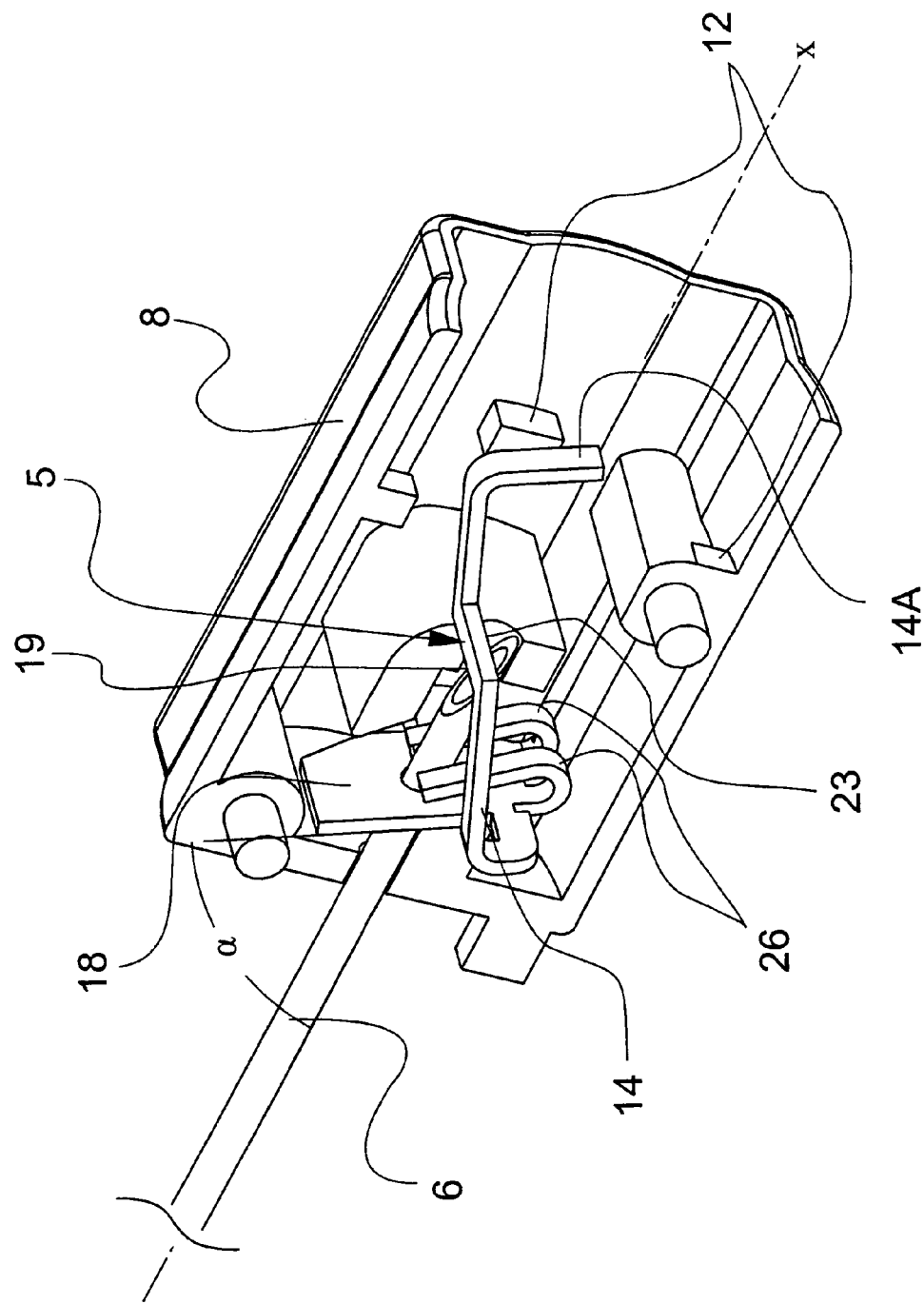
FIG. 9 is a perspective cutaway view of the medical needle shield apparatus shown in FIG. 3 with the shield in an extended position.

Referring to FIGS. 7 and 9, shield 1 is manipulated such that friction members 26 cause binding member 5 to rotate relative to longitudinal axis x. Aperture plate 18 rotates out of perpendicular alignment with needle 6 such that aperture plate is oriented at an angle α, which is less than 90° with respect to longitudinal axis x. It is contemplated that angle α may be measured from either side of aperture plate 18.

Aperture plate 18 rotates to angle α and binding member 5 approaches a binding orientation. The binding orientation includes engagement of binding surfaces 22 with needle 6 due to the binding orientation of aperture plate 18. This engagement creates binding frictional forces on needle 6, to prevent movement of needle 6 relative to shield 1 and to maintain distal end 15 within shield 1 to prevent hazardous exposure thereto.

Inclination of binding member 5 is also affected by blocking members 16, 17 of housing 2. Blocking members 16, 17 are formed with housing section 8 and are disposed not to interfere with needle 6. Blocking members 16, 17 define surfaces 16A, 17A respectively, that facilitate disposal of aperture plate 18 in a binding orientation.

For example, as shown in FIG. 2, shield 1 is in a retracted position and needle 6 is fully extended. Binding member 5 and aperture plate 18 are in a non-binding or sliding orientation such that aperture plate 18 is substantially perpendicular to longitudinal axis x. Blocking members 16, 17 may engage aperture plate 18 to maintain aperture plate 18 in the perpendicular orientation. Blocking members 16, 17 may also maintain such orientation during extension of needle 6 or may not engage needle 6.

As needle 6 is retracted and shield 1 is extended, friction members 26 create a drag force via engagement with needle 6 on binding member 5, as shown in FIG. 7 causing aperture plate 18 to rotate to the binding orientation. Blocking member surfaces 16A, 17A engage aperture plate 18 to facilitate rotation thereof from the perpendicular orientation into the binding orientation such that binding surfaces 22 engage needle 6. This configuration prevents movement of needle 6. As can be readily appreciated by one skilled in the art from the disclosure herein, friction members 26 are an example of drag inducing means for facilitating inclination of the binding member 5 relative to a longitudinal axis of the needle 6.

Binding of binding member 5 to needle 6 is facilitated by the friction or binding force generated between binding surfaces 22 and needle 6. This frictional engagement prevents axial movement of needle 6 relative to housing 2 when shield 1 is in the extended position. This configuration advantageously prevents hazardous exposure to needle 6. It is contemplated that binding surfaces 22 may include sharp edges to increase frictional engagement. It is further contemplated that the friction or binding force may be varied by altering factors, such as, for example, aperture 21 dimension, needle 6 diameter, aperture plate 18 thickness, the dimension from blocking members 16, 17 contact point to the centerline of needle 6 and the coefficient of friction between aperture 21 and needle 6 for any force applied to housing 2 up to the point of material failure, etc., depending on the particular requirements of a needle application.

As can be readily appreciated by one skilled in the art from the disclosure herein, binding member 5 is an example of means for binding the shield 1 to the needle 6 in the extended position by enabling the binding means to incline relative to a longitudinal axis of the needle 6 to lock against the needle 6 and for permitting engagement with the needle 6 to prevent inclination and to sense the end of the needle 6 until the shield 1 is in the extended position.

Figure 3A:
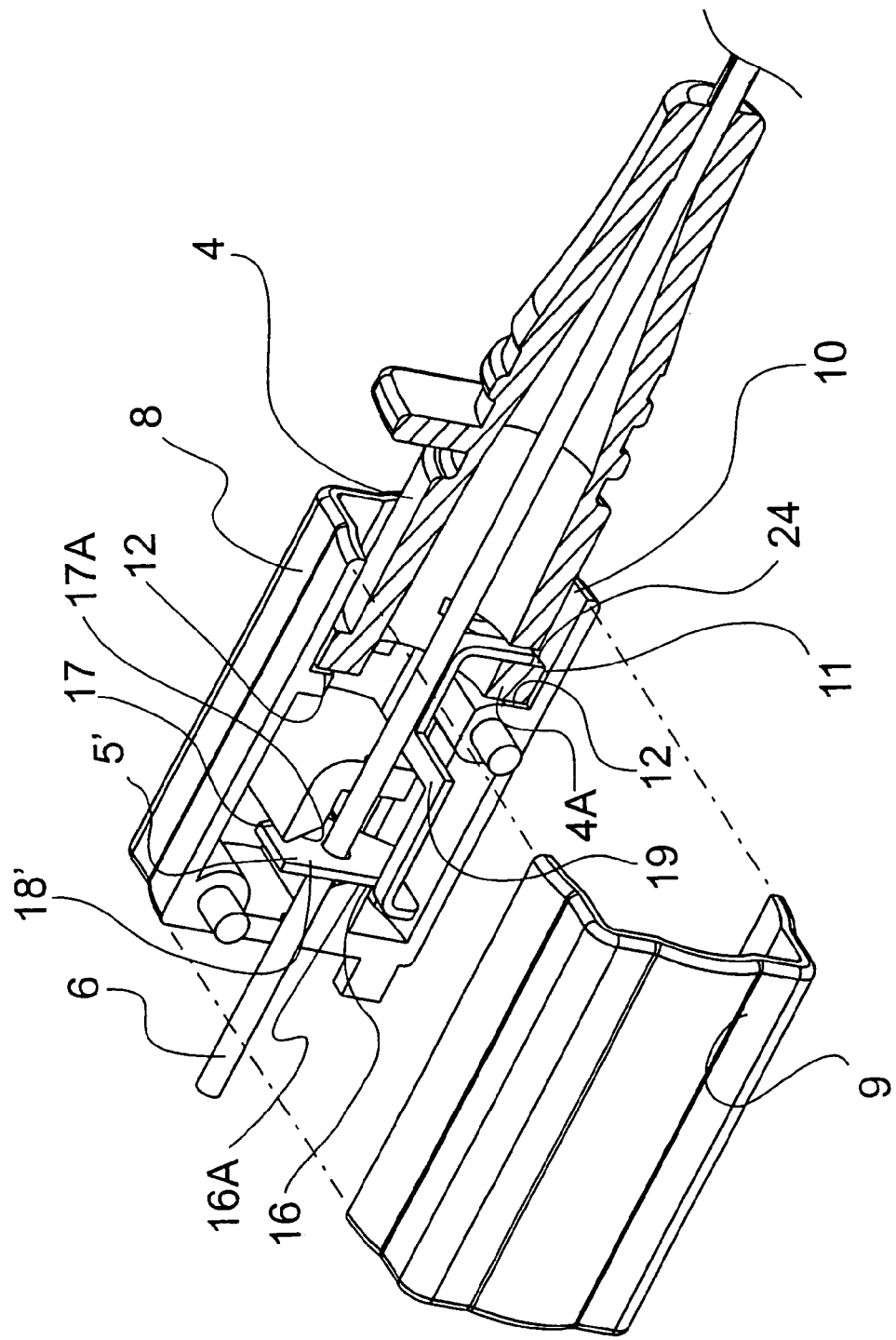
FIG. 3A is an enlarged perspective view of an alternate embodiment of the medical needle shield apparatus shown in FIG. 2.
Figure 6:
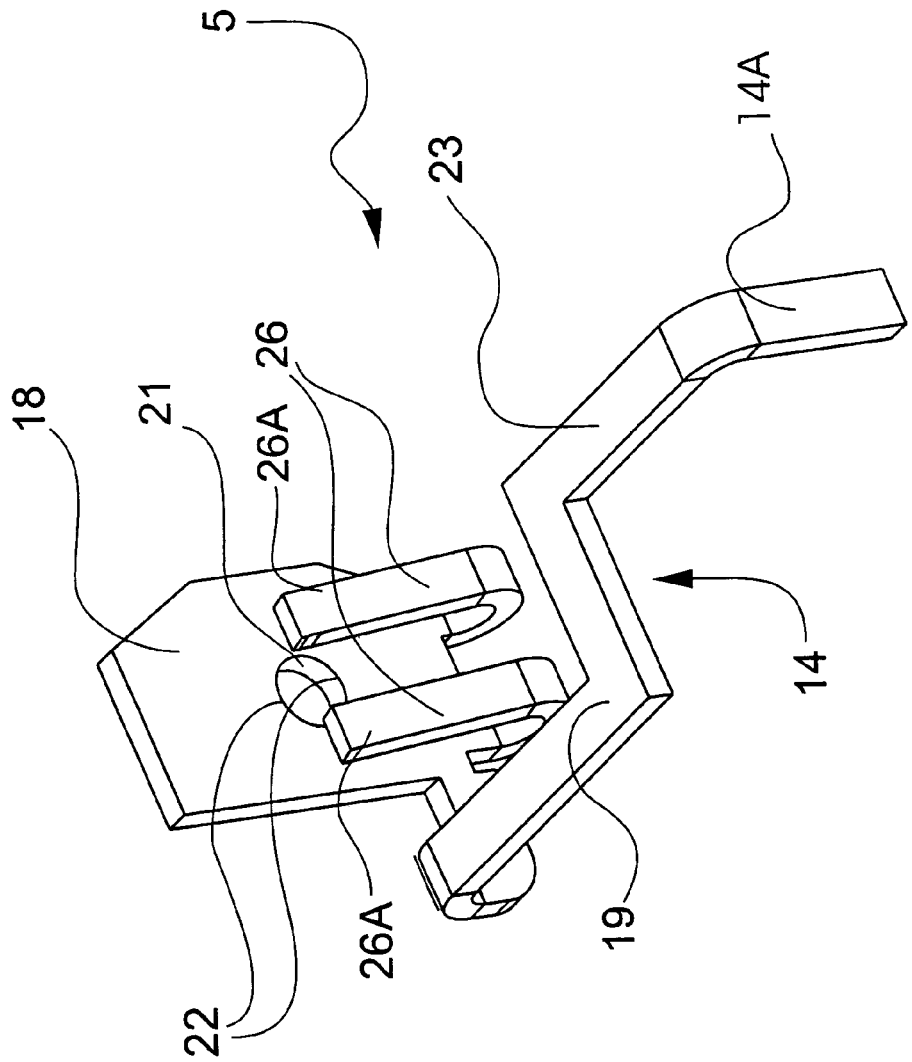
FIG. 6 is an enlarged perspective view of a binding member of the medical needle shield apparatus shown in FIG. 2.

Referring to FIG. 3A, another alternate embodiment of binding member 5' is shown (similar to binding member 5 shown in FIG. 6, but without frictional members 26). Binding member 5' includes a drag inducing member, such as, aperture 21 that is formed by binding surfaces 22 (see FIG. 6). Aperture 21 facilitates sliding engagement with needle cannula 6. Such engagement creates a frictional drag force with needle cannula 6. This frictional drag force causes binding member 5' to move with needle cannula 6. In a non-binding or sliding orientation of binding member 5', aperture plate 18' engages blocking members 16, 17 causing a canting force in end sensing member 19, as discussed.

Figure 3B:
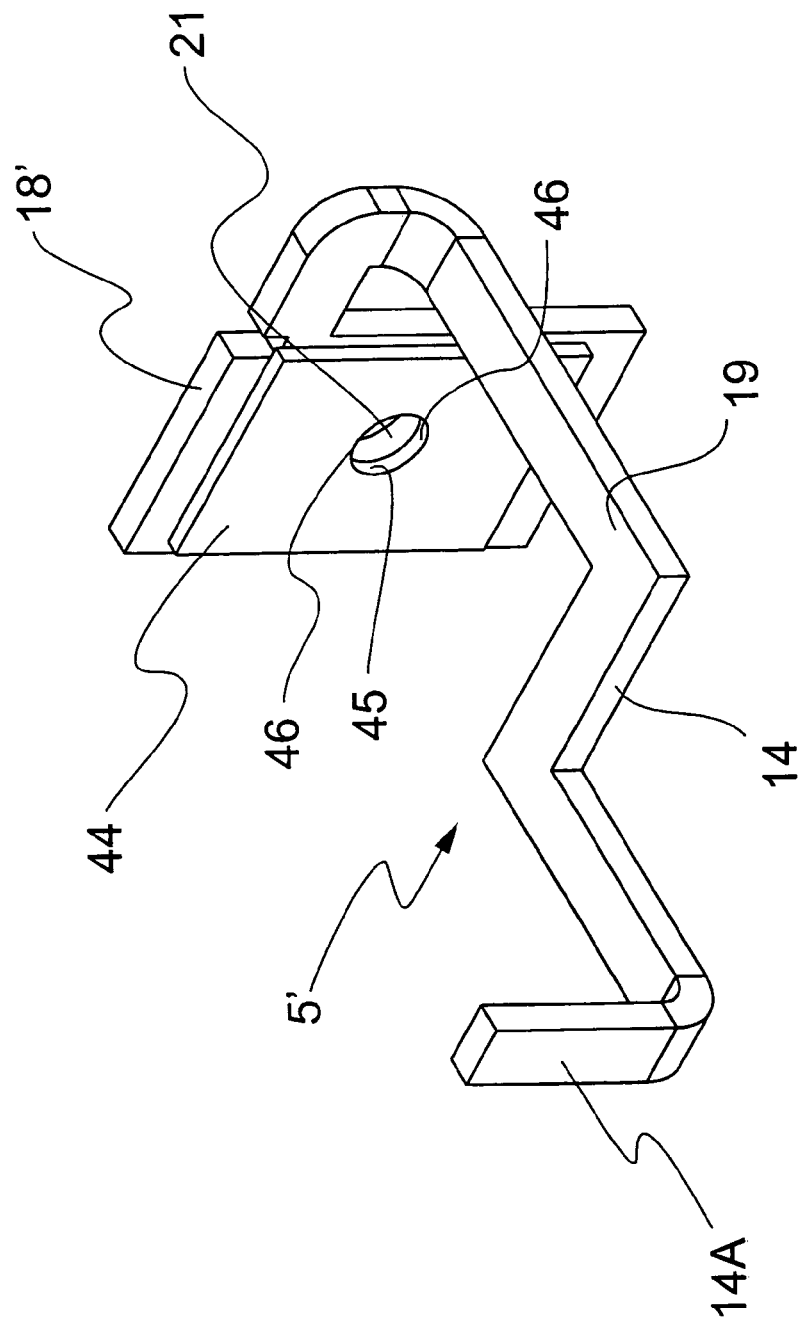
FIG. 3B is an enlarged perspective view of an alternate embodiment of the medical needle shield apparatus shown in FIG. 2.
Figure 3C:
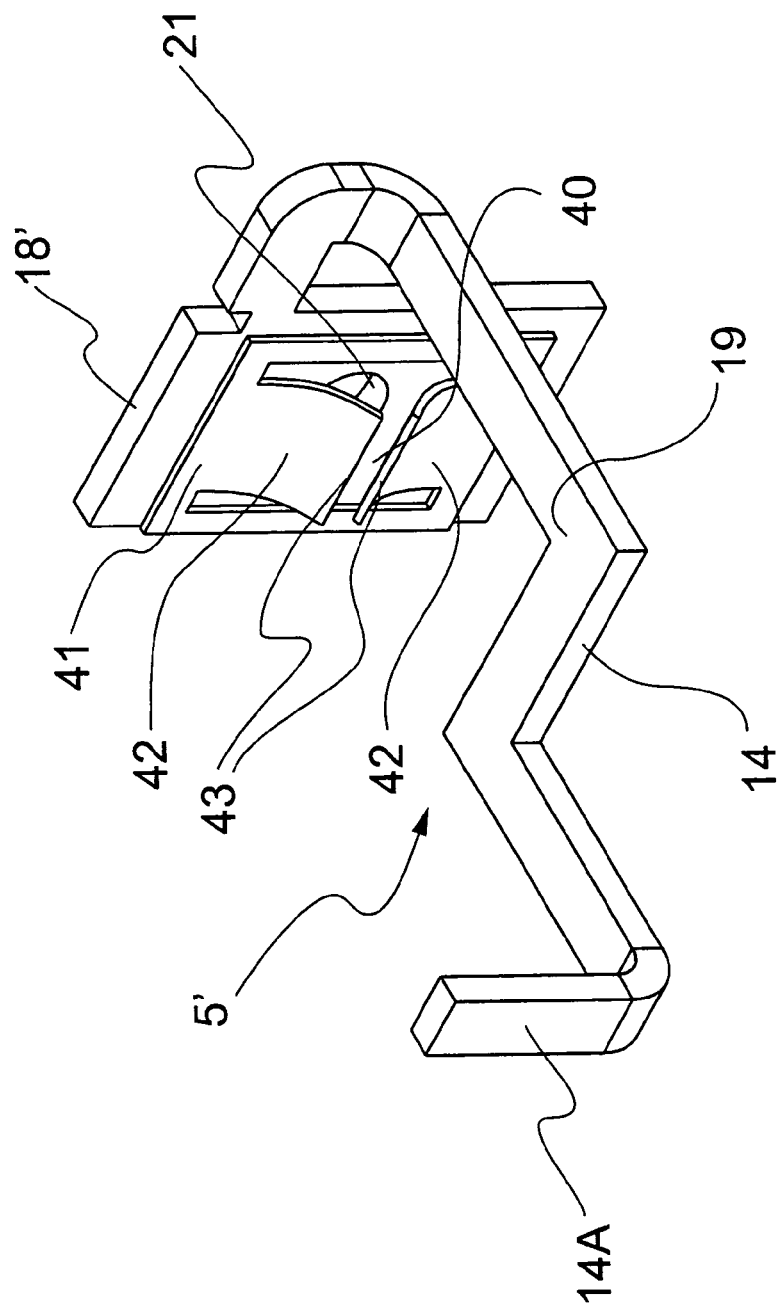
FIG. 3C is an enlarged perspective view of an alternate embodiment of the medical needle shield apparatus shown in FIG. 2.

Referring to FIGS. 3B and 3C, alternate embodiments of binding member 5' are shown. FIG. 3B shows a member 44 having an aperture 45, with member 44 being disposed on aperture plate 18'. The diameter of aperture 45 is smaller than the diameter of aperture 21. Binding member 5' includes a drag inducing member, such as, aperture 45 that is formed by binding surfaces 46. Aperture 45 facilitates sliding engagement with needle cannula 6. Such engagement creates a frictional drag force with needle cannula 6, and in cooperation with blocking member 16, cause aperture plate 18' to move to the binding position. As can be readily appreciated by one skilled in the art from the disclosure herein, aperture 45 is an example of drag inducing means for facilitating inclination of the binding member 5 relative to a longitudinal axis of the needle 6 and binding surfaces 46 are an example of binding surface means for engaging the needle 6 to prevent slidable movement of the needle in the extended position of the shield 1. FIG. 3C shows a member 41 having elements 42 defining an opening 40, with member 41 being disposed on aperture plate 18'. Binding member 5' includes a drag inducing member, such as, opening 40 that is formed by surfaces 43. The distance between surfaces 43 is smaller than the diameter of aperture 21. Surfaces 43 facilitate sliding engagement with needle cannula 6. Such engagement creates a frictional drag force with needle cannula 6, and in cooperation with blocking member 16, cause aperture plate 18' to move to the binding position. It is contemplated that members 41 and 44 may be fabricated from materials such as polymerics, metals, elastomeric materials, etc. As can be readily appreciated by one skilled in the art from the disclosure herein, surfaces 43 are an example of drag means for facilitating inclination of the binding member 5 relative to a longitudinal axis of the needle 6, and each of the alternate embodiments of binding member 5' is an example of means for binding the shield 1 to the needle 6 in the extended position by enabling the binding means to incline relative to a longitudinal axis of the needle 6 to lock against the needle 6 and for permitting engagement with the needle 6 to prevent inclination and to sense the end of the needle 6 until the shield 1 is in the extended position.

Figure 11:
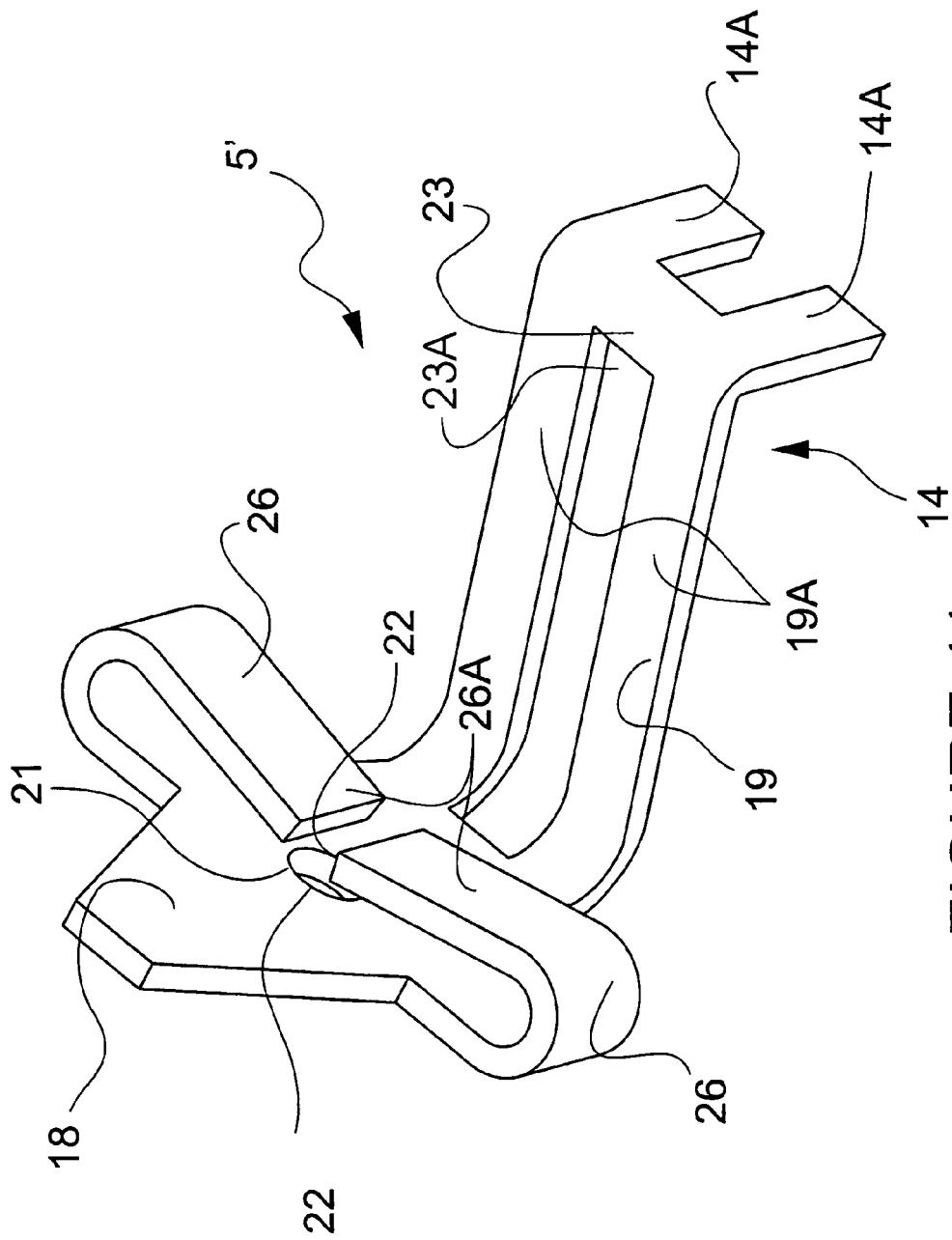
FIG. 11 is an enlarged perspective view of an alternate binding member of the medical needle shield apparatus shown in FIG. 6.
Figure 12:
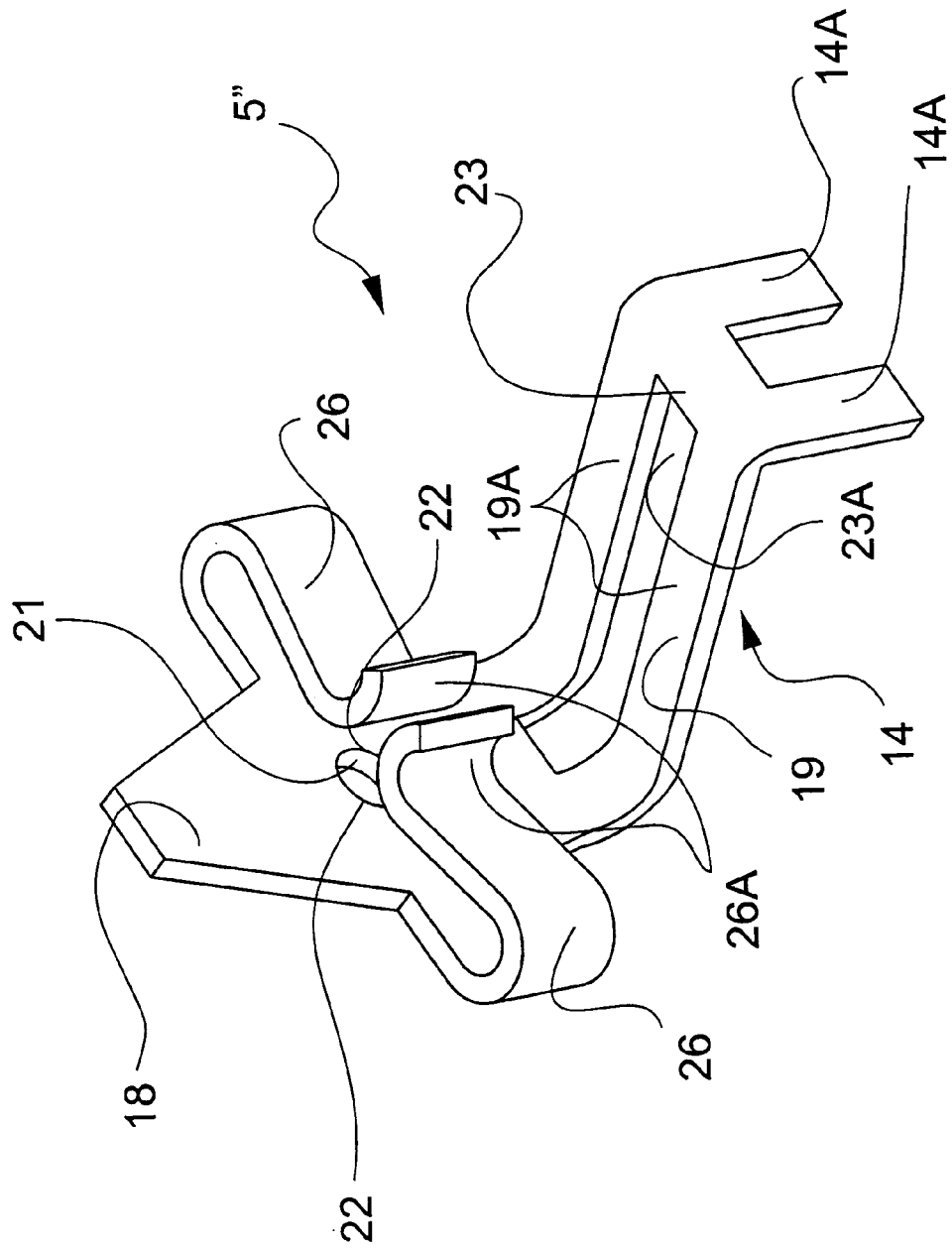
FIG. 12 is an enlarged perspective view of another alternate binding member of the medical needle shield apparatus shown in FIG. 3.

Referring to FIGS. 11 and 12, alternate embodiments of binding member 5 are shown. Aperture plate 18 has a polygonal geometric configuration and end sensing member 19 has member arms 19A that extend in a uniform axial orientation, parallel to needle 6. Needle communicating surface 23 extends transversely to bridge a cavity 23A between arms 19A. Binding member 5 includes hub retainers 14A for engagement with hub slot 24, similar to that described. Friction members 26 extend laterally from aperture plate 18. Friction member arms 26A may include a planar engagement surface, as shown in FIG. 11, or alternatively, may include a curled engagement surface, as shown in FIG. 12, for engagement with needle 6.

In operation, the medical needle shield apparatus, similar to that described in accordance with the principles of the present disclosure is provided for employment with catheter 3. The components of the medical needle shield apparatus are fabricated, properly sterilized and otherwise prepared for storage, shipment and use.

Referring to FIGS. 1 and 2, the clinician (not shown) manipulates handle 13 such that shield 1 is in the retracted position and binding member 5 is in a non-binding or sliding orientation. Needle 6 is fully extended relative to shield 1 such that catheter 3 is disposed about needle 6 and catheter hub 4 is releasably mounted with housing 2. A procedure employing the medical needle shield apparatus with catheter 3 is performed by the clinician to completion.

Needle 6 is retracted proximally such that shield 1 is extended toward the extended position, as shown in FIG. 5. Binding member 5 is in the non-binding or sliding orientation such needle 6 engages needle communicating surface 23 and binding surfaces 22 facilitate sliding through aperture 21, as discussed.

Figure 10:
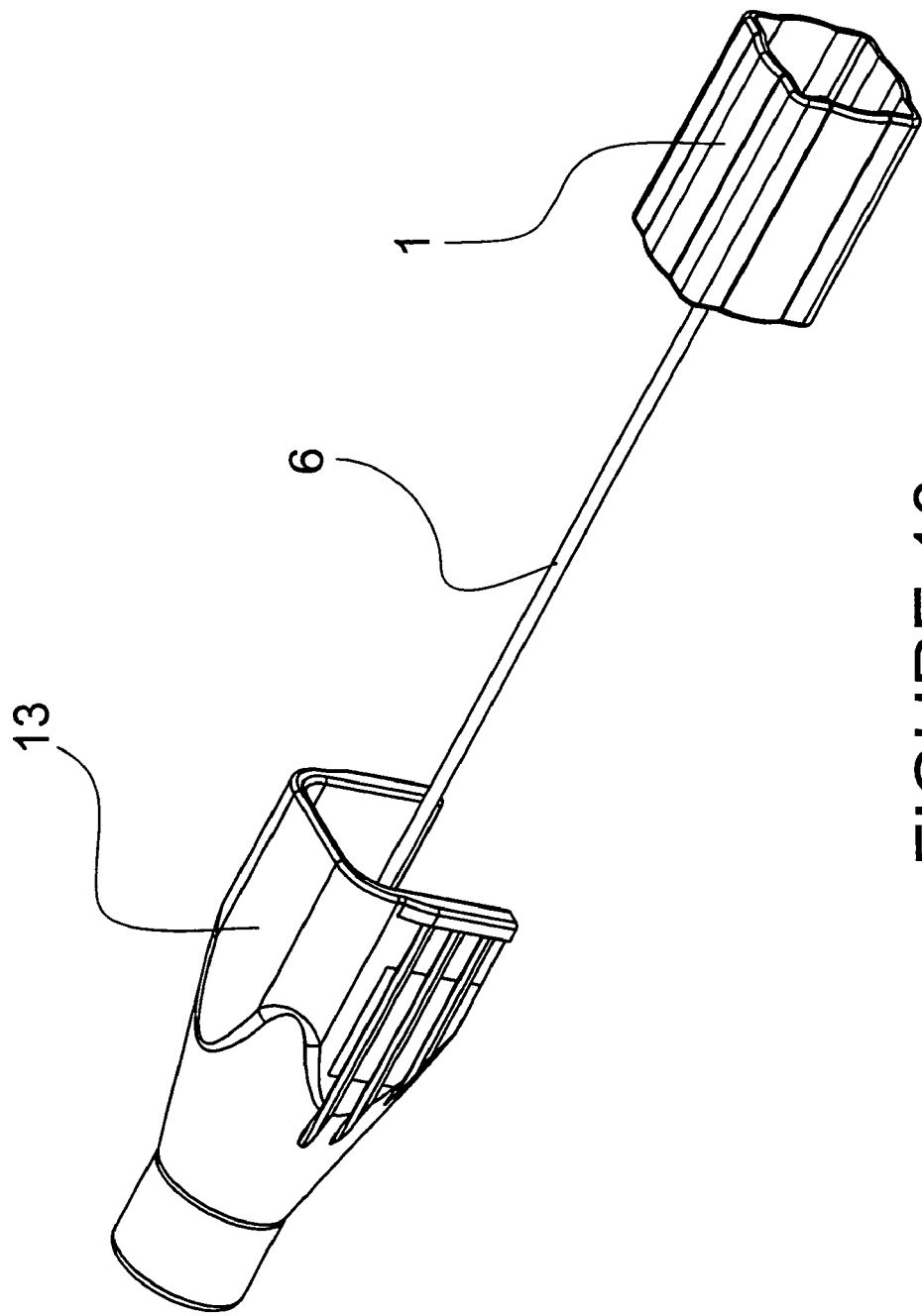
FIG. 10 is a perspective view of the medical needle shield apparatus shown in FIG. 1 with the shield in an extended position.

Referring to FIGS. 7, 9 and 10, as needle 6 clears needle communicating surface 23, retainer 14 is free to rotate due to the canting forces created via the engagement of needle 6 with frictional members 26. Aperture plate 18 rotates relative to longitudinal axis x, from the perpendicular orientation to an inclination for a binding orientation as facilitated by blocking members 16, 17, as shown in FIG. 9. Aperture plate 18 rotates to angle α relative to longitudinal axis x.

Hub retainer 14A disengages from hub slot 24 such that catheter hub 4 is released from housing 2. Catheter 3 can be manipulated distally via finger tab 5A. In the binding orientation, binding surfaces 22 engage needle 6 to bind and prevent axial movement of needle 6 within housing 2. Shield 1 is disposed in the extended position to prevent hazardous exposure to distal end 15, as shown in FIG. 10.

Figure 13:
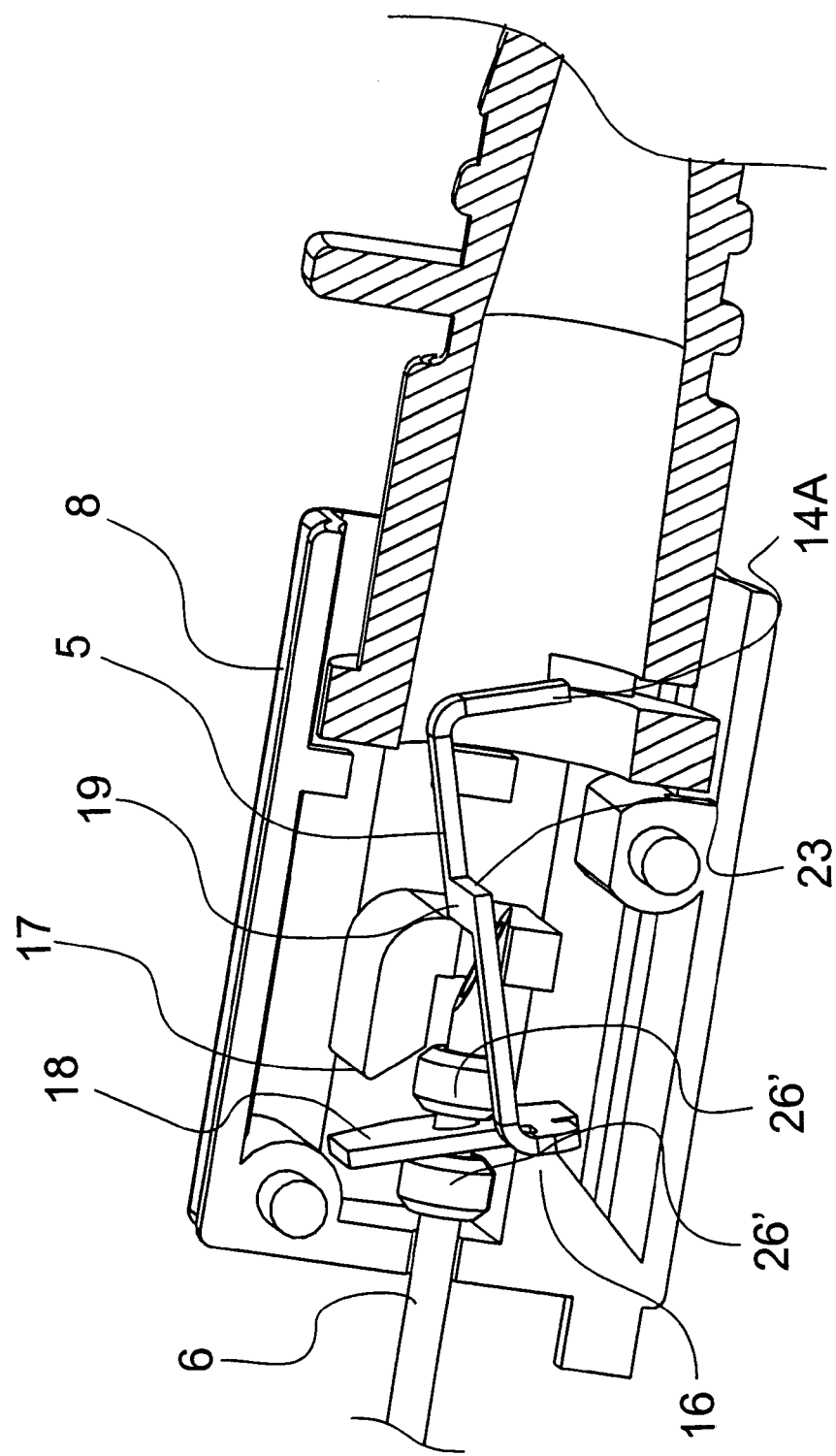
FIG. 13 is an enlarged cross-sectional perspective cutaway view of an alternate embodiment of the medical needle shield apparatus shown in FIG. 1.

In an alternate embodiment, as shown in FIG. 13, binding member 5 includes separate frictional members 26' that are disposed on a proximal side and a distal side of aperture plate 18, respectively. Friction members 26' are friction fit polymer O-rings, which allow sliding of needle 6 therewith and provide a frictional drag force, similar to that discussed, via engagement with needle 6. The drag force is created as needle 6 slides and friction members 26' engage aperture plate 18. Friction members 26' engage aperture plate 18, and in cooperation with blocking member 16, cause aperture plate 18 to move to the binding position. Binding surfaces 22 engage needle 6 to prevent axial movement of needle 6, as discussed. It is contemplated that friction members 26' may be fabricated from materials such as polymerics, metals, etc. As can be readily appreciated by one skilled in the art from the disclosure herein, friction members 26' are an example of drag inducing means for facilitating inclination of the binding member 5 relative to a longitudinal axis of the needle 6.

Figure 14:
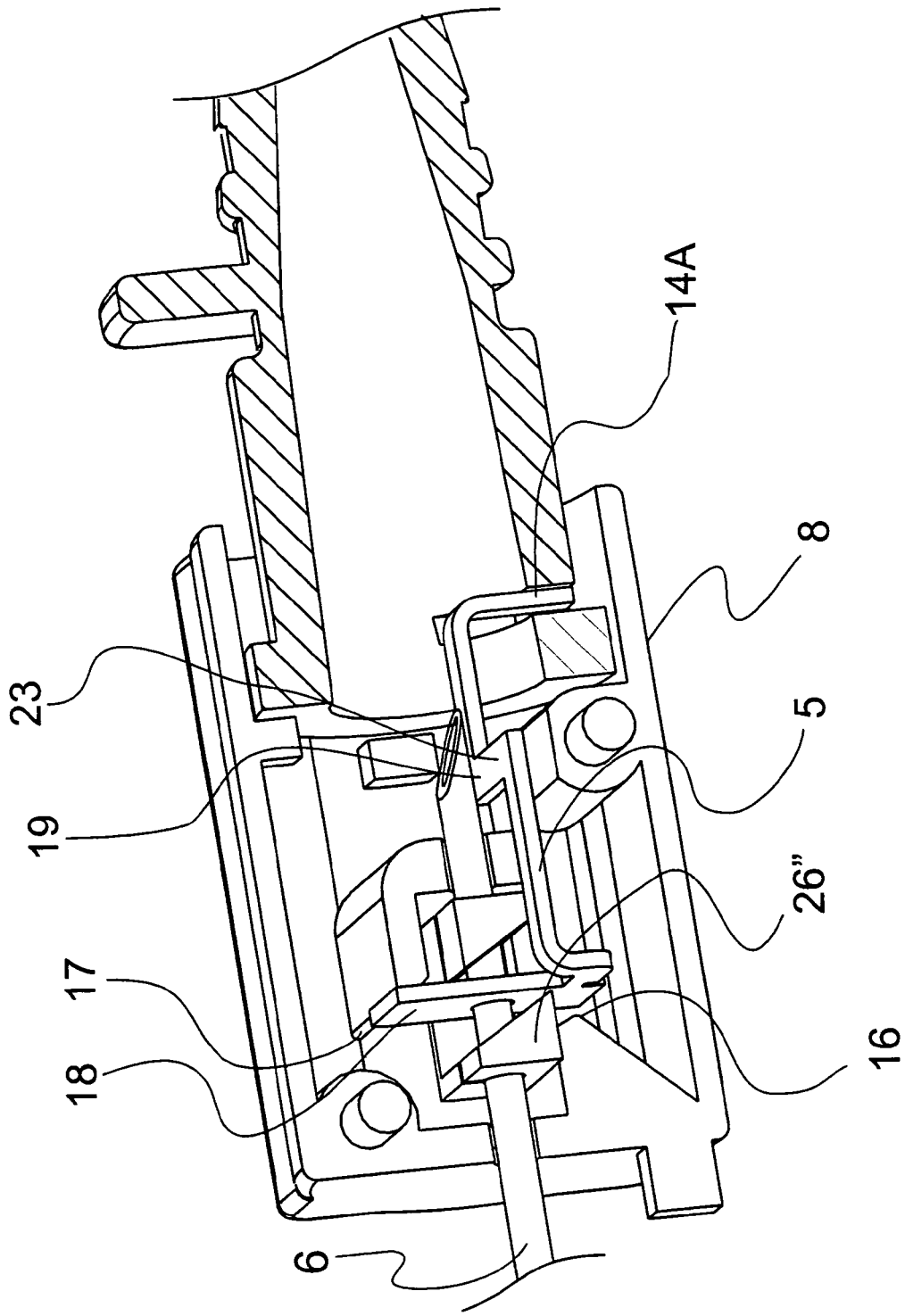
FIG. 14 is an enlarged cross-sectional perspective cutaway view of an alternate embodiment of the medical needle shield apparatus shown in FIG. 1.

Alternatively, friction members 26' may form a monolithic member that links or joins two members 26", as shown in FIG. 14. Members 26" engage needle 6 and aperture plate 18 to prevent axial movement of needle 6, similar to that discussed with regard to FIG. 13. It is envisioned that aperture 21 may create a drag force via engagement with needle 6 to cause rotation of binding member 5, similar to that described. It is further envisioned that materials such as, for example, jells, greases, etc. may be employed to create a frictional drag force with needle 6 to cause rotation of binding member 5. As can be readily appreciated by one skilled in the art from the disclosure herein, members 26" are an example of drag inducing means for facilitating inclination of the binding member 5 relative to a longitudinal axis of the needle 6.

Figure 15:
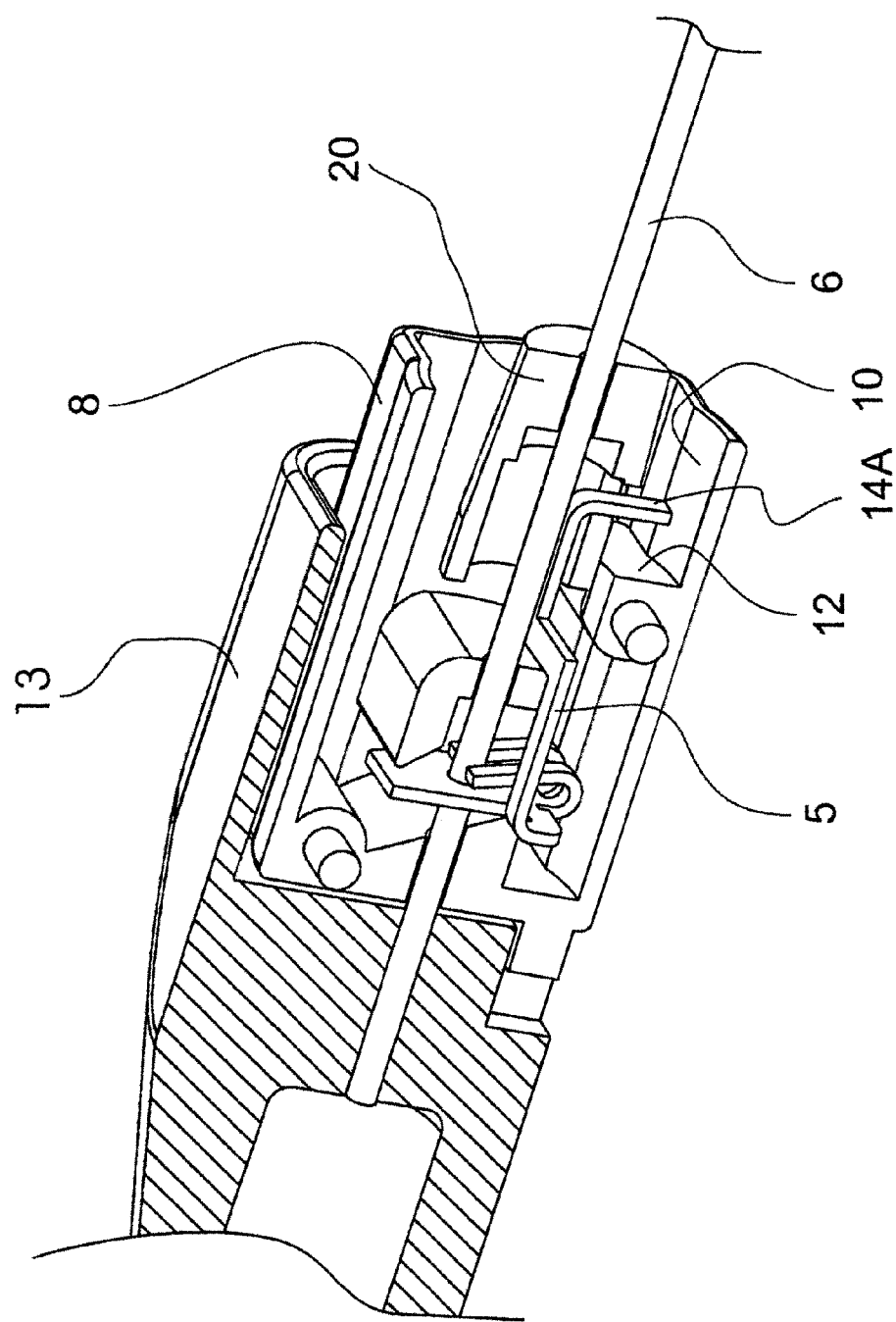
FIG. 15 is an enlarged cross-sectional perspective cutaway view of another embodiment of the medical needle shield apparatus shown in FIG. 1.
Figure 16:
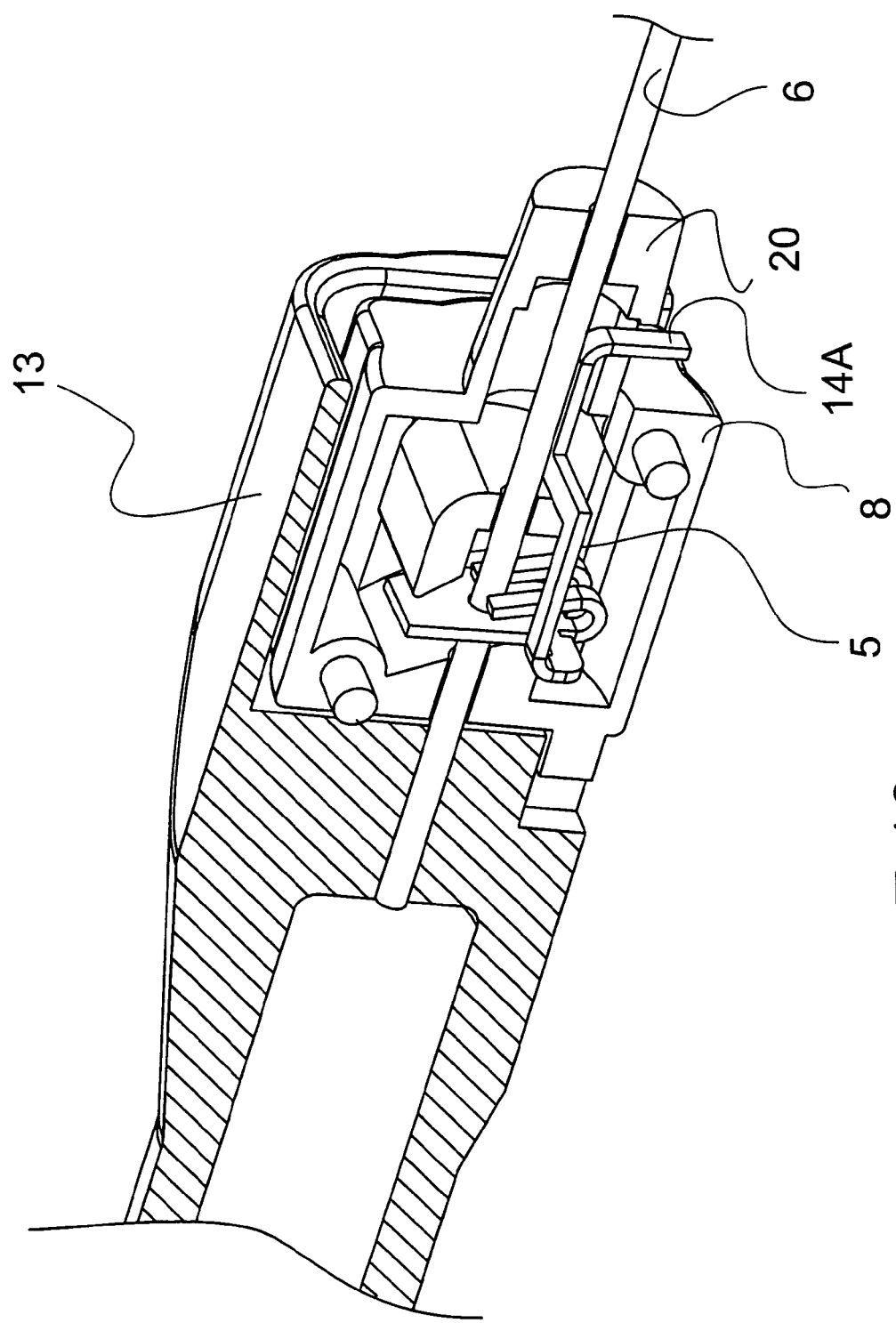
FIG. 16 is an enlarged cross-sectional perspective cutaway view of another embodiment of the medical needle shield apparatus shown in FIG. 1.
Figure 17:
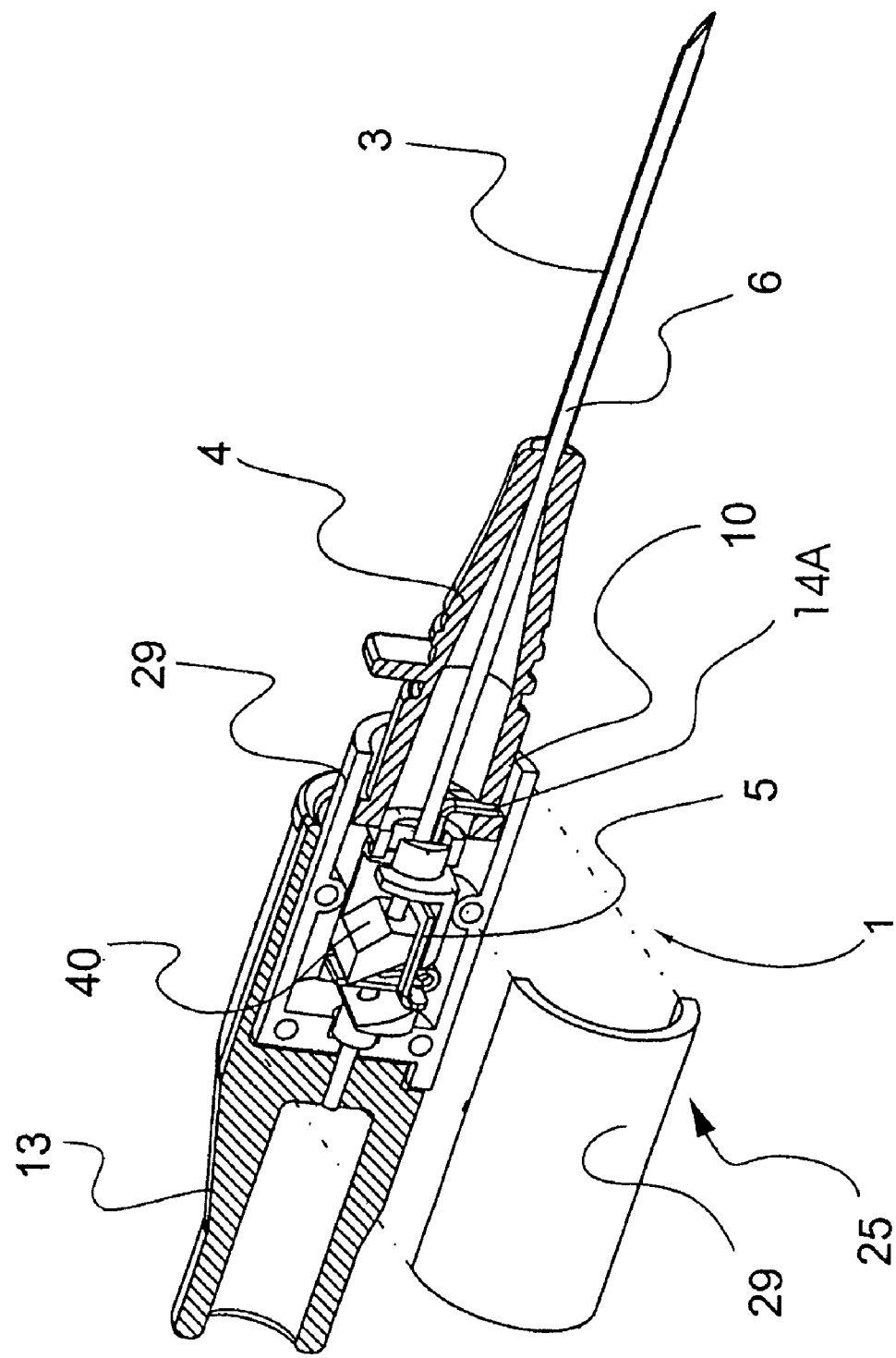
FIG. 17 is a cross-sectional perspective view of another embodiment of the medical needle shield apparatus shown in FIG. 1 with an outer rotatable housing separated therefrom.
Figure 18:
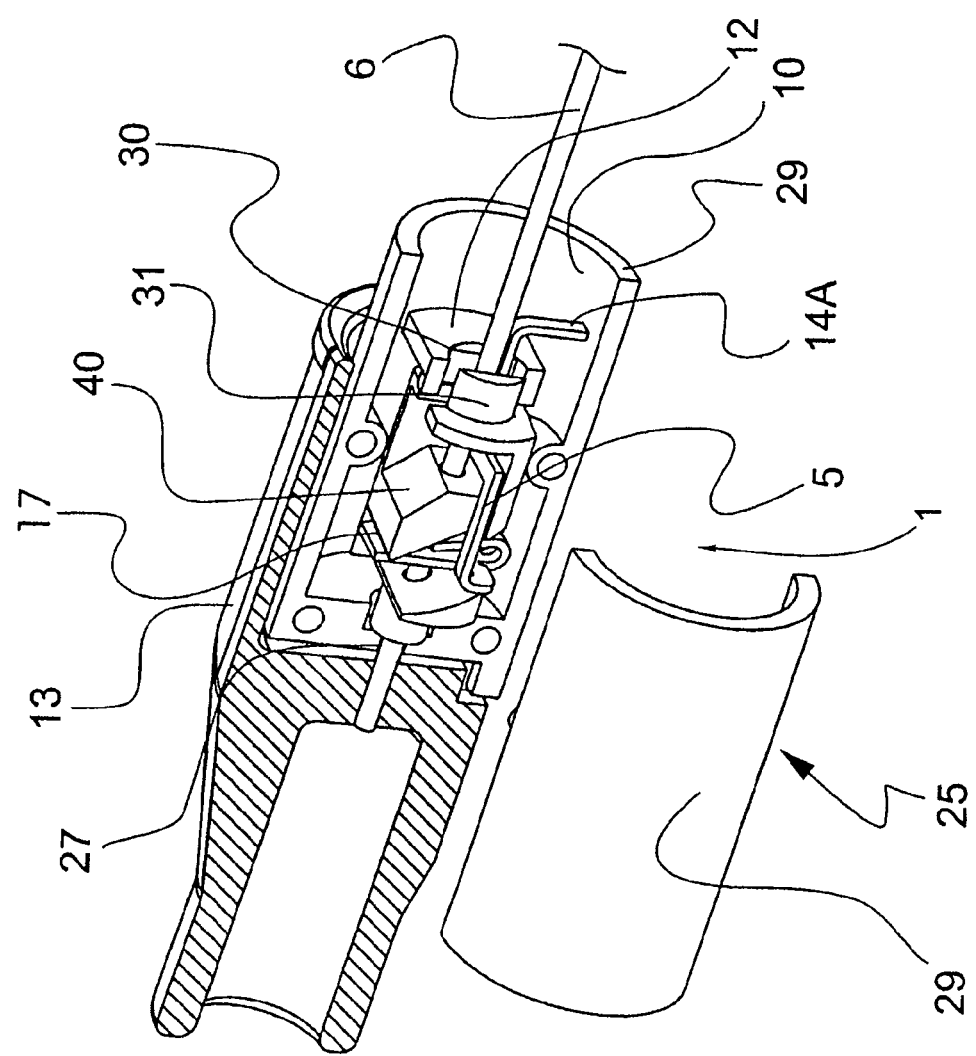
FIG. 18 is an enlarged cross-sectional perspective cutaway view of a distal end of the medical needle shield apparatus shown in FIG. 17.
Figure 19:
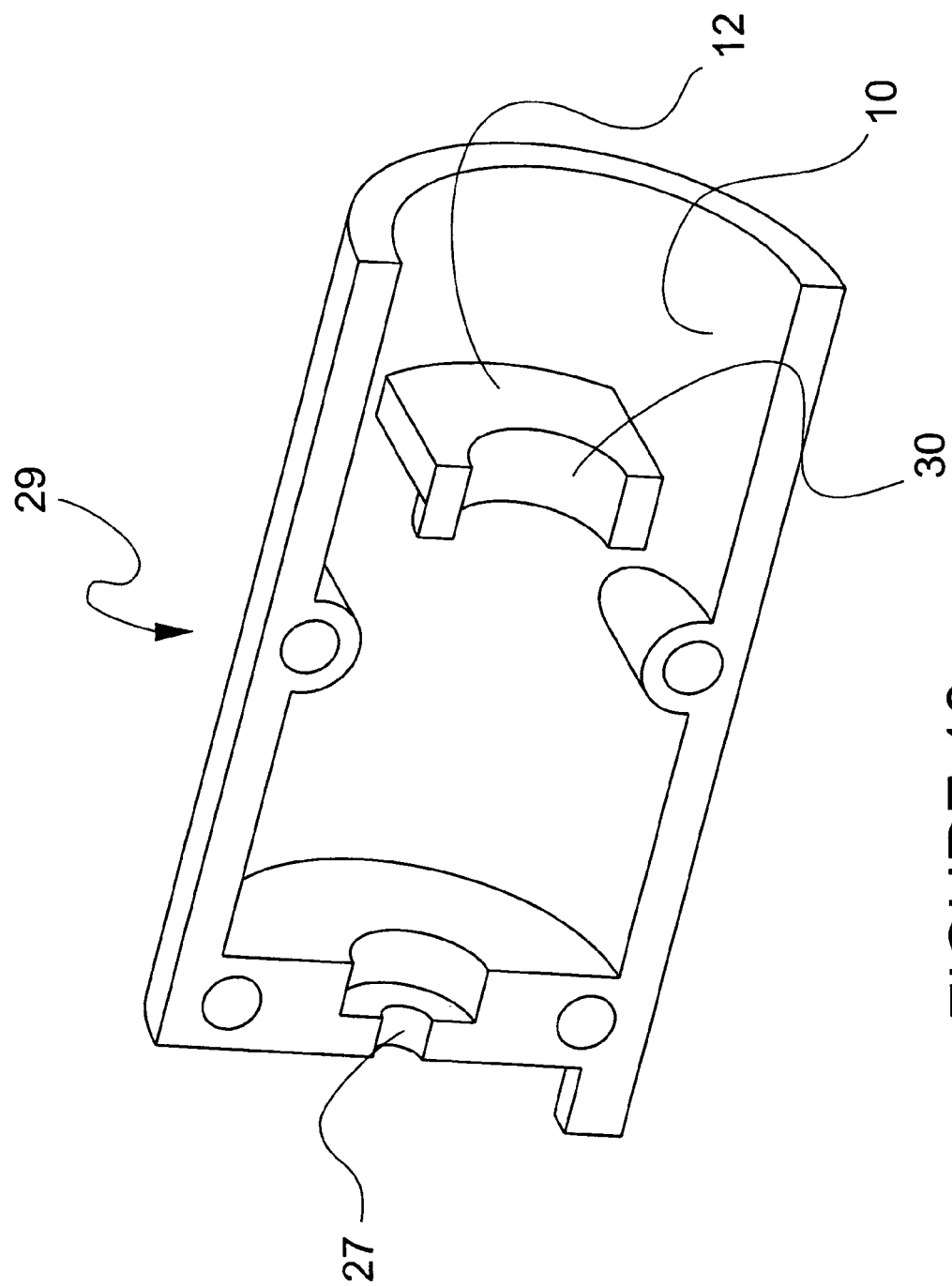
FIG. 19 is an enlarged perspective view of the rotatable housing of the medical needle shield apparatus shown in FIG. 17.
Figure 20:
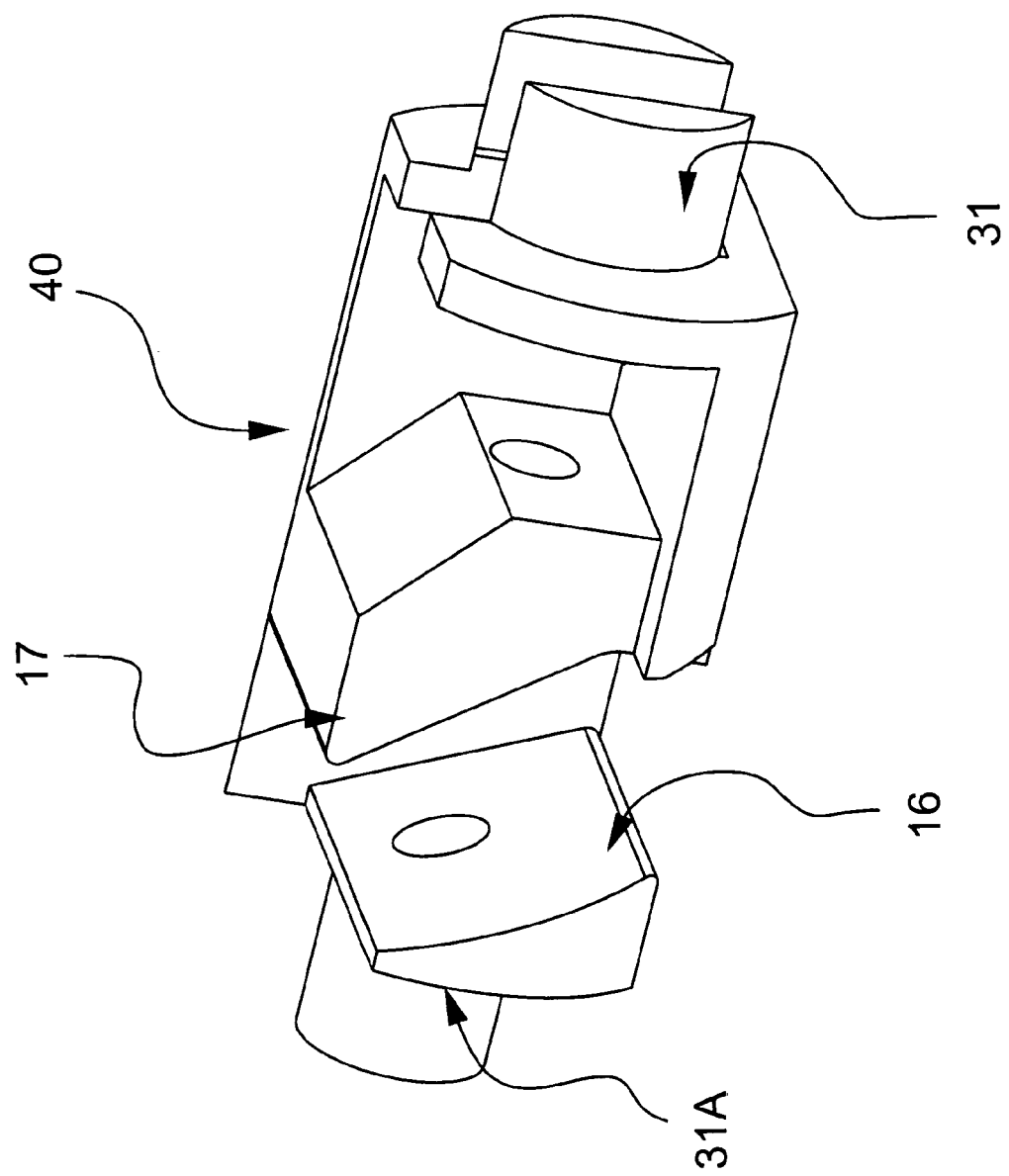
FIG. 20 is an enlarged perspective view of a portion of the housing of the medical needle shield apparatus shown in FIG. 17.

In an alternate embodiment, as shown in FIG. 15, housing 2 includes hub support 20. Hub support 20 is received by catheter hub 4 to advantageously facilitate removable mounting of catheter hub 4 with shield 1. Alternatively, as shown in FIG. 16, control surface 10 of housing 2 may be cut back or eliminated. This configuration allows hub support 20 to solely facilitate mounting of catheter hub 4 via a concentric relationship therewith.

Referring to FIGS. 17-20, another alternate embodiment of the medical needle safety apparatus is shown. A rotatable housing 25, having sections 29, is disposed for rotation and enclosure of shield 1. Rotatable housing 25 is mounted within handle 13 and freely rotates relative to shield 1 and needle 6 in the extended position of shield 1. Relative rotation of rotatable housing 25 is facilitated by support at opening 27 and support 30 formed in rotatable housing 25. Axles 31, 31A are rotationally supported in openings 30, 27, respectively. In a binding orientation, the bearing configuration supports rotation of rotatable housing 25 relative to shield 1 and needle 6. Bearing 40 includes blocking member 16, 17, similar to those discussed. Needle 6 passes through blocking members 16, 17 for slidable movement relative thereto. The halves of axle 31 are spaced apart such that needle 6 and retainer 14 may be disposed therein.

This configuration prevents rotation of shield 1 about longitudinal axis x of needle 6 such that binding member 5 is not undesirably rotated to disturb the protective binding engagement with needle 6. Thus, the possibility of intentionally abusing and defeating the protective configuration of shield 1, in the extended position, by manually and abusively twisting shield 1 is reduced. It is envisioned that, the length of opening 27 may be increased such that the radial clearance of opening 27 with needle 6 limits tilting of shield 1 within rotatable housing 25. This configuration prevents radial contact of shield 1 with rotatable housing 25 and allows elimination of a front bearing.

Figure 21:
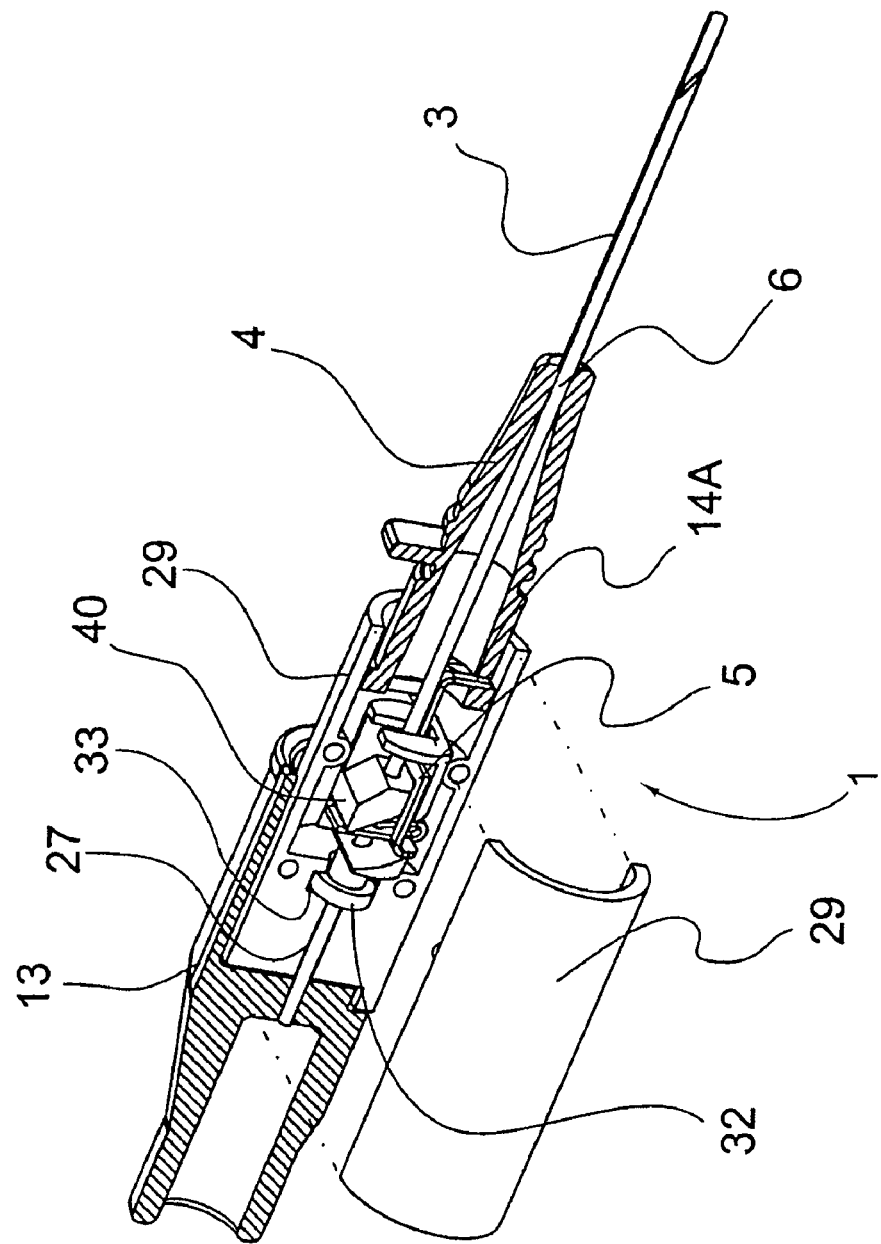
FIG. 21 is a cross-sectional perspective view of another embodiment of the medical needle shield apparatus shown in FIG. 17.
Figure 22:
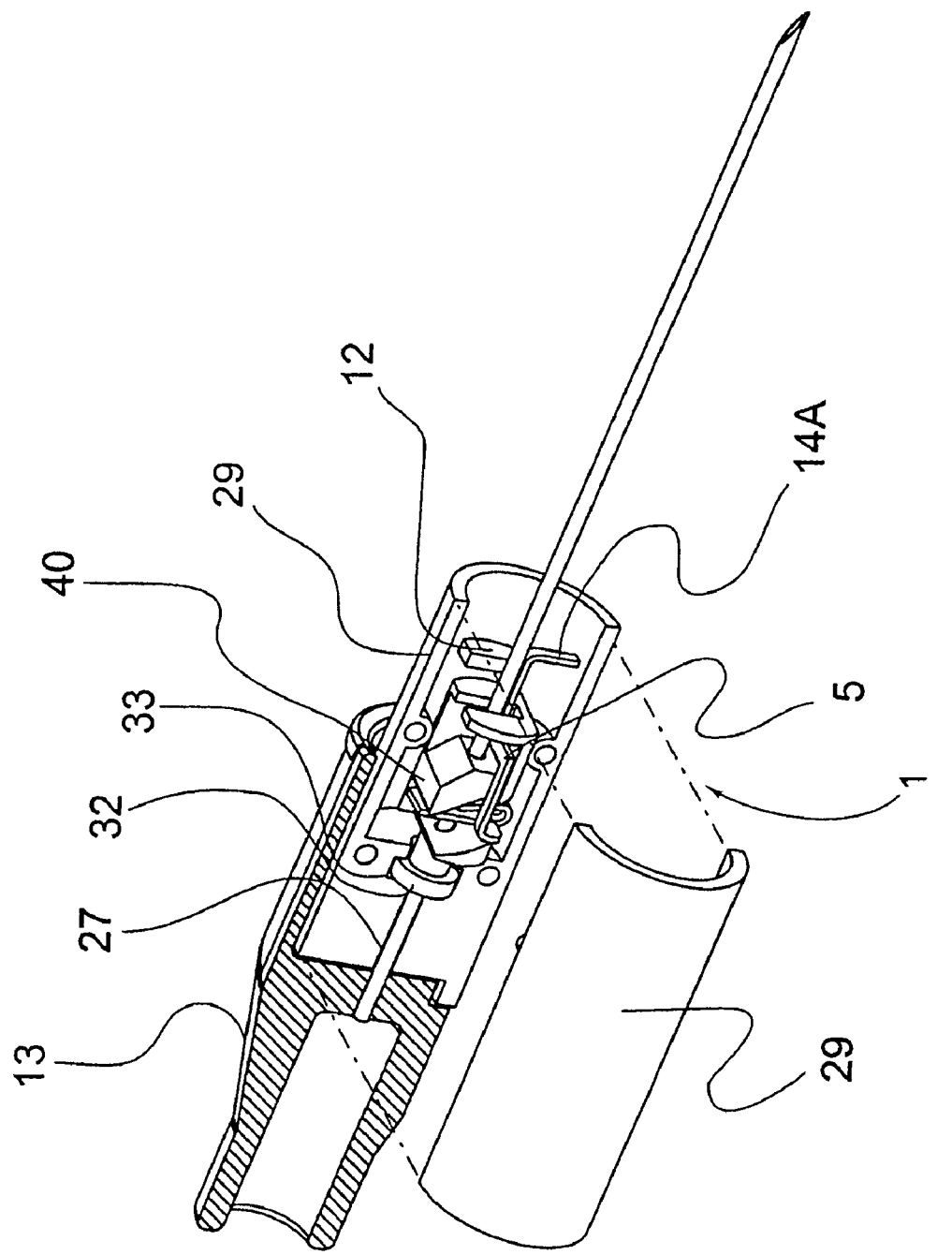
FIG. 22 is a cross-sectional perspective view of the medical needle shield apparatus shown in FIG. 21 with a catheter hub removed.
Figure 23:
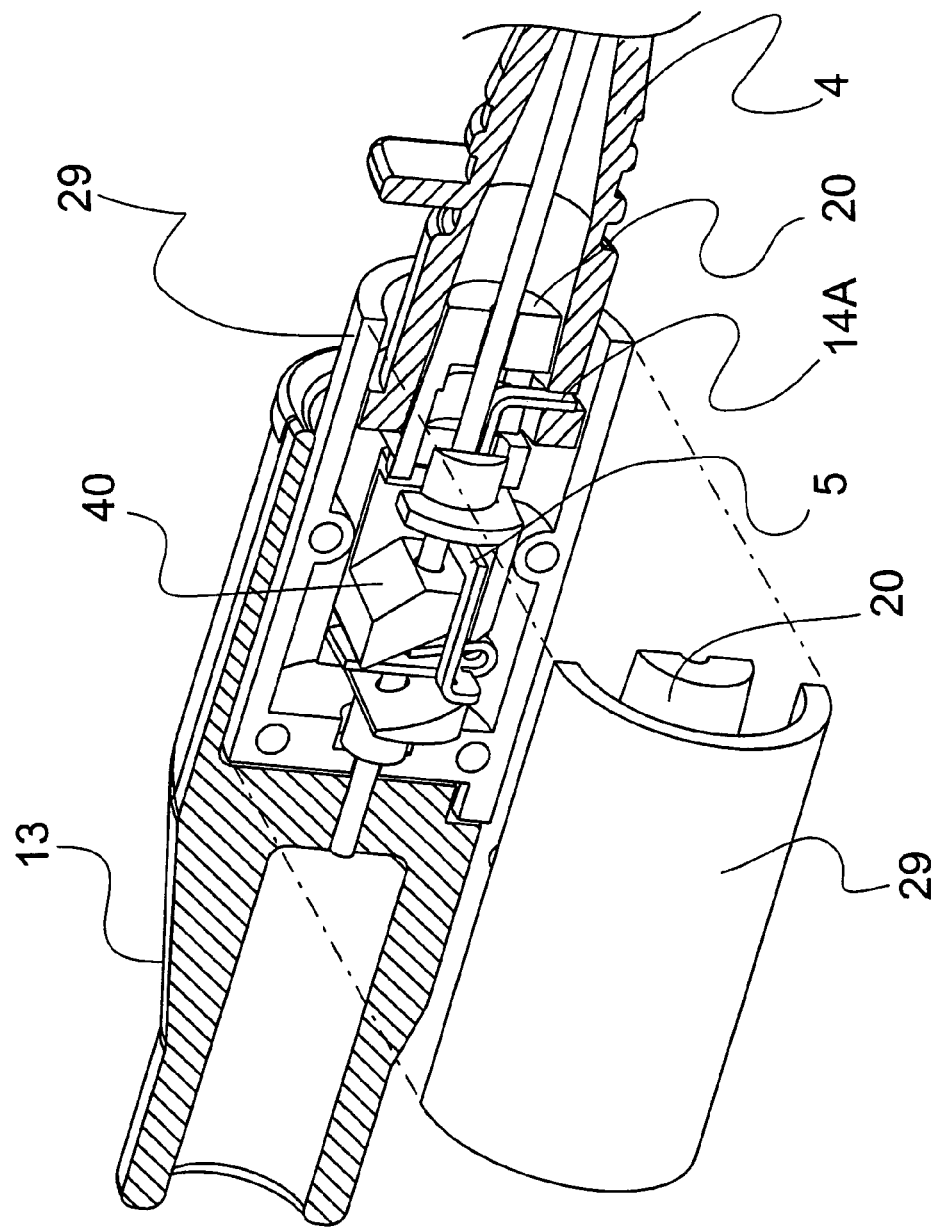
FIG. 23 is an enlarged cross-sectional perspective view of another embodiment of the medical needle shield apparatus shown in FIG. 1 with a hub support member separated.
Figure 24:
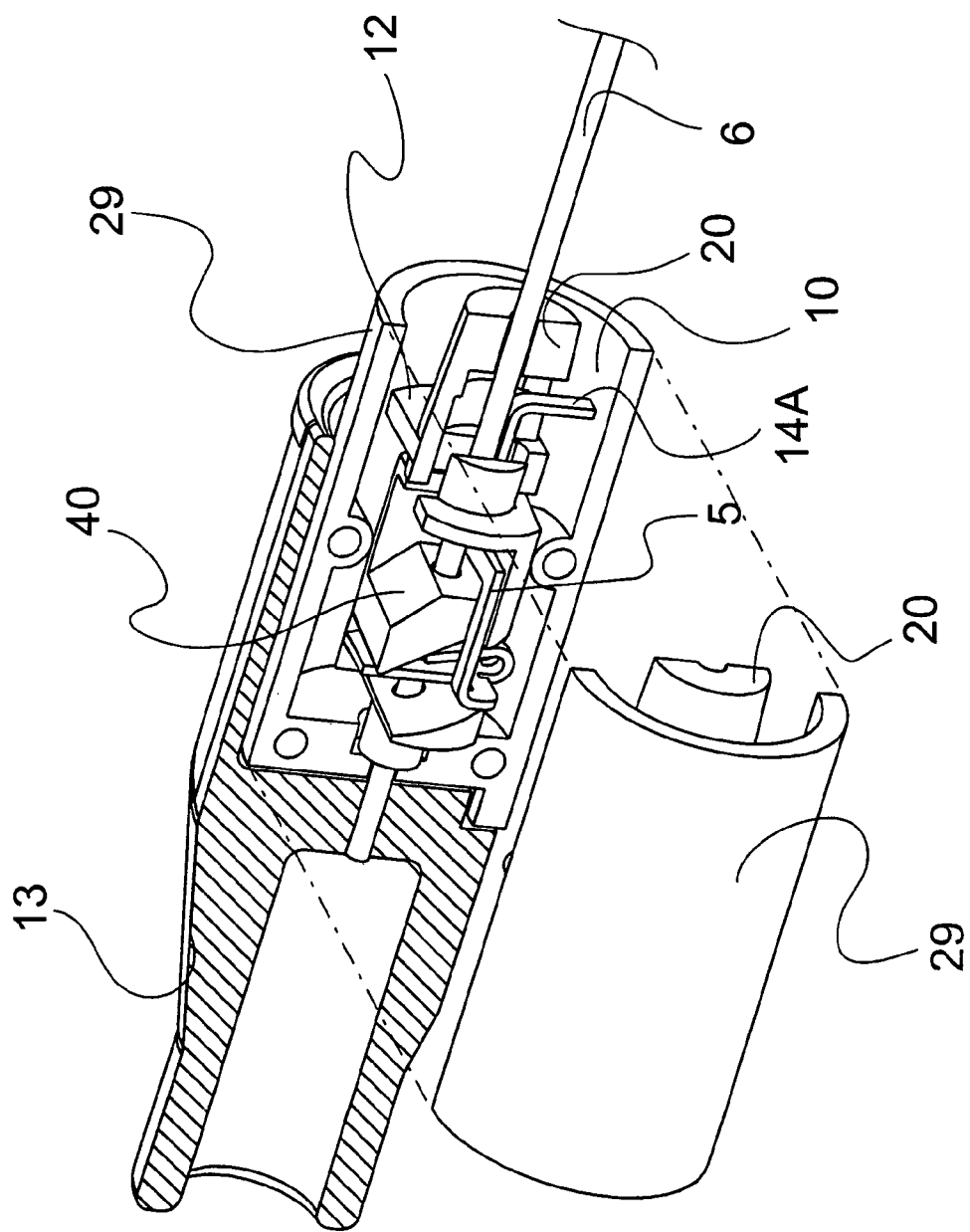
FIG. 24 is a cross-sectional perspective cutaway view of the medical needle shield apparatus shown in FIG. 23 with the catheter hub removed.
Figure 25:
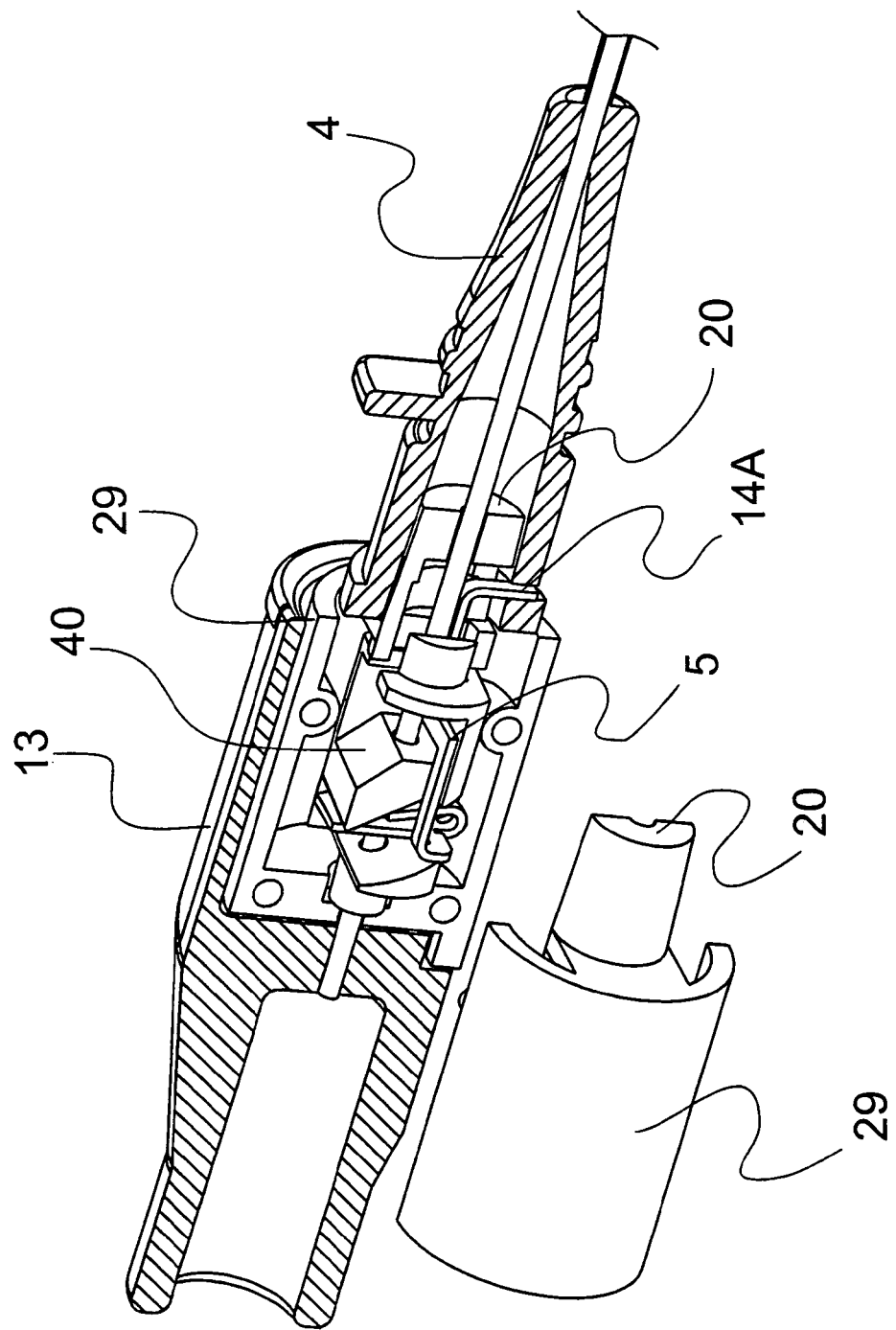
FIG. 25 is a cross-sectional perspective cutaway view of another embodiment of the medical needle shield apparatus shown in FIG. 1 with a rotatable housing separated.
Figure 26:
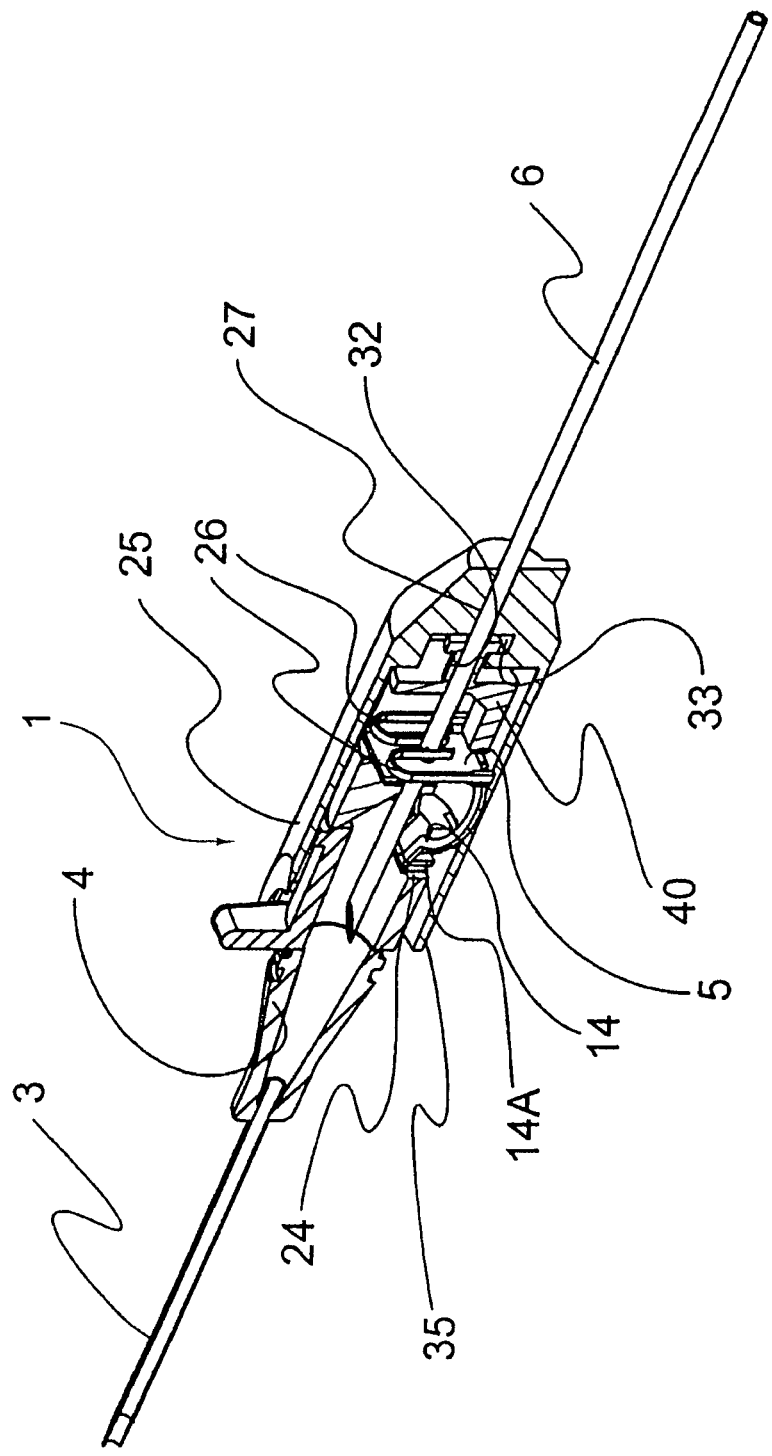
FIG. 26 is a cross-sectional perspective view of another embodiment of the medical needle shield apparatus shown in FIG. 1.
Figure 27:
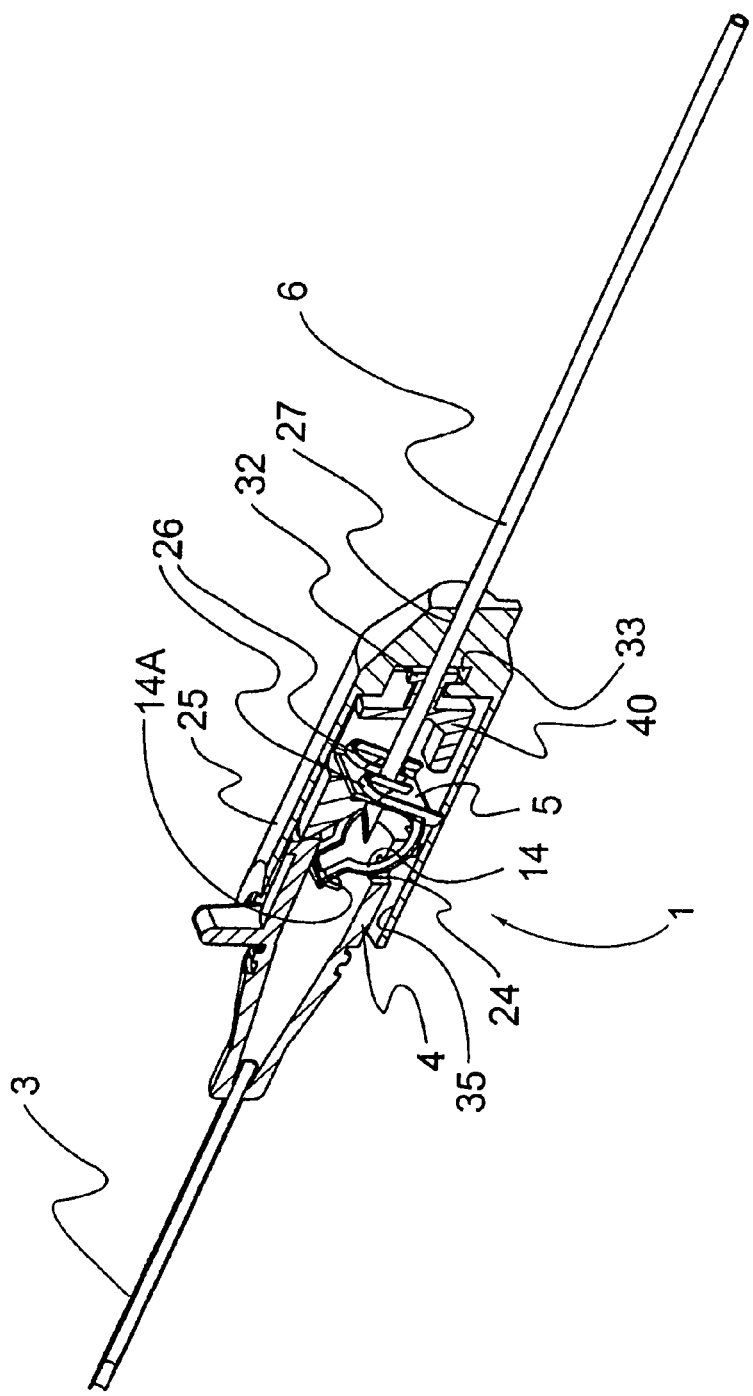
FIG. 27 is a perspective cutaway view of the medical needle shield apparatus shown in FIG. 26 with the shield in an extended position.
Figure 28:
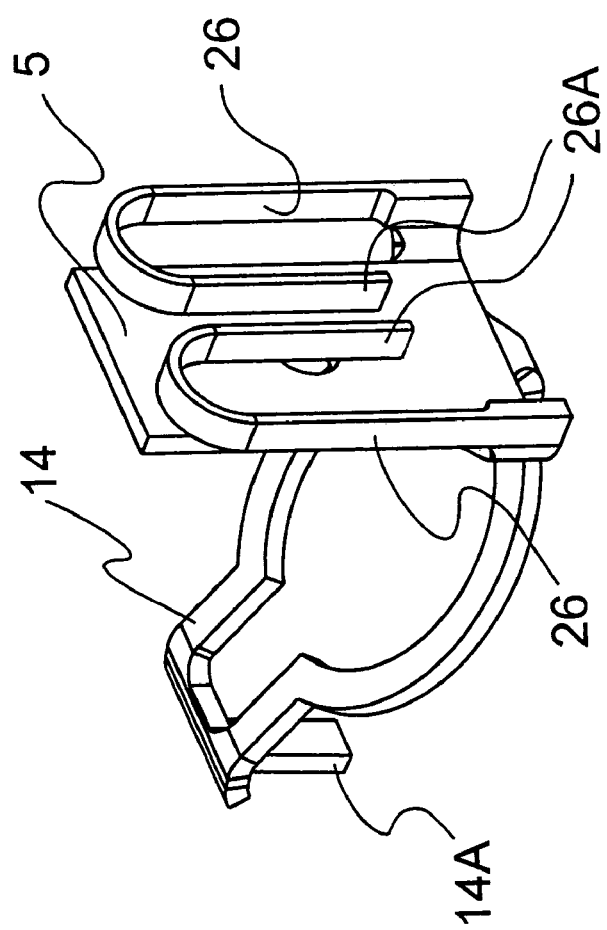
FIG. 28 is an enlarged perspective view of the binding member of the medical needle shield apparatus shown in FIG. 26.
Figure 29:
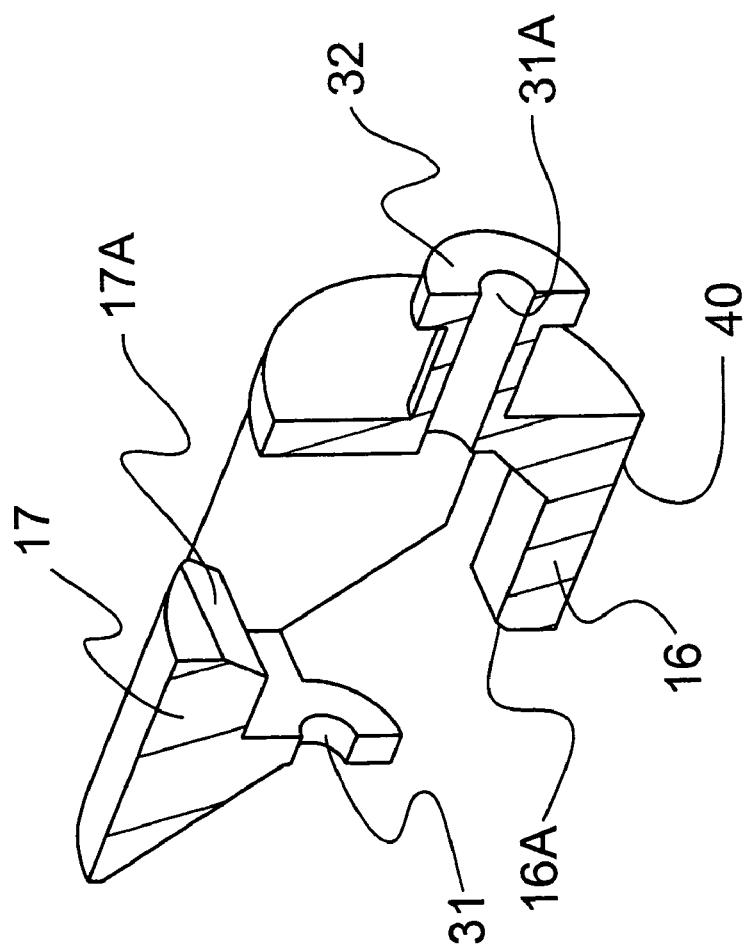
FIG. 29 is an enlarged perspective view of the bearing of the medical needle shield apparatus shown in FIG. 26.

Referring to FIGS. 21 and 22, in an alternate embodiment, bearing 40 includes a thrust collar 32 mounted to needle 6. A corresponding thrust base 33 of rotatable housing 25 is configured to support thrust collar 32 and controls relative axial movement between bearing 40 and rotatable housing 25. Thrust collar 32 freely rotates within thrust base 33 to facilitate rotation of needle 6 and limit tilting of shield 1 within rotatable housing 25. Alternatively, as shown FIGS. 23 and 24, rotatable housing 25 includes a hub support 20, similar to that discussed with regard to FIG. 15. In another alternative, as shown in FIG. 25, control surface 10 of bearing 40 may be cut back or eliminated, similar to that discussed with regard to FIG. 16.

Referring to FIGS. 26-29, another alternate embodiment of the medical needle safety apparatus is shown. A rotatable housing 25 is disposed for rotation and enclosure of shield 1. Rotatable housing 25 freely rotates relative to shield 1 and needle 6 in the extended position of shield 1. Relative rotation of rotatable housing 25 is facilitated by support at opening 27 formed in rotatable housing 25. Axles 31, 31A are rotationally supported in opening 27. In a binding orientation, the bearing configuration supports rotation of rotatable housing 25 relative to shield 1 and needle 6. Bearing 40 includes blocking member 16, 17, similar to those discussed. Needle 6 passes through blocking members 16, 17 for slidable movement relative thereto. The halves of axle 31 are spaced apart such that needle 6 and retainer 14 may be disposed therein.

This configuration prevents rotation of shield 1 about longitudinal axis x of needle 6 such that binding member 5 is not undesirably rotated to disturb the protective binding engagement with needle 6. Thus, the possibility of intentionally abusing and defeating the protective configuration of shield 1, in the extended position, by manually and abusively twisting shield 1 is reduced. It is envisioned that, the length of opening 27 may be increased such that the radial clearance of opening 27 with needle 6 limits tilting of shield 1 within rotatable housing 25. This configuration prevents radial contact of shield 1 with rotatable housing 25 and allows elimination of a front bearing.

Figure 30:
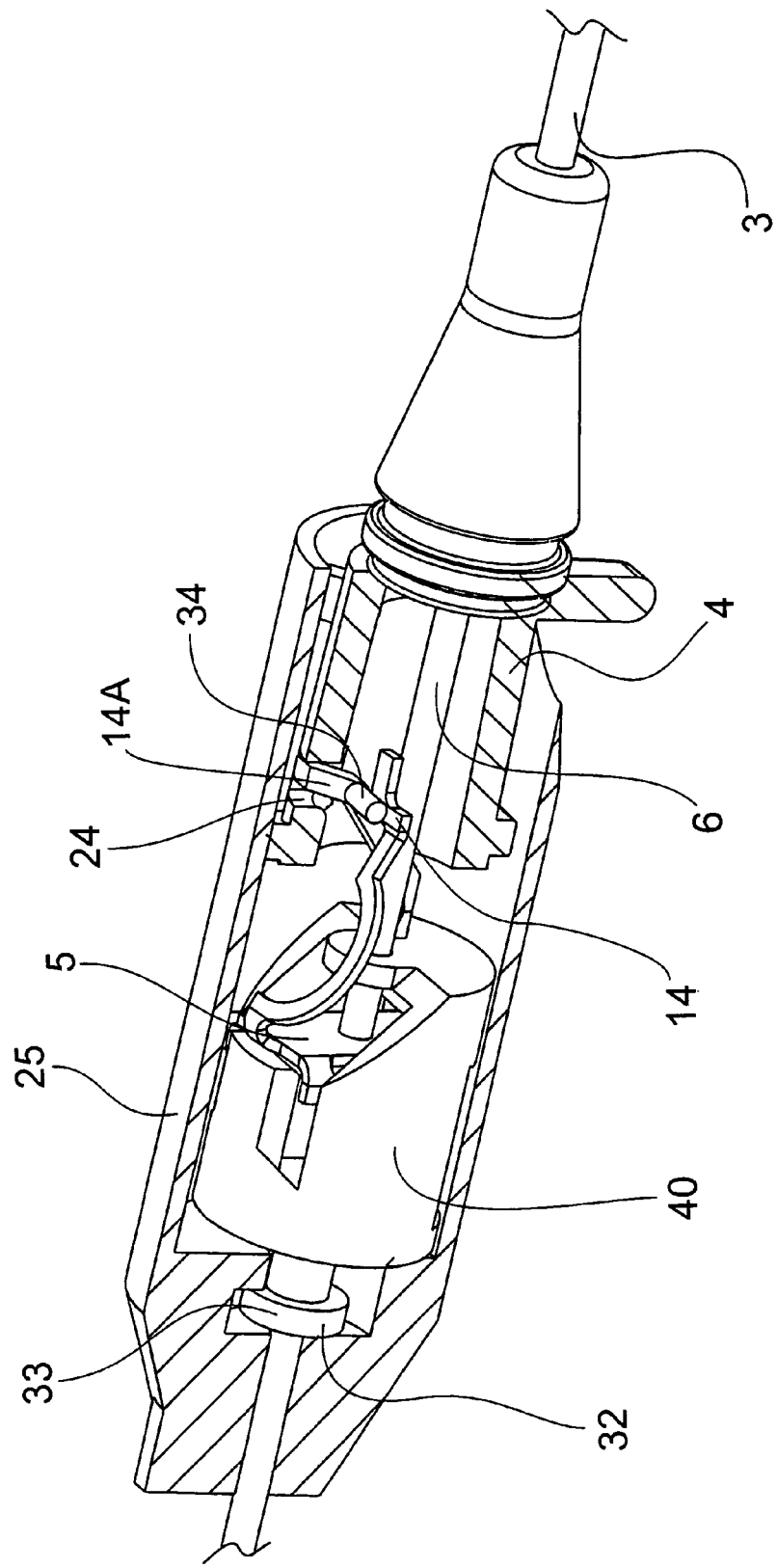
FIG. 30 is a cross-sectional perspective cutaway view of another embodiment of the medical needle shield apparatus shown in FIG. 1.
Figure 31:
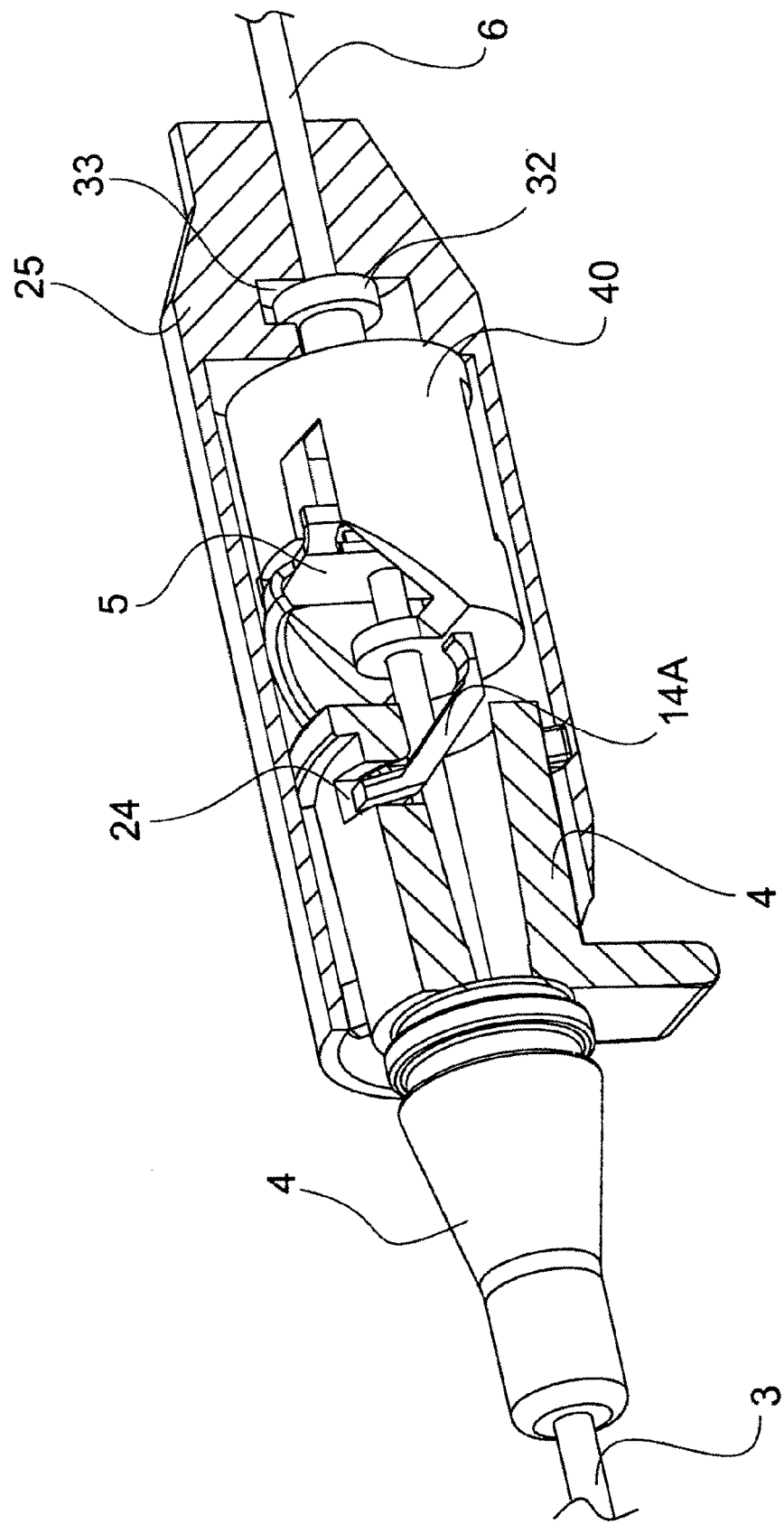
FIG. 31 is a cross-sectional perspective cutaway view of the medical needle shield apparatus shown in FIG. 30.
Figure 32:
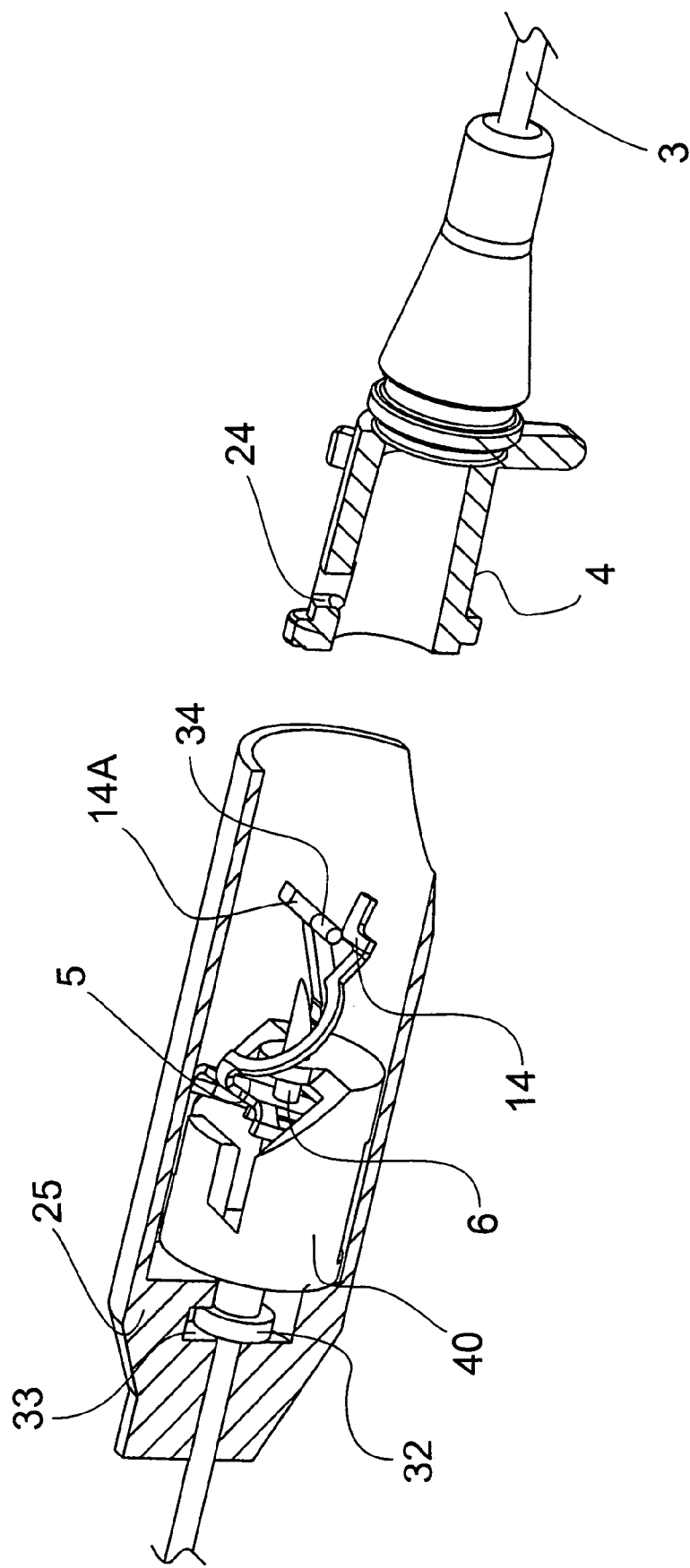
FIG. 32 is a cross-sectional perspective cutaway view of the medical needle shield apparatus shown in FIG. 30.
Figure 33:
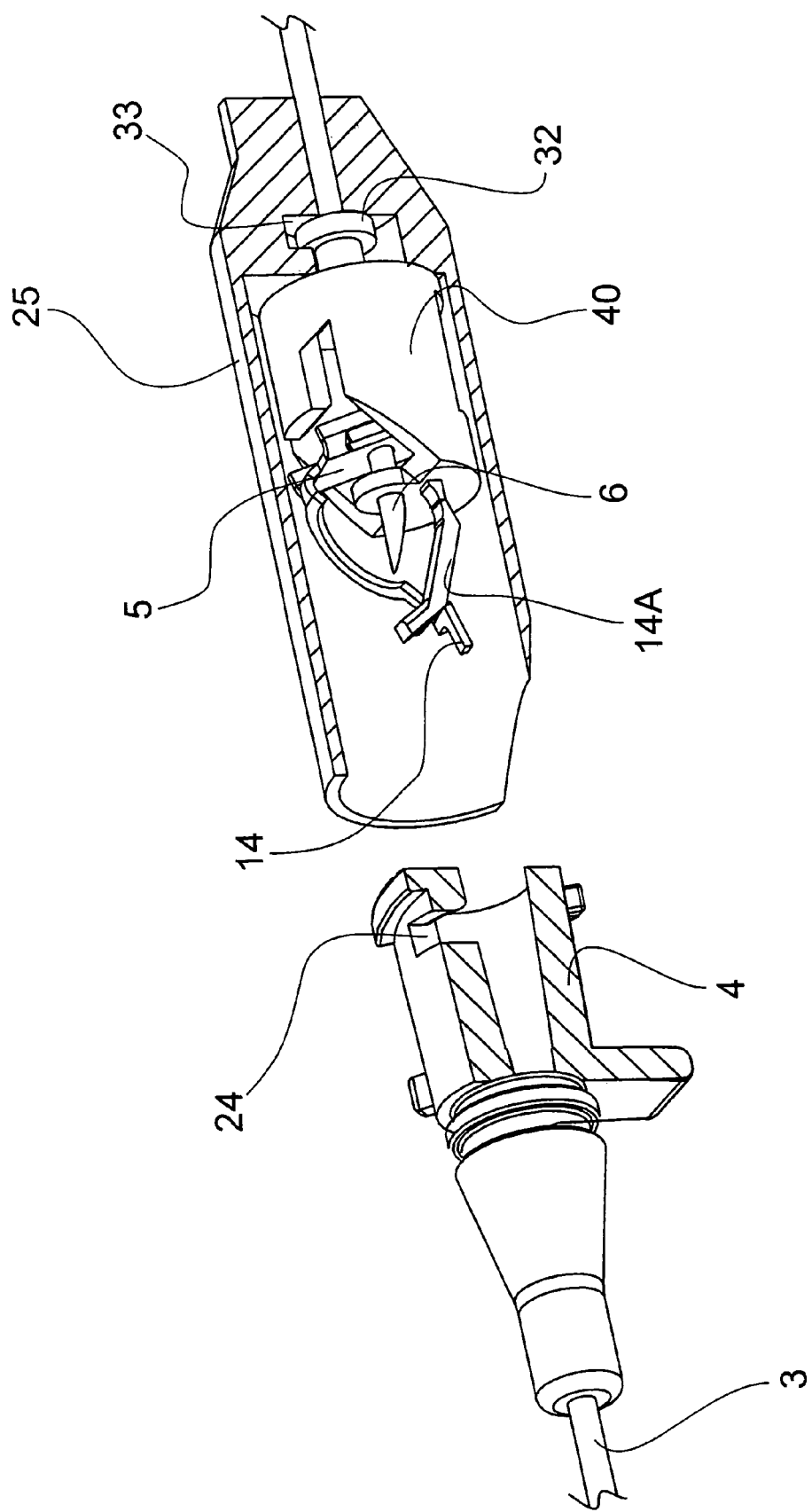
FIG. 33 is a cross-sectional perspective cutaway view of the medical needle shield apparatus shown in FIG. 30.

Referring to FIGS. 30-33, hub retainer 14A may be hingedly connected to bearing 40, such as by a living hinge or the like. FIGS. 30 and 31 illustrate shield 1 prior to activation, wherein Hub retainer 14A includes a portion 34 for engagement with retainer 14 for maintaining hub retainer 14A in hub slot 24. FIGS. 32 and 33 illustrate shield 1 after activation, wherein the movement of retainer 14 upon activation of shield 1 in the extended position allows portion 34 to move and release hub retainer 14A from hub slot 24.

Figure 34:
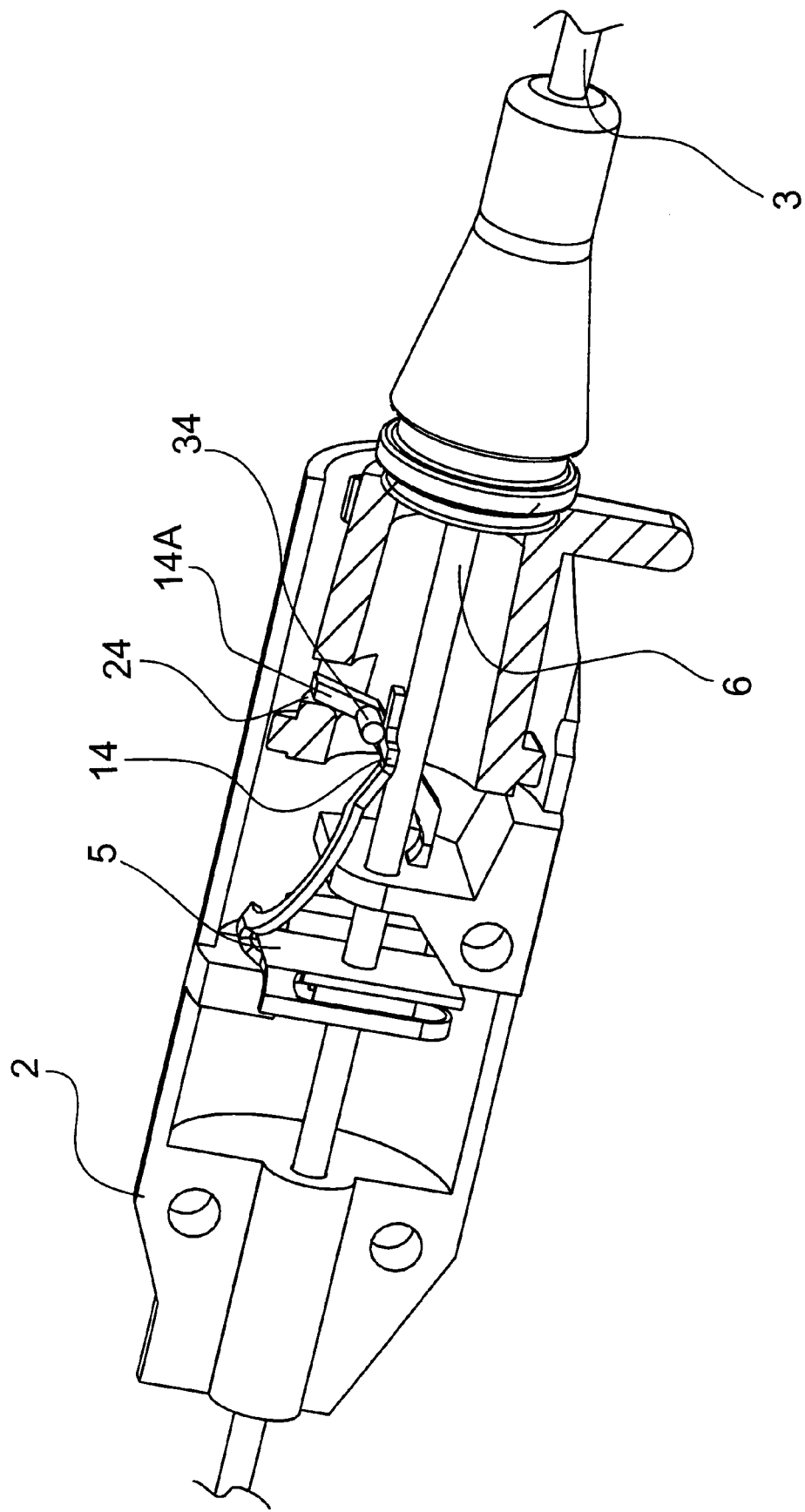
FIG. 34 is a cross-sectional perspective view of another embodiment of the medical needle shield apparatus shown in FIG. 1 with a housing section separated therefrom.
Figure 35:
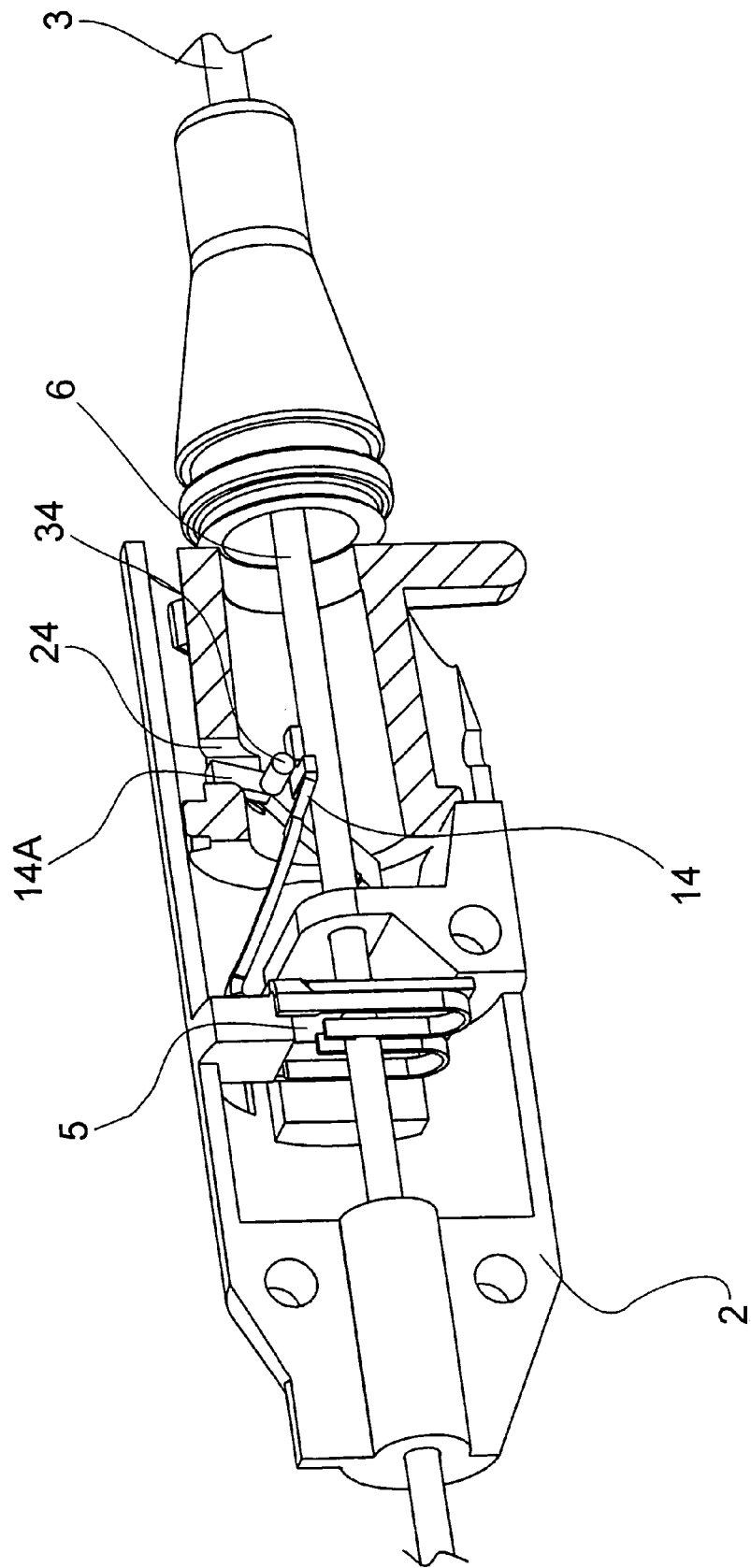
FIG. 35 is a cross-sectional perspective cutaway view of the medical needle shield apparatus shown in FIG. 34.
Figure 36:
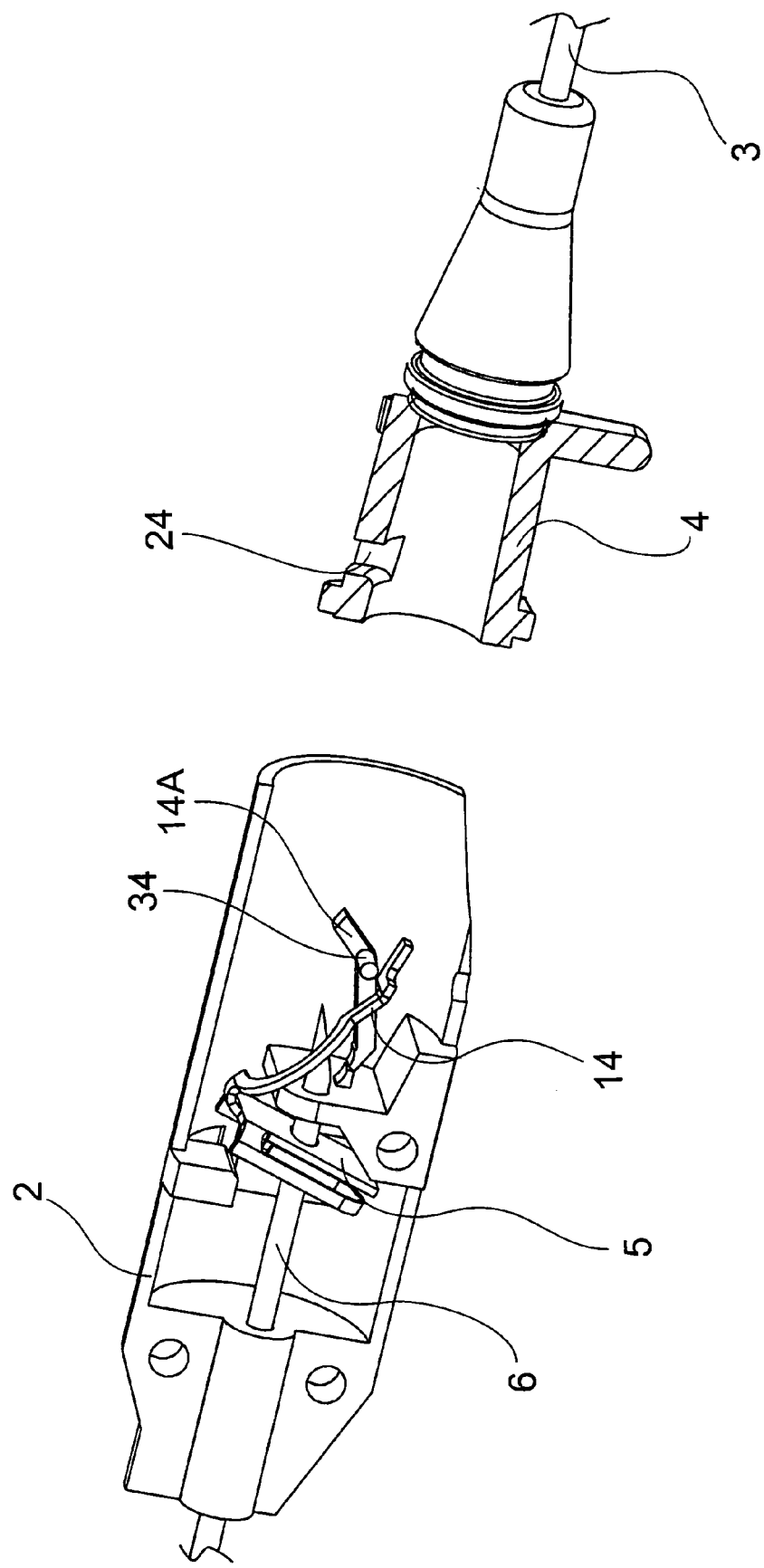
FIG. 36 is a cross-sectional perspective cutaway view of the medical needle shield apparatus shown in FIG. 34.
Figure 37:
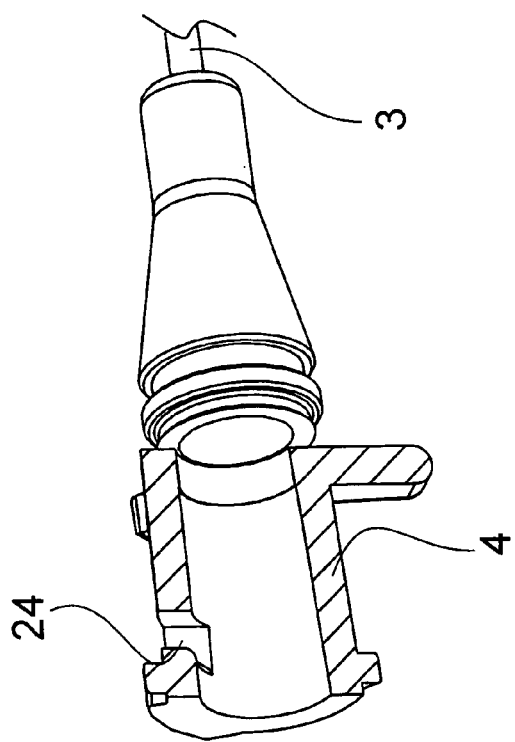
FIG. 37 is a cross-sectional perspective cutaway view of the medical needle shield apparatus shown in FIG. 34.
Figure 37:
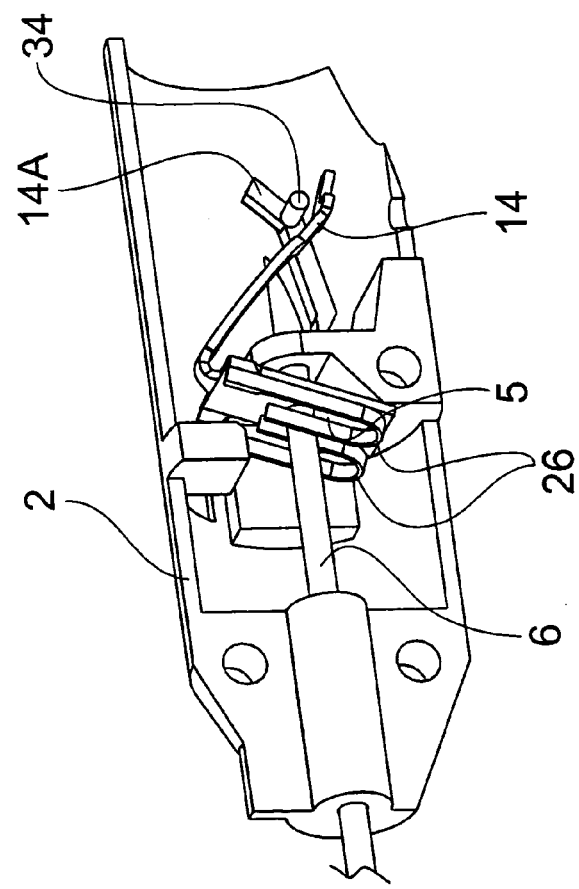

The embodiments illustrated in FIGS. 34-37 depict a hub retainer 14A hingedly connected to housing 2. FIGS. 34 and 35 illustrate shield 1 prior to activation, wherein Hub retainer 14A includes a portion 34 for engagement with retainer 14 for maintaining hub retainer 14A in hub slot 24. FIGS. 36 and 37 illustrate shield 1 after activation, wherein the movement of retainer 14 upon activation of shield 1 in the extended position allows portion 34 to move and release hub retainer 14A from hub slot 24.

Figure 38:
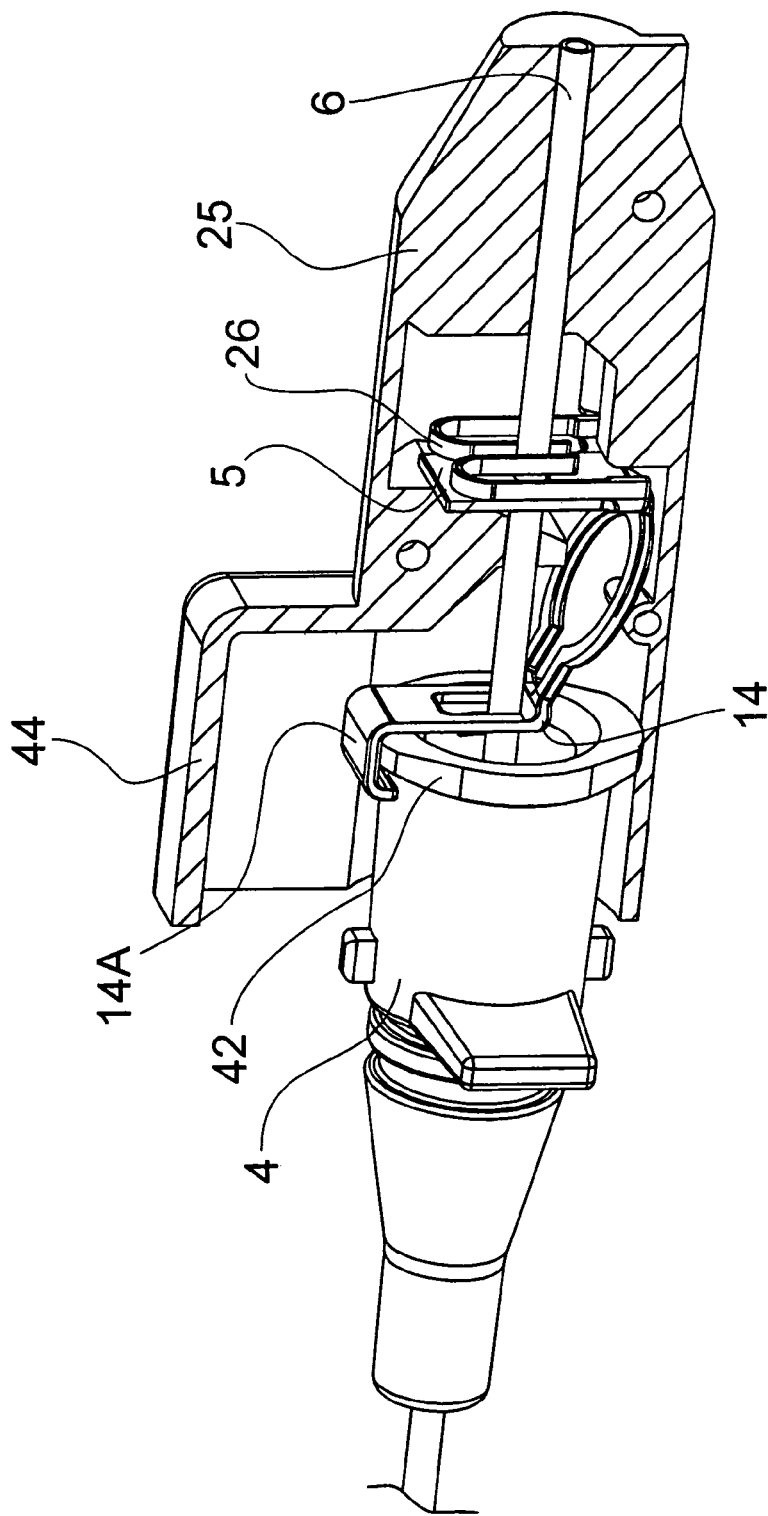
FIG. 38 is a cross-sectional perspective view of another embodiment of the medical needle shield apparatus shown in FIG. 1.
Figure 39:
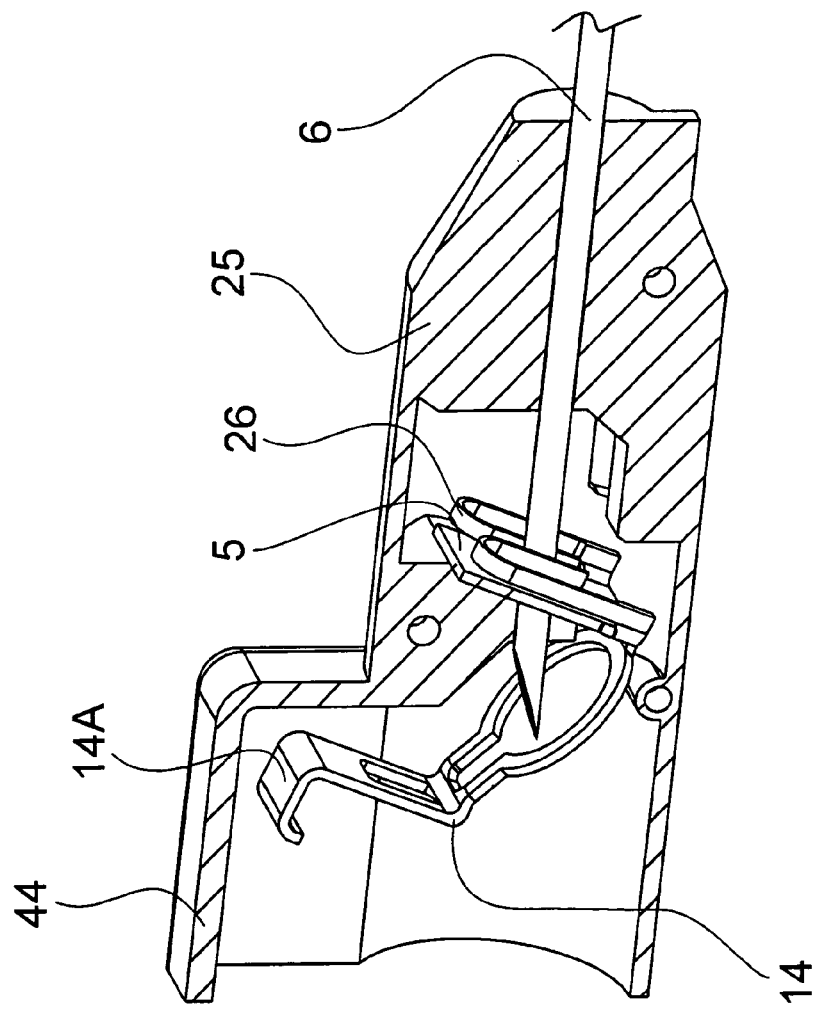
FIG. 39 is a cross-sectional perspective cutaway view of the medical needle shield apparatus shown in FIG. 38 in the extended position.
Figure 39:
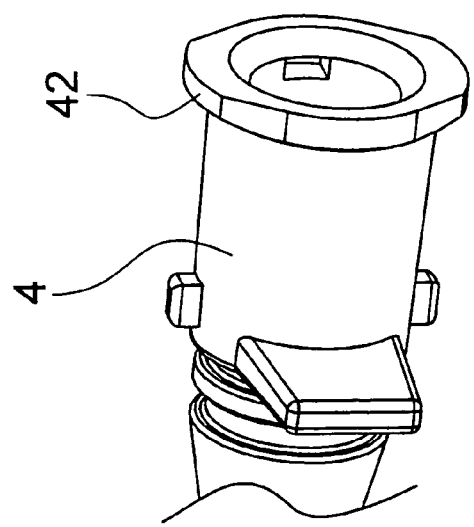

The embodiments illustrated in FIGS. 38-39 depict a shield having a hub retainer 14A which engages the catheter hub 4 via flange 42. FIG. 38 illustrates shield 1 prior to activation. FIG. 39 illustrates shield 1 after activation, wherein the movement of retainer 14 upon activation of shield 1 in the extended position allows retainer 14 to move and release hub retainer 14A from flange 42. Retainer shield 44 protects hub retainer 14A from being inadvertently moved from its intended position.

Figure 40:
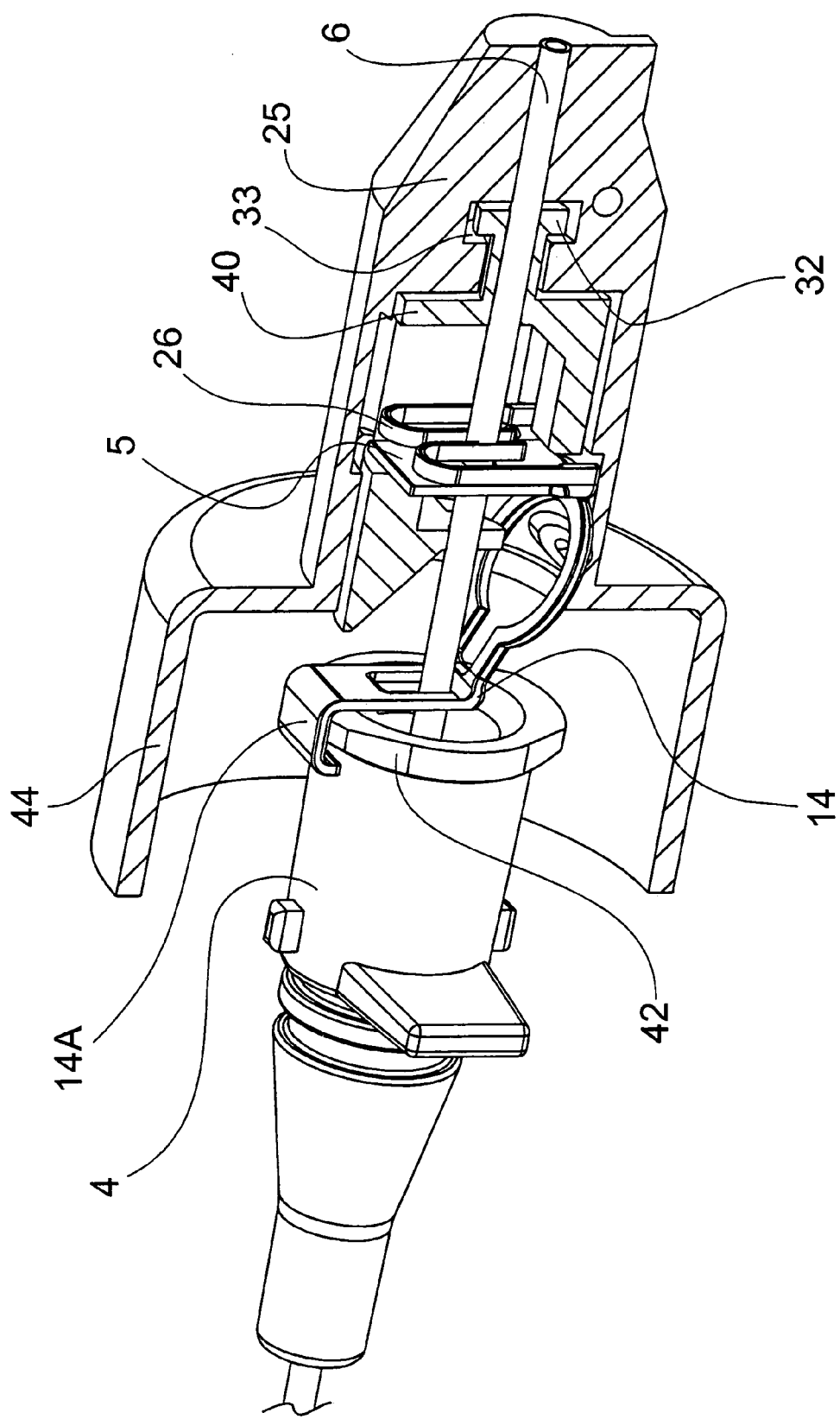
FIG. 40 is a cross-sectional perspective view of another embodiment of the medical needle shield apparatus shown in FIG. 1.
Figure 41:
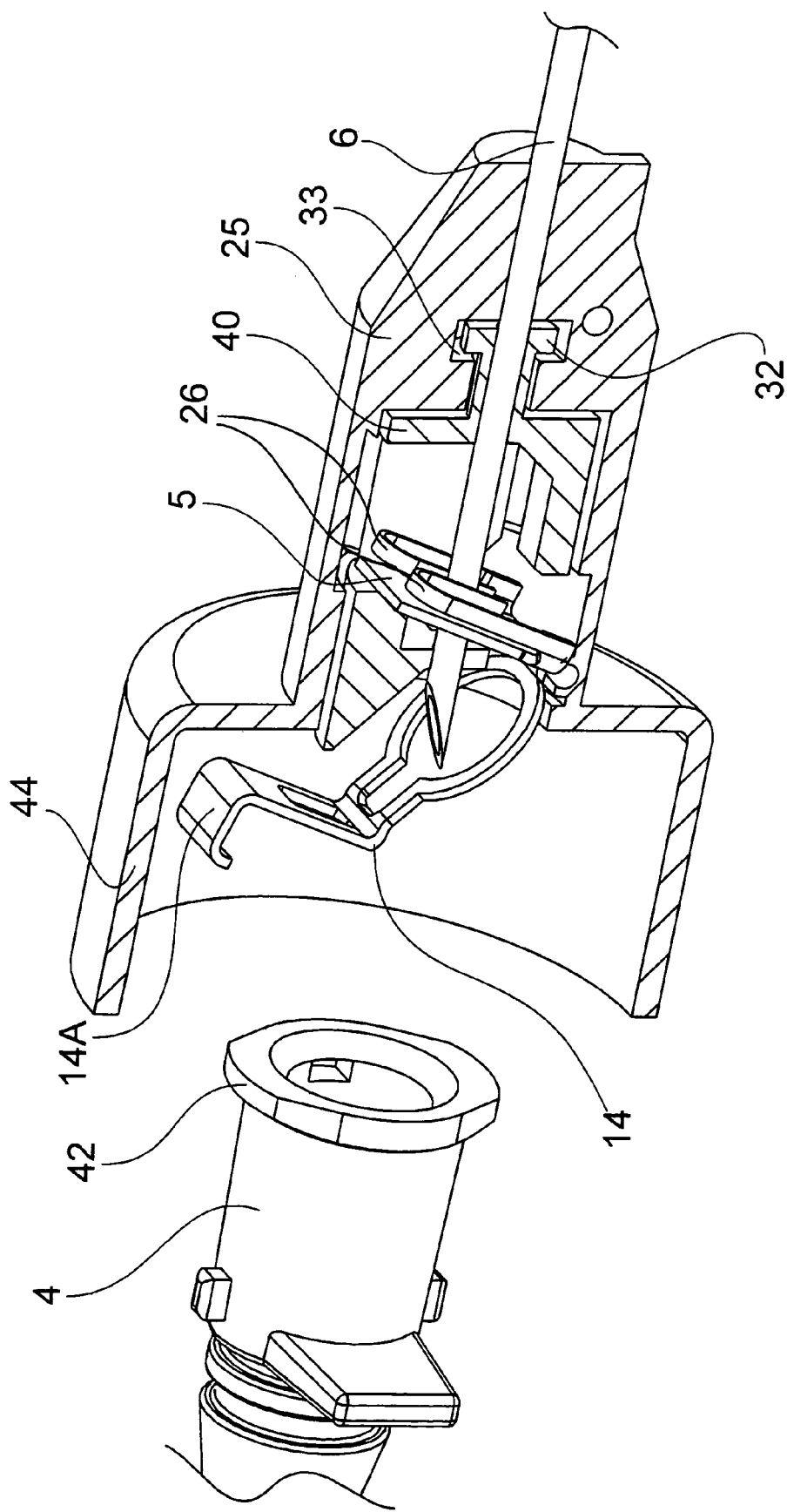
FIG. 41 is a cross-sectional perspective cutaway view of the medical needle shield apparatus shown in FIG. 40 in the extended position.

Referring to FIGS. 40-41, the illustrated embodiments depict a rotatable shield having a hub retainer 14A which engages the catheter hub 4 via flange 42. FIG. 40 illustrates shield 1 prior to activation. FIG. 41 illustrates shield 1 after activation, wherein the movement of retainer 14 upon activation of shield 1 in the extended position allows retainer 14 to move and release hub retainer 14A from flange 42. Retainer shield 44 extends circumferentially to provide for rotation of hub retainer 14A about needle 6 and to protect hub retainer 14A from being inadvertently moved from its intended position.

Figure 42:
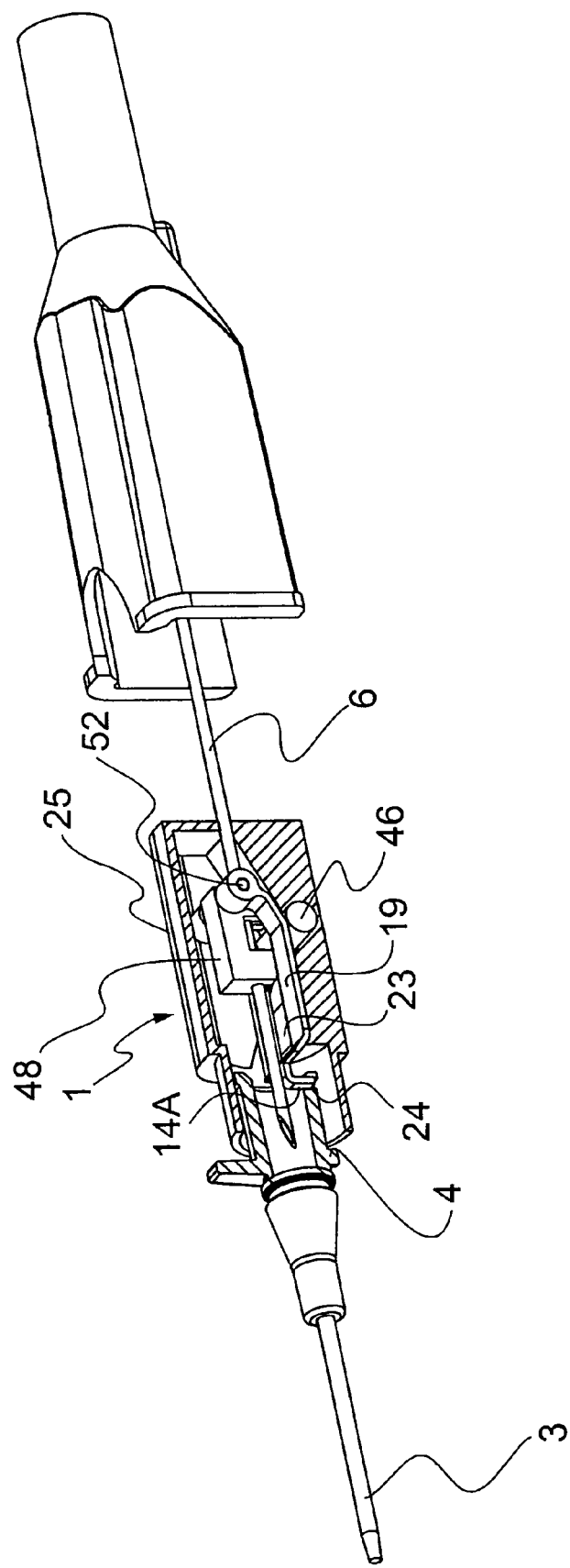
FIG. 42 is a cross-sectional perspective view of another embodiment of the medical needle shield apparatus shown in FIG. 1.
Figure 43:
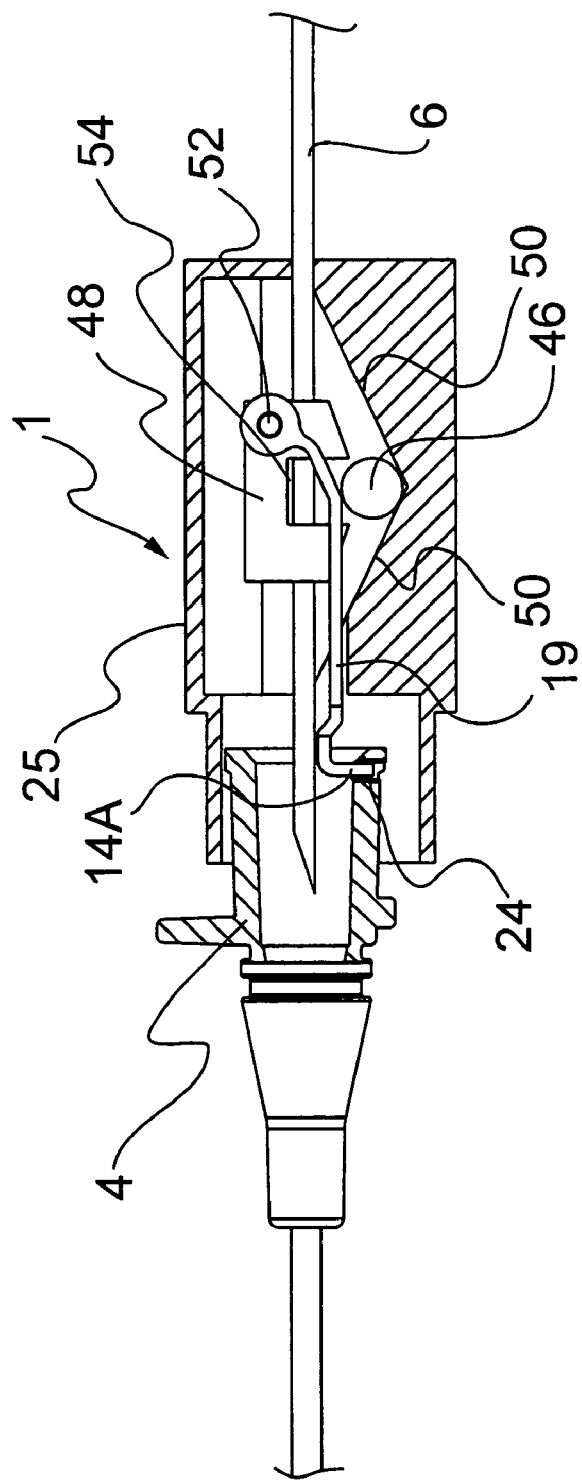
FIG. 43 is a cross-sectional view of the medical needle shield apparatus shown in FIG. 42.

Referring to FIGS. 42-46, another alternate embodiment of the medical needle safety apparatus is shown. FIGS. 42 and 43 illustrate shield 1 prior to activation, wherein binding member 46 is disposed within a cavity 54 of sliding member 48. Sliding member 48 receives needle 6 for slidable receipt via friction between the retracted position and extended position of shield 1. End sensing member 19 extends distally from sliding member 48. It is envisioned that end sensing member 19 may be variously oriented with sliding member 48 and may flexibly extend therefrom, such as by a hinge 52 or the like. Needle communicating surface 23 extends from end sensing member 19. In a non-binding or sliding orientation, needle communicating surface 23 slidably engages needle 6, as shown in FIGS. 42 and 43. Needle communicating surface 23 engages needle 6 and maintains the non-binding or sliding orientation of binding member 46 by opposing the force of end sensing member 19 directed to needle 6. The force, as created by the binding member against end sensing member 19 described below, is generated by ramp surface 50 engaging binding member 46. Binding engagement, however, is prevented in the non-binding or sliding orientation because of the engagement of needle communicating surface 23 with needle 6, as shown in FIGS. 42 and 43. As needle 6 is retracted proximally and shield is extended distally, needle 6 continues to slideably engage needle communicating surface 23, as shown in FIGS. 42 and 43. It is envisioned that needle communicating surface 23 may include ribs, projections, cavities, etc. for engagement with needle 6 or that a portion of needle communicating surface 23 engages needle 6.

Figure 44:
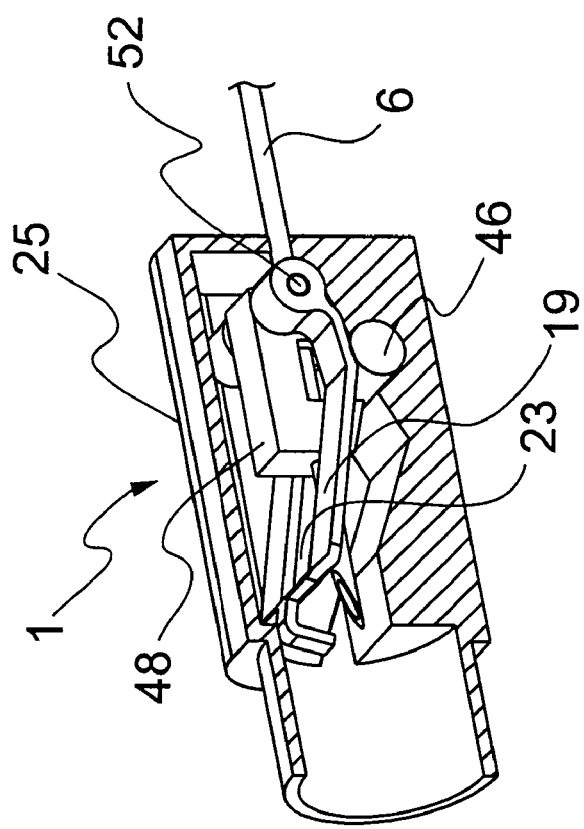
FIG. 44 is a cross-sectional perspective view of the medical needle shield apparatus shown in FIG. 42 in the extended position.
Figure 45:
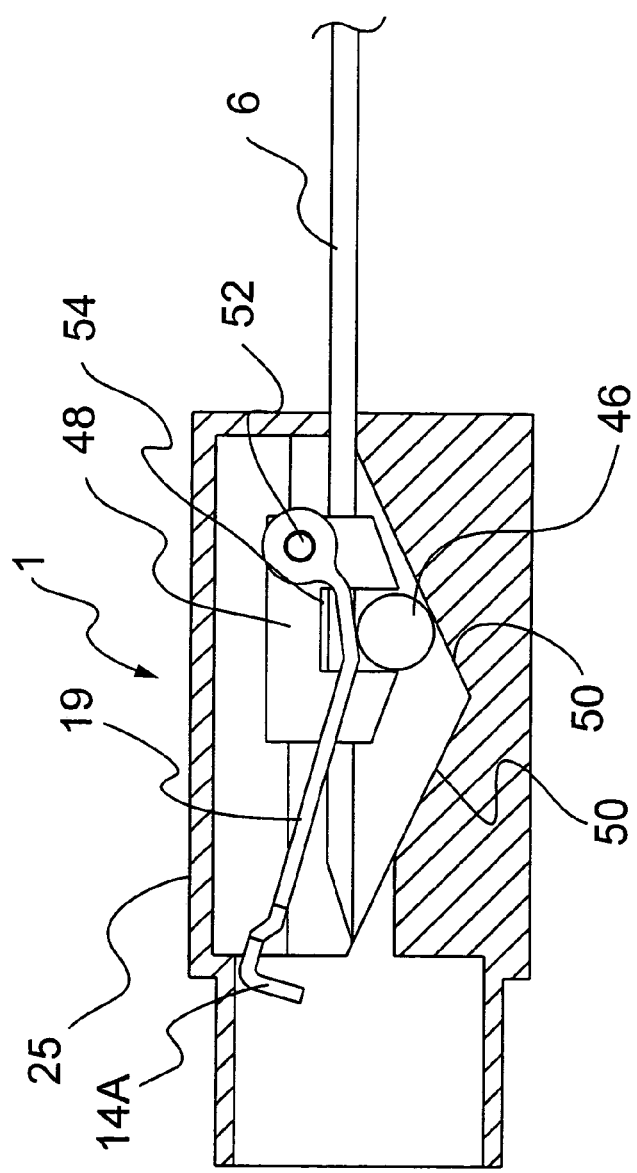
FIG. 45 is a cross-sectional view of the medical needle shield apparatus shown in FIG. 44.
Figure 46:
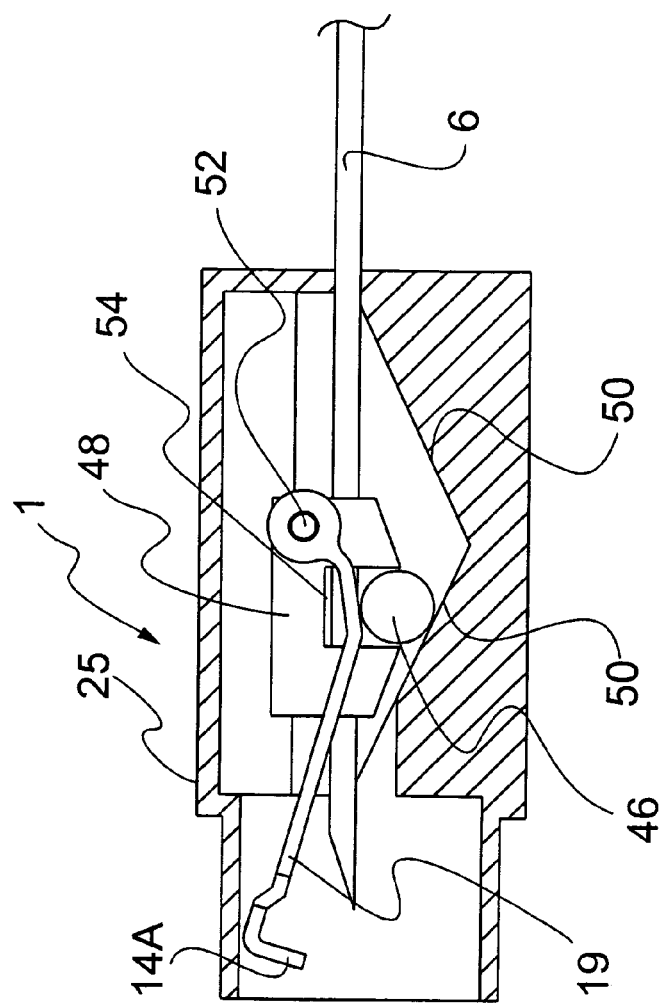
FIG. 46 is a cross-sectional view of the medical needle shield apparatus shown in FIG. 44.

Referring to FIGS. 44-46, as needle 6 is released from engagement with needle communicating surface 23 when the shield 1 is in the extended position, the force created by ramp 50 against binding member 46 causes end sensing member 19 to move and allow binding member 46 to contact needle 6 in binding engagement via binding surface on binding member 46. As shown in FIGS. 45 and 46, ramp surfaces 50 allow binding engagement of binding member 46 to needle 6 as the shield is moved in either axial direction along needle 6.

Catheter hub 4 has a hub slot 24 for receipt and engagement with hub retainer 14A. Hub retainer 14A extends from end sensing member 19. Hence, as needle 6 is released from engagement with needle communicating surface 23 disposed on end sensing member 19, hub retainer 14A is disengaged from catheter hub 4 for release therefrom.

Figure 47:
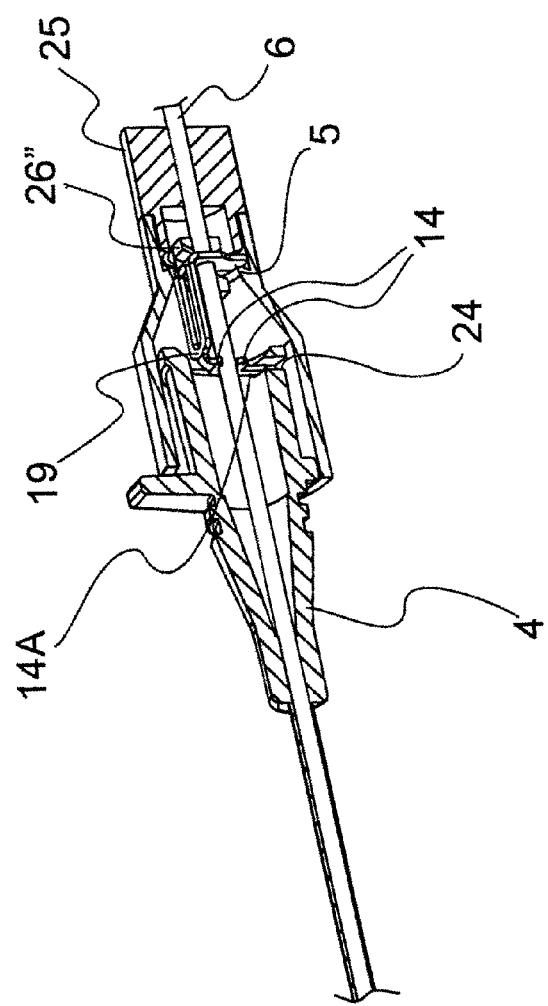
FIG. 47 is a cross-sectional perspective view of another embodiment of the medical needle shield apparatus shown in FIG. 1.
Figure 48:
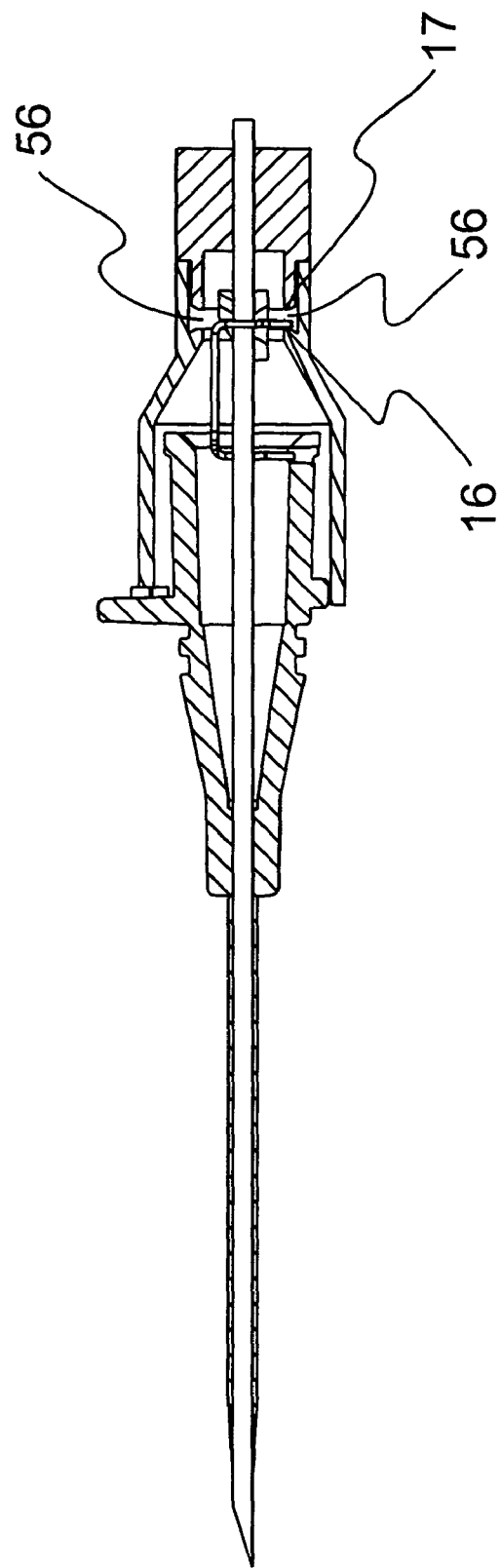
FIG. 48 is a cross-sectional view of the medical needle shield apparatus shown in FIG. 47.
Figure 49:
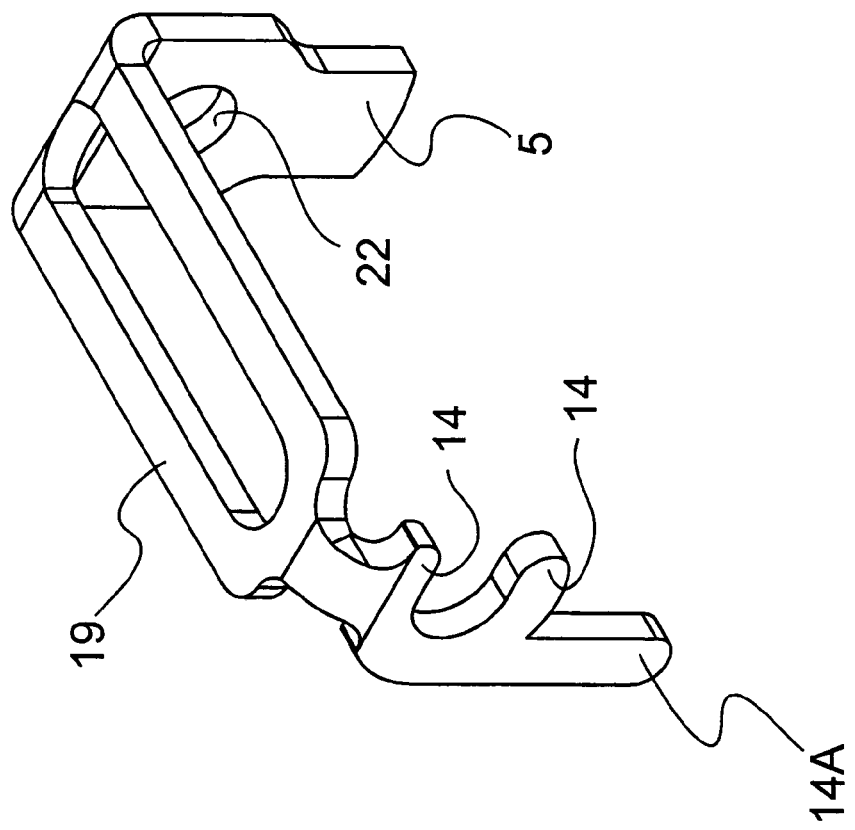
FIG. 49 is an enlarged perspective view of the binding member of the medical needle shield apparatus shown in FIG. 47.
Figure 50:
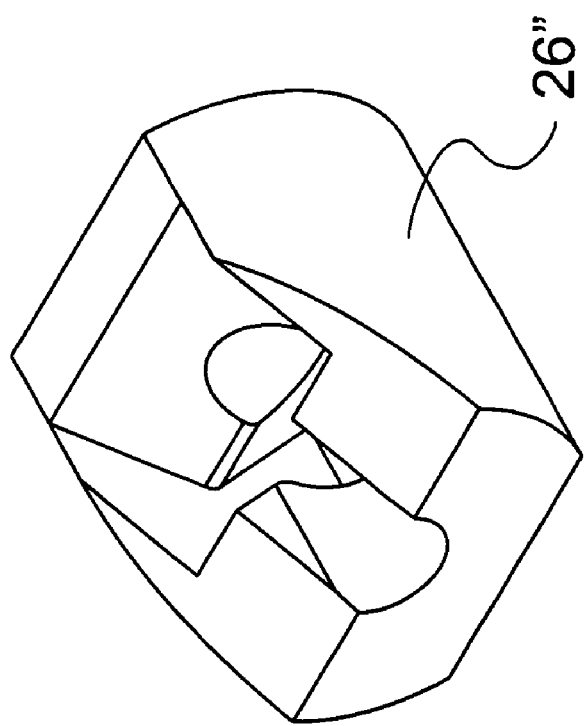
FIG. 50 is an enlarged perspective view of the unitary friction member of the medical needle shield apparatus shown in FIG. 47.
Figure 51:
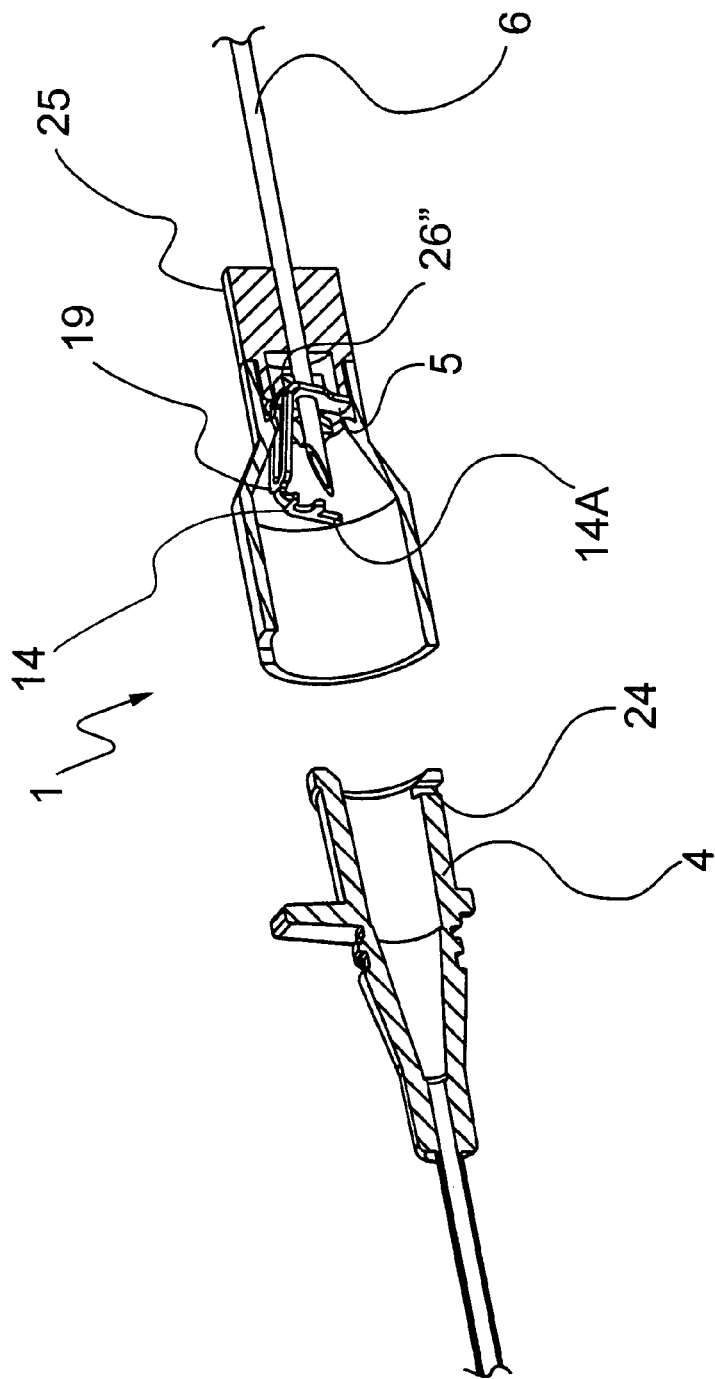
FIG. 51 is a cross-sectional perspective view of the medical needle shield apparatus shown in FIG. 47 in the extended position.

Referring to FIGS. 47-52, another alternate embodiment of the medical needle safety apparatus is shown. The illustrated embodiments depict a rotatable shield wherein the binding member 5 rotates about bearing surfaces provided in cavity 56. FIGS. 47 and 48 illustrate shield 1 prior to activation. Retainer 14 extends from end sensing member 19, wherein retainer 14 supports the needle on opposing sides and maintains binding member 5 in a non-binding position prior to the shield being in the extended position. Binding member 5 is disposed in friction member 26" that forms a monolithic member for receiving needle 6 for slidable receipt via friction between the retracted position and extended position of shield 1, as shown in FIG. 50. As needle 6 is retracted and shield 1 is extended, friction member 26" creates a drag force via engagement with needle 6 on binding member 5, as shown in FIGS. 47 and 48, causing binding member 5 to rotate to the binding orientation. Blocking member surfaces 16 and 17 engage binding member 5 to facilitate rotation thereof from the perpendicular orientation into the binding orientation such that binding surfaces 22 engage needle 6. This configuration prevents movement of needle 6. FIG. 51 illustrates shield 1 after activation, wherein the movement of retainer 14 upon activation of shield 1 in the extended position allows retainer 14 to move and release hub retainer 14A from slot 24.

Figure 52:
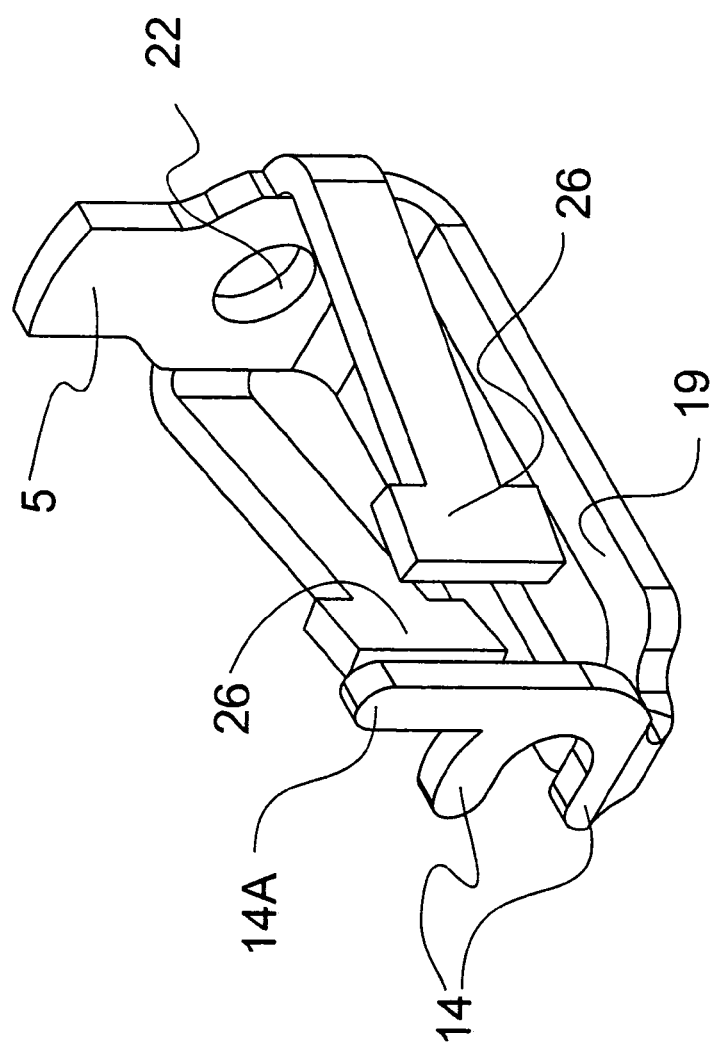
FIG. 52 is an enlarged perspective view of another embodiment of the binding member of the medical needle shield apparatus shown in FIG. 47.

FIG. 52 illustrates another embodiment of the binding member 5 having friction arms 26 to facilitate rotation of the binding member. It is envisioned that the embodiments including binding member 5 illustrated in FIG. 25 may have blocking members incorporated into the housing as discussed in previously disclosed embodiments.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
  a shield being extensible from a retracted position to an extended position to enclose a distal end of a needle;

a binding member disposed within the shield and comprising binding surfaces that define an aperture configured for slidable receipt of the needle between the retracted position and the extended position,
the binding member including a retainer extending therefrom such that the retainer is engageable with the needle to prevent inclination of the binding member while the retainer is engaged with the needle;
the binding member further comprising one or more drag inducing members that engage the needle during slidable receipt of the needle to create a drag force with the needle, the drag force and shield facilitating inclination of the binding member relative to a longitudinal axis of the needle once the retainer extends beyond the distal end of the needle such that the binding surfaces engage the needle to prevent slidable movement of the needle in the extended position of the shield; and
a hub retainer being configured to engage a catheter hub.

2. A medical needle shield apparatus as recited in claim 1, wherein the binding member includes a substantially planar aperture plate that includes the binding surfaces that form the aperture.

3. A medical needle shield apparatus as recited in claim 2, wherein the aperture plate is substantially perpendicular relative to the longitudinal axis of the needle due to engagement of the retainer with the needle prior to the shield being in the extended position.

4. A medical needle shield apparatus as recited in claim 1, wherein the retainer includes a first portion extending from the binding member and a second portion extending from the first portion.

5. A medical needle shield apparatus as recited in claim 4, wherein the first portion extends from the binding member in substantially parallel alignment with the needle due to engagement of the retainer with the needle.

6. A medical needle shield apparatus as recited in claim 4, wherein the second portion extends transversely relative to the longitudinal axis of the needle and is configured for engagement with the needle.

7. A medical needle shield apparatus as recited in claim 6, wherein the second portion has a substantially planar portion for engagement with the needle.

8. A medical needle shield apparatus as recited in claim 1, wherein the at least one drag inducing member includes the aperture of the binding member such that the aperture engages the needle to create the drag force with the needle.

9. A medical needle shield apparatus as recited in claim 1, wherein the at least one drag inducing member includes a pair of friction members that extend to engage the needle to create the drag force with the needle.

10. A medical needle shield apparatus as recited in claim 1, wherein the at least one drag inducing member includes at least one friction member disposed on the needle.

11. A medical needle shield apparatus as recited in claim 1 wherein the at least one drag inducing member is integral to the binding member.

12. A medical needle shield apparatus as recited in claim 1, wherein the at least one drag inducing member includes a material having a smaller aperture than the aperture of the binding member.

13. A medical needle shield apparatus as recited in claim 12, wherein the material is formed of a resilient material.

14. A medical needle shield apparatus as recited in claim 1 wherein the at least one drag inducing member includes a separate unitary friction element disposed on the medical needle.

15. A medical needle shield apparatus as recited in claim 14, wherein the unitary friction element includes friction elements for inclining the binding member and the aperture of the binding member is disposed between the friction elements.

16. A medical needle shield apparatus as recited in claim 1, wherein the at least one drag inducing members includes separate friction elements disposed on the needle for inclining the binding member, and the aperture of the binding member is disposed between the friction elements.

17. A medical needle shield apparatus as recited in claim 1, wherein the shield includes a housing that defines at least one blocking member extending from an interior surface thereof, the at least one blocking member being engageable with the binding member for urging the binding member to the binding orientation.

18. A medical needle shield apparatus as recited in claim 1, wherein the binding member is rotatable, relative to the longitudinal axis of the needle, between a non-binding orientation whereby the needle is slidable relative to the binding member and a binding orientation whereby the binding surfaces engage the needle to prevent slidable movement of the needle in the extended position of the shield.

19. A medical needle shield apparatus as recited in claim 1, further comprising a rotatable housing for relative rotational movement about the needle.

20. A medical needle shield apparatus as recited in claim 19, wherein the shield is supported for relative rotational movement by the rotatable housing by at least one bearing.

21. The medical needle shield apparatus according to claim 20, wherein the hub retainer is disposed on the at least one bearing.

22. The medical needle shield apparatus according to claim 20, wherein the at least one bearing defines at least one blocking member extending from an interior surface thereof, the at least one blocking member being engageable with the binding member for urging the binding member to the binding orientation.

23. The medical needle shield apparatus according to claim 1, wherein the hub retainer is disposed on the housing.

24. The medical needle shield apparatus according to claim 1, wherein the retainer and hub retainer are monolithically formed such that the hub retainer extends from the retainer.

25. A medical needle shield apparatus as recited in claim 1, further comprising a means for extending the shield to the distal end of the needle.

26. A medical needle shield apparatus as recited in claim 1, further comprising a retainer shield to protect the hub retainer from being inadvertently moved from its intended position.

27. A medical needle shield apparatus comprising:
a shield being extensible from a retracted position to an extended position to enclose a distal end of a needle;
a binding member disposed within the shield and including an aperture for slidable receipt of the needle between the retracted position and the extended position,
the binding member comprising retainer means for preventing inclination of the binding member;
the binding member further comprising drag inducing means for facilitating inclination of the binding member relative to a longitudinal axis of the needle by frictional drag forces between the drag inducing means and needle once the retainer extends beyond the distal end of the needle, and binding surface means for engaging the needle to prevent slidable movement of the needle in the extended position of the shield; and
hub retainer means for releasably engaging a catheter hub.

28. A medical needle shield apparatus as recited in claim 27, wherein the binding member is rotatable, relative to the longitudinal axis of the needle, between a non-binding orientation whereby the needle is slidable relative to the binding member and a binding orientation whereby the binding surface means engages the needle to prevent slidable movement of the needle in the extended position of the shield.

29. A medical needle shield apparatus as recited in claim 27, further comprising a rotatable housing for relative rotational movement about the needle.

30. A medical needle shield apparatus as recited in claim 29, wherein the shield is supported for relative rotational movement by the rotatable housing by at least one bearing.

31. A medical needle shield apparatus as recited in claim 30, wherein the hub retainer means is disposed on the at least one bearing.

32. A medical needle shield apparatus as recited in claim 30, wherein the at least one bearing defines at least one blocking member extending from an interior surface thereof, the at least one blocking member being engageable with the binding member for urging the binding member to the binding orientation.

33. A medical needle shield apparatus as recited in claim 27, wherein the hub retainer means is disposed on the housing.

34. A medical needle shield apparatus as recited in claim 27, wherein the at least one drag inducing member includes at least one friction member disposed on the needle.

35. A medical needle shield apparatus as recited in claim 27, wherein the at least one drag inducing member is integral to the binding member.

36. A medical needle shield apparatus as recited in claim 27, wherein the at least one drag inducing member includes a separate unitary friction element disposed on the medical needle.

37. A medical needle shield apparatus as recited in claim 36, wherein the unitary friction element includes friction elements for inclining the binding member and the aperture of the binding member is disposed between the friction elements.

38. A medical needle shield apparatus as recited in claim 27, wherein the at least one drag inducing members includes separate friction elements disposed on the needle for inclining the binding member, and the aperture of the binding member is disposed between the friction elements.

39. A medical needle shield apparatus as recited in claim 27, further comprising a means for extending the shield to the distal end of the needle.

40. A medical needle shield apparatus comprising:
a shield being extensible from a retracted position to an extended position to enclose a distal end of a needle;
a rotatable housing that encloses the shield, the rotatable housing supporting the shield for relative rotational movement therewith;
a hub retainer being configured to engage a catheter hub;
a binding member disposed within the shield and comprising binding surfaces that define an aperture configured for slidable receipt of the needle between the retracted position and the extended position,
the binding member including a retainer extending therefrom such that the retainer is engageable with the needle to prevent inclination of the binding member while the retainer is engaged with the needle; and
the binding member further comprising one or more drag inducing members that engage the needle during slidable receipt of the needle to create a drag force with the needle, the drag force and shield facilitating inclination of the binding member relative to a longitudinal axis of the needle once the retainer extends beyond the distal end of the needle such that the binding surfaces engage the needle to prevent slidable movement of the needle in the extended position of the shield.

41. A medical needle shield apparatus as recited in claim 40, wherein the shield is supported for relative rotational movement by the rotatable housing by at least one bearing.

42. A medical needle shield apparatus comprising:
a shield being extensible from a retracted position to an extended position to enclose a distal end of a needle;
means for binding the shield to the needle in the extended position by enabling the binding means to incline relative to a longitudinal axis of the needle to lock against the needle and for permitting engagement with the needle to prevent inclination and to sense the end of the needle until the shield is in the extended position, wherein the binding means is disposed in the shield; and
wherein the binding means further comprises a hub retainer means for releasably engaging a catheter hub such that upon activation of the binding means the hub retainer means moves to release the catheter hub from the shield so that the catheter hub and shield can be separated.

43. A medical needle shield apparatus as recited in claim 42, wherein the
binding means is able to incline relative to the longitudinal axis of the needle and lock against the needle due to a drag force with the needle.

44. A medical needle shield apparatus as recited in claim 42, wherein the binding means comprises:
a binding member disposed within the shield and defining binding surfaces that bind to the needle as the shield is in the extended position;
a sliding member disposed within the shield for slidable receipt of the needle between the retracted position and the extended position, the sliding member including a cavity for receipt of the binding member; and
ramp surfaces disposed on the shield for positioning the binding member in locking engagement with the needle in the extended position.

45. A medical needle shield apparatus as recited in claim 42, wherein the hub retainer means is configured to fit into a slot of a catheter hub.

46. A medical needle shield apparatus as recited in claim 42, wherein the shield is configured such that only the hub retainer means holds the shield together with a catheter hub.

47. A medical needle shield apparatus comprising:
a shield being extensible from a retracted position to an extended position to enclose a distal end of a needle;
a hub retainer being configured to engage a catheter hub, the shield further including a control surface for engaging an outer surface of the catheter hub for guiding and supporting extension of the catheter hub therefrom;
a binding member disposed within the shield and comprising binding surfaces that define an aperture configured for slidable receipt of the needle between the retracted position and the extended position,
the binding member comprising a retainer extending therefrom such that the retainer is engageable with the needle to prevent inclination of the binding member while the retainer is engaged with the needle, and
the binding member further comprising one or more drag inducing members that engage the needle during slidable receipt of the needle to create a drag force with the needle, the drag force and shield facilitating inclination of the binding member relative to a longitudinal axis of the needle once the retainer extends beyond the distal end of the needle such that the binding surfaces engage the needle to prevent slidable movement of the needle in the extended position of the shield.

48. A medical needle shield apparatus comprising:
a shield being extensible from a retracted position to an extended position to enclose a distal end of a needle;
a binding member disposed within the shield and comprising binding surfaces that define an aperture,
  the binding member comprising a retainer extending therefrom such that the retainer is engageable with the needle to prevent inclination of the binding member while the retainer is engaged with the needle, and
  the binding member further comprising one or more drag inducing members that engage the needle; and
  the binding member further comprising a hub retainer configured to releasably engage a catheter hub.

49. A medical needle shield apparatus as recited in claim 48, wherein the hub retainer is configured to fit into a slot of a catheter hub.

50. A medical needle shield apparatus as recited in claim 48, wherein the shield is configured such that only the hub retainer holds the shield together with a catheter hub.

51. A medical needle shield apparatus as recited in claim 48, wherein the binding member is configured such that inclination of the binding member moves the hub retainer to release the shield from a catheter hub.

52. A medical needle shield apparatus as recited in claim 48, wherein the binding means is configured such that inclination of the binding means moves the hub retainer means to release the shield from a catheter hub.

* * * * *